US011649431B2

(12) United States Patent
Studer et al.

(10) Patent No.: US 11,649,431 B2
(45) Date of Patent: May 16, 2023

(54) CORTICAL INTERNEURONS AND OTHER NEURONAL CELLS PRODUCED BY THE DIRECTED DIFFERENTIATION OF PLURIPOTENT AND MULTIPOTENT CELLS

(71) Applicants: MEMORIAL SLOAN-KETTERING CANCER CENTER, New York, NY (US); CORNELL UNIVERSITY, Ithaca, NY (US)

(72) Inventors: Lorenz Studer, New York, NY (US); Asif M. Maroof, Bowie, MA (US); Stewart Anderson, Philadelphia, PA (US)

(73) Assignees: MEMORIAL SLOAN-KETTERING CANCER CENTER, New York, NY (US); CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/922,110

(22) Filed: Oct. 23, 2015

(65) Prior Publication Data

US 2016/0115448 A1 Apr. 28, 2016

Related U.S. Application Data

(63) Continuation of application No. PCT/US2014/035760, filed on Apr. 28, 2014.

(60) Provisional application No. 61/816,624, filed on Apr. 26, 2013.

(51) Int. Cl.
*C12N 5/0793* (2010.01)
*G01N 33/50* (2006.01)

(52) U.S. Cl.
CPC ....... *C12N 5/0619* (2013.01); *G01N 33/5029* (2013.01); *G01N 33/5058* (2013.01); *G01N 33/5073* (2013.01); *G01N 33/5088* (2013.01); *C12N 2501/15* (2013.01); *C12N 2501/41* (2013.01); *C12N 2501/415* (2013.01); *C12N 2501/999* (2013.01); *C12N 2502/08* (2013.01); *C12N 2506/02* (2013.01)

(58) Field of Classification Search
None
See application file for complete search history.

(56) References Cited

U.S. PATENT DOCUMENTS

| 5,166,065 | A | 11/1992 | Williams et al. |
|---|---|---|---|
| 5,340,740 | A | 8/1994 | Petitte et al. |
| 5,453,357 | A | 9/1995 | Hogan |
| 5,523,226 | A | 6/1996 | Wheeler |
| 5,589,376 | A | 12/1996 | Anderson et al. |
| 6,610,540 | B1 | 8/2003 | Csete et al. |
| 6,787,356 | B1 | 9/2004 | Studer et al. |
| 6,833,269 | B2 | 12/2004 | Carpenter |
| 6,887,706 | B2 | 5/2005 | Zhang et al. |
| 7,005,252 | B1 | 2/2006 | Thomson |
| 7,011,828 | B2 | 3/2006 | Reubinoff et al. |
| 7,112,437 | B2 | 9/2006 | Pera |
| 7,211,434 | B2 | 5/2007 | Van Der Kooy et al. |
| 7,252,995 | B2 | 8/2007 | Fu et al. |
| 7,294,510 | B2 | 11/2007 | Okano et al. |
| 7,297,539 | B2 | 11/2007 | Mandalam et al. |
| 7,332,336 | B2 | 2/2008 | Ochiya et al. |
| 7,368,115 | B2 | 5/2008 | Ohta et al. |
| 7,763,463 | B2 | 7/2010 | Carpenter et al. |
| 7,892,830 | B2 | 2/2011 | Bergendahi et al. |
| 8,153,422 | B2 | 4/2012 | Isacson et al. |
| 8,153,428 | B2 | 4/2012 | Carpenter et al. |
| 8,252,585 | B2 | 8/2012 | Carpenter |
| 8,252,586 | B2 | 8/2012 | Carpenter et al. |
| 8,323,971 | B2 | 12/2012 | Pedersen et al. |
| 8,551,783 | B2 | 10/2013 | Kim et al. |
| 8,642,334 | B2 | 2/2014 | Chambers et al. |
| 8,883,502 | B2 | 11/2014 | Zhang et al. |
| 8,932,857 | B2 | 1/2015 | Yamanaka et al. |
| 9,249,389 | B2 | 2/2016 | Isacson et al. |
| 9,453,198 | B2 | 9/2016 | Studer et al. |
| 9,487,751 | B2 | 11/2016 | Anderson et al. |

(Continued)

FOREIGN PATENT DOCUMENTS

| CA | 2923592 A1 | 3/2015 |
|---|---|---|
| CN | 102191221 A | 9/2011 |

(Continued)

OTHER PUBLICATIONS

Brevini et al., 2010, Theriogenology, vol. 74, pp. 544-550 (Year: 2010).*

(Continued)

*Primary Examiner* — Emily A Cordas
*Assistant Examiner* — Maytee Marie Contes De Jesus
(74) *Attorney, Agent, or Firm* — Baker Botts L.L.P.

(57) ABSTRACT

Provided are cortical interneurons and other neuronal cells and in vitro methods for producing such cortical interneurons and other neuronal cells by the directed differentiation of stem cells and neuronal progenitor cells. The present disclosure relates to novel methods of in vitro differentiation of stem cells and neural progenitor cells to produce several type neuronal cells and their precursor cells, including cortical interneurons, hypothalamic neurons and pre-optic cholinergic neurons. The present disclose describes the derivation of these cells via inhibiting SMAD and Wnt signaling pathways and activating SHH signaling pathway. The present disclosure relates to the novel discovery that the timing and duration of SHH activation can be harnessed to direct controlled differentiation of neural progenitor cells into either cortical interneurons, hypothalamic neurons or pre-optic cholinergic neurons. The present disclosure also relates to compositions of cortical interneurons, hypothalamic neurons or pre-optic cholinergic neurons, and their precursors, that are highly enriched and can be used in variety of application. These cells can be used therapeutically to treat neurodegenerative and neuropsychiatric disorders, and can be used for disease modeling and drug screening.

21 Claims, 12 Drawing Sheets

(56) References Cited

U.S. PATENT DOCUMENTS

| | | |
|---|---|---|
| 2003/0036195 A1 | 2/2003 | Studer et al. |
| 2003/0211605 A1 | 11/2003 | Lee et al. |
| 2004/0005704 A1 | 1/2004 | Csete et al. |
| 2004/0087478 A1 | 5/2004 | Gillen et al. |
| 2004/0214324 A1 | 10/2004 | Isacson et al. |
| 2005/0260747 A1 | 11/2005 | Reubinoff et al. |
| 2006/0078543 A1 | 4/2006 | Reubinoff et al. |
| 2007/0224650 A1 | 9/2007 | Jessell et al. |
| 2009/0035285 A1 | 2/2009 | Condie et al. |
| 2010/0009442 A1 | 1/2010 | Sasai et al. |
| 2010/0093090 A1 | 4/2010 | Deng et al. |
| 2010/0099772 A1 | 4/2010 | Bean et al. |
| 2011/0229441 A1 | 9/2011 | Benchoua et al. |
| 2012/0040393 A1 | 2/2012 | Zhang et al. |
| 2012/0094381 A1 | 4/2012 | Chambers et al. |
| 2012/0142093 A1 | 6/2012 | Takahashi et al. |
| 2012/0148549 A1* | 6/2012 | Anderson .............. A61K 35/30 424/93.21 |
| 2012/0322146 A1 | 12/2012 | Carpenter et al. |
| 2013/0108669 A1 | 5/2013 | Cooper et al. |
| 2013/0183674 A1 | 7/2013 | Studer et al. |
| 2014/0199274 A1 | 7/2014 | Kim et al. |
| 2014/0248696 A1 | 9/2014 | Zhang et al. |
| 2014/0314721 A1 | 10/2014 | Semechkin et al. |
| 2015/0010514 A1 | 1/2015 | Studer et al. |
| 2015/0010515 A1 | 1/2015 | Schoeler et al. |
| 2015/0030570 A1 | 1/2015 | Pan et al. |
| 2015/0086481 A1 | 3/2015 | Ganat et al. |
| 2015/0087541 A1 | 3/2015 | Gonzalez et al. |
| 2015/0265652 A1 | 9/2015 | George et al. |
| 2015/0353888 A1 | 12/2015 | Inoue et al. |
| 2015/0361393 A1* | 12/2015 | Nicholas .............. C12N 5/0618 435/366 |
| 2016/0108362 A1 | 4/2016 | Su et al. |
| 2016/0115444 A1 | 4/2016 | Studer et al. |
| 2016/0115448 A1 | 4/2016 | Studer et al. |
| 2016/0145582 A1 | 5/2016 | Yu |
| 2016/0201032 A1 | 7/2016 | Studer et al. |
| 2016/0326491 A1 | 11/2016 | Chambers et al. |
| 2019/0062700 A1* | 2/2019 | Nicholas .............. C12N 5/0619 |

FOREIGN PATENT DOCUMENTS

| | | |
|---|---|---|
| EP | 1 645 286 A1 | 4/2006 |
| KR | 101331034 B1 | 11/2013 |
| WO | WO 2003/000868 A1 | 1/2003 |
| WO | WO 2007/113505 A2 | 10/2007 |
| WO | WO 2008/018190 A1 | 2/2008 |
| WO | WO 2009/024448 A1 | 2/2009 |
| WO | WO 2009/099152 A1 | 8/2009 |
| WO | WO 2009/148170 A1 | 12/2009 |
| WO | WO 2010/063 848 A1 | 6/2010 |
| WO | WO 2010/096496 A2 | 8/2010 |
| WO | WO 2010/141622 A2 | 12/2010 |
| WO | WO 2011/019092 A1 | 2/2011 |
| WO | WO 2011/108766 A1 | 9/2011 |
| WO | WO 2011/159726 A2 | 12/2011 |
| WO | WO 2014/176606 A1 | 10/2014 |
| WO | WO 2015/054526 A2 | 4/2015 |
| WO | WO 2015/143 622 A1 | 10/2015 |
| WO | WO 2016/063985 A1 | 4/2016 |
| WO | WO 2016/162747 A2 | 10/2016 |

OTHER PUBLICATIONS

Paris et al. (2010, Theriogenology, vol. 74, pp. 516-524); (Year: 2010).*
Munoz et al. (2009) Stem Cell Rev. and Rep., vol. 5, 6-9, (Year: 2009).*
Oliveri;et al ;(Regenerative Medicine, 2(5): 795-816 2007 (Year: 2007).*
Patel;el al., Stem;Cell Rev., 6(3): 367-380, 2010, (Year: 2010).*
Maroof et al (J Neurosci, 30(13): 4667-4675, 2010 (Year: 2010).*
Lupo et al, (Open Biol, 3: 1-13,2013, Published Apr. 10, 2013). (Year: 2013).*
Cai et al (Developmental Biology, 376: 62-73, 2013, published on line Jan. 23, 2013). (Year: 2013).*
U.S. Appl. No. 15/077,012, Sep. 12, 2017 Response to Non-Final Office Action.
U.S. Appl. No. 14/356,042, Sep. 19, 2017 Final Office Action.
U.S. Appl. No. 14/356,042, Aug. 21, 2017 Respone after Final Action.
U.S. Appl. No. 14/356,042, Jul. 24, 2017 Final Office Action.
Eldar-Finkelman et al., "GSK-3 inhibitors: preclinical and clinical focus on CNS," Frontiers in Molecular Neuroscience 4(32):1-18 (2011).
El Maarouf et al., "Use of polysialic acid in repair of the central nervous system," PNAS 103(45):16989-16994 (2006).
U.S. Appl. No. 13/201,137 U.S. Pat. No. 8,642,334, filed Nov. 10, 2011 (Feb. 4, 2014).
U.S. Appl. No. 13/697,274 U.S. Pat. No. 9,453,198, filed Jan. 22, 2013 (Sep. 27, 2016).
U.S. Appl. No. 14/168,835 (US 2017/0130199), filed Jan. 30, 2014 (May 11, 2017).
U.S. Appl. No. 14/169,286 (US 2017/0159012), filed Jan. 31, 2014 (Jun. 8, 2017).
U.S. Appl. No. 14/356,042 (US 2015/0010514), filed May 2, 2014 (Jan. 8, 2015).
U.S. Appl. No. 15/077,012 (US 2016/0201032), filed Mar. 22, 2016 (Jul. 14, 2016).
U.S. Appl. No. 13/201,137, Dec. 23, 2013 Issue Fee Payment.
U.S. Appl. No. 13/201,137, Sep. 24, 2013 Notice of Allowance.
U.S. Appl. No. 13/201,137, Sep. 17, 2013 Response after Final Action.
U.S. Appl. No. 13/201,137, Jul. 24, 2013 Final Office Action.
U.S. Appl. No. 13/201,137, Jun. 6, 2013 Response to Non-Final Office Action.
U.S. Appl. No. 13/201,137, Mar. 7, 2013 Non-Final Office Action.
U.S. Appl. No. 13/201,137, Jan. 24, 2013 Response to Restriction Requirement.
U.S. Appl. No. 13/201,137, Jan. 3, 2013 Restriction Requirement.
U.S. Appl. No. 13/697,274, Aug. 19, 2016 Issue Fee Payment.
U.S. Appl. No. 13/697,274, May 20, 2016 Notice of Allowance.
U.S. Appl. No. 13/697,274, Apr. 7, 2016 Request for Continued Examination (RCE).
U.S. Appl. No. 13/697,247, Mar. 24, 2016 Notice of Allowance.
U.S. Appl. No. 13/697,274, Mar. 24, 2016 Applicant Initiated Interview Summary.
U.S. Appl. No. 13/697,274, Mar. 22, 2016 Issue Fee Payment.
U.S. Appl. No. 13/697,274, Dec. 23, 2015 Notice of Allowance.
U.S. Appl. No. 13/697,274, Nov. 4, 2015 Response to Non-Final Office Action.
U.S. Appl. No. 13/697,274, May 5, 2015 Non-Final Office Action.
U.S. Appl. No. 13/697,274, Mar. 26, 2015 Response to Restriction Requirement.
U.S. Appl. No. 13/697,274, Dec. 26, 2014 Restriction Requirement.
U.S. Appl. No. 14/168,835, May 22, 2017 Non-Final Office Action.
U.S. Appl. No. 14/168,835, Jan. 27, 2017 Office of Petitions Decision.
U.S. Appl. No. 14/168,835, Sep. 15, 2016 Petition for review by the Office of Petitions.
U.S. Appl. No. 14/168,835, Mar. 15, 2016 Office of Petitions Decision.
U.S. Appl. No. 14/168,835, Nov. 26, 2014 Petition for review by the Office of Petitions.
U.S. Appl. No. 14/168,835, Sep. 30, 2014 Notice of Abandonment.
U.S. Appl. No. 14/169,286, Jun. 8, 2017 Restriction Requirement.
U.S. Appl. No. 14/169,286, Mar. 3, 2017 Office of Petitions Decision.
U.S. Appl. No. 14/169,286, Sep. 15, 2016 Petition for review by the Office of Petitions.
U.S. Appl. No. 14/169,286, Mar. 15, 2016 Office of Petitions Decision.
U.S. Appl. No. 14/169,286, Nov. 26, 2014 Petition for review by the Office of Petitions.
U.S. Appl. No. 14/169,286, Sep. 30, 2014 Notice of Abandonment.

(56) References Cited

OTHER PUBLICATIONS

U.S. Appl. No. 14/356,042, May 12, 2017 Response to Non-Final Office Action.
U.S. Appl. No. 14/356,042, Feb. 22, 2017 Non-Final Office Action.
U.S. Appl. No. 14/356,042, Feb. 2, 2017 Amendment and Request for Continued Examination (RCE).
U.S. Appl. No. 14/356,042, Aug. 2, 2016 Final Office Action.
U.S. Appl. No. 14/356,042, Jul. 11, 2016 Response to Non-Final Office Action.
U.S. Appl. No. 14/356,042, Mar. 9, 2016 Non-Final Office Action.
U.S. Appl. No. 14/356,042, Feb. 8, 2016 Response to Restriction Requirement.
U.S. Appl. No. 14/356,042, Dec. 8, 2015 Restriction Requirement.
U.S. Appl. No. 15/077,012, Jun. 12, 2017 Non-Final Office Action.
"DAPI Nucleic Acid Stain," Molecular Probes, Invitrogen, Ltd. pp. 1-5 (2006).
Agarwal et al., "Efficient Differentiation of Functional Hepatocytes from Human Embryonic Stem Cells," Stem Cells, 26:1117-1127 (2008).
Aoki, et al., "Sox10 Regulates the Development of Neural Crest-Derived Melanocytes in Xenopus," Developmental Biology, 259(1):19-33 (2003).
Bailey et al., "Sensory Organs: Making and Breaking the Pre-Placodal Region," Current Topics in Developmental Biology, 72:167-204 (2006).
Baker et al., "Establishing neuronal identity in vertebrate neurogenic placodes," Development, 127:3045-3056 (2000).
Baker et al., "Vertebrate cranial placodes I. Embryonic induction," Dev Biol., 232(1):1-61, pp. 1-30 (2001a).
Baker et al., "Vertebrate cranial placodes I. Embryonic induction," Dev Biol., 232(1):1-61, pp. 31-61(200lb).
Bansal et al., "Specific Inhibitor of FGF Receptor Signaling: FGF-2-Mediated Effects on Proliferation, Differentiation, and MAPK Activation are Inhibited by PD 173074 in Oligodendrocyte-Lineage Cells," Journal of Neuroscience, Research, 74(4):486-493 (2003).
Barberi et al., "Derivation of engraftable skeletal myoblasts from human embryonic stem cells," Nat Med, 13(5):642-648 (2007).
Barberi et al., "Derivation of Multipotent Mesenchymal Precursors from Human Embryonic Stem Cells," PLoS Med, 2(6):e161 (2005).
Barberi et al., "Neural subtype specification of fertilization and nuclear transfer embryonic stem cells and application in parkinsonian mice," Nat Biotechnol. 10:1200-1207 (2003).
Bennett et al., "Regulation of Wnt Signaling During Adipogenesis," J Biol Chem., 277(34):30998-31004 (2002).
Bhattacharyya et al., "Hierarchy of regulatory events in sensory placode development," Curr Opin Genet Dev. 14(5):520-6 (2004).
Bouwmeester et al., "Cerberus is a head-inducing secreted factor expressed in the anterior endoderm of Spemann's organizer," Nature, 382:595-601 (1996).
Bradley et al., "Formation of germ-line chimaeras from embryo-derived teratocarcinoma cell lines," Nature 309:255-256 (1984).
Briscoe and Ericson, "The specification of neuronal identity by graded Sonic Hedgehog signalling," Semin Cell Dev Biol. 3:353-62 (1999).
Brivanlou and Darnell, "Signal Transduction and the Control of Gene Expression," Science, 295(5556):813-818 (2002).
Bystron et al., "The First Neurons of the Human Cerebral Cortex," Nat Neurosci., 9(7):880-886 (2006).
Cadigan and Liu, "Wnt Signaling: Complexity at the Surface," J Cell Sci., 119(Pt 3):395-402 (2006).
Callaerts et al., "PAX-6 in Development and Evolution," Annu. Rev. Neurosci. 20:483-532 (1997).
Chambers et al., "Combined small-molecule inhibition accelerates developmental timing and converts human pluripotent stem cells into nociceptors," Nature Biotechnology 30(7):715-720 (2012).
Chambers et al., "Dual-SMAD Inhibition/WNT Activation-Based Methods to Induce Neural Crest and Derivatives from Human Pluripotent Stem Cells," Methods in Molecular Biology (2013) DOI 10.1007/7651_2013_59.
Chambers, et al., "Highly efficient neural conversion of human ES and iPS cells by dual inhibition of SMAD signaling," Nat Biotechnol, Corrigendum: in Nature Biotechnology 27(3):275-280 (2009).
Charrier et al., "Dual origin of the floor plate in the avian embryo," Development 129:4785-4796 (2002).
Charron et al., "The Morphogen Sonic Hedgehog is an Axonal Chemoattractant that Collaborates with Netrin-1 in Midline Axon Guidance," Cell 113:11-23 (2003).
Chen et al., "Immortalization and characterization of a nociceptive dorsal root ganglion sensory neuronal line," J Peripher Nerv Syst., 12(2):121-130 (2007).
Cooper et al., "Differentiation of human ES and Parkinson's disease iPS cells into ventral midbrain dopaminergic neurons requires a high activity form of SHH, FGF8a and specific regionalization by retinoic acid", Molecular and Cellular Neurosciences, 45(3):258-266 (2010).
Crawford et al., "The Notch Response Inhibitor DAPT Enhances Neuronal Differentiation in Embryonic Stem Cell-Derived Embryoid Bodies Independently of Sonic Hedgehog Signaling," Developmental Dynamics, 236:886-892 (2007).
Cuny et al., "Structure-Activity Relationship Study of Bone Morphogenetic Protein (BMP) Signaling Inhibitors," Bioorg Med Chem Lett., 18(15):4388-4392 (2008).
D'Amour et al., "Efficient differentiation of human embryonic stem cells to definitive endoderm," Nat Biotechnol, 23(12):1534-1541 (2005).
Dennis et al., "DAVID: Database for Annotation, Visualization, and Integrated Discovery," Genome Biology 4:R60 (2003).
Dezawa et al., "Potential of Bone Marrow Stromal Cells in Applications for Neuro-Degenerative, Neuro-Traumatic and Muscle Degenerative Diseases," Current Neuropharmacology, 3:257-266 (2005).
Doble and Woodgett, "GSK-3: Tricks of the Trade for a Multi-Tasking Kinase," Journal of Cell Science, 116(7):1175-1186 (2003).
Doetschman et al. "Establishment of Hamster Blastocyst-Derived Embryonic Stem (ES) Cells," Dev Biol., 127:224-227 (1988).
Dorsky et al., "Control of Neural Crest Cell Fate by the Wnt Signalling Pathway," Nature, 396(6709):370-373 (1998).
Dovey et al., "Functional Gamma-Secretase Inhibitors Reduce Beta-Amyloid Peptide Levels in Brain," J Neurochem., 76(1):173-181 (2001).
Ebendal et al., "Bone Morphogenetic Proteins and Their Receptors: Potential Functions in the Brain," Journal of Neuroscience, Research, 51(2):139-146 (1998).
Eiraku et al., "Self-organized formation of polarized cortical tissues from ESCs and its active manipulation by extrinsic signals," Cell Stem Cell, 3:519-53 (2008).
Elkabetz et al., "Human ES cell-derived neural rosettes reveal a functionally distinct early neural stem cell stage," Genes Dev., 22:152-165 Erratum (2008).
Elkabetz et al., "Human ES Cell-Derived Neural Rosettes Reveal a Functionally Distinct Early Neural Stem Cell Stage," Genes Dev., 22(2):152-165 (2008).
Erceg et al., "Human Embryonic Stem Cell Differentiation Toward Regional Specific Neural Precursors," Stem Cells, 27:78-87 (2009).
Ericson et al., "Two Critical Periods of Sonic Hedgehog Signaling Required for the Specification of Motor Neuron Identity," Cell, 87:661-673 (1996).
Evans et al., "Derivation and preliminary characterization of pluripotent cell lines from porcine and bovine blastocysts," Theriogenology, 33(1):125-128 (1990).
Evans et al., "Establishment in culture of pluripotential cells from mouse embryos," Nature, 292:154-156(1981).
Extended European Search Report dated Mar. 10, 2015 issued in European Patent Application No. 12846715.6.
Fang et al., "Electrophysiological Differences Between Nociceptive and Non-Nociceptive Dorsal Root Ganglion Neurones in the Rat In Vivo," The Journal of Physiology, 565(3):927-943 (2005).
Fasano et al., "Bmi-1 cooperates with Foxgl to maintain neural stem cell self-renewal in the fore brain," Genes Dev., 23:561-574 (2009).
Fasano et al., "Bmi-1 cooperates with Foxgl to maintain neural stem cell self-renewal in the fore brain," Genes Dev., 23:561-574 Suppl. Fig. 1 (2009).

(56) References Cited

OTHER PUBLICATIONS

Fasano et al., "Bmi-1 cooperates with Foxgl to maintain neural stem cell self-renewal in the fore brain," Genes Dev., 23:561-574 Suppl. Fig. 2 (2009).
Fasano et al., "Bmi-1 cooperates with Foxgl to maintain neural stem cell self-renewal in the fore brain," Genes Dev., 23:561-574 Suppl. Fig. 3 (2009).
Fasano et al., "Bmi-1 cooperates with Foxgl to maintain neural stem cell self-renewal in the fore brain," Genes Dev., 23:561-574 Suppl. Fig. 4 (2009).
Fasano et al., "Bmi-1 cooperates with Foxgl to maintain neural stem cell self-renewal in the fore brain," Genes Dev., 23:561-574 Suppl. Fig. legends (2009).
Fasano et al., "Bmi-1 cooperates with Foxgl to maintain neural stem cell self-renewal in the fore brain," Genes Dev., 23:561-574 Suppl. Materials (2009).
Fasano et al., "shRNA knockdown of Bmi-1 reveals a critical role for p21-Rb pathway in NSC self-renewal during development," Cell Stem Cell, 1:87-99 (2007).
George et al., "Nociceptive Sensory Neurons Derive From Contralaterally Migrating, Fate-Restricted Neural Crest Cells," Nat Neurosci., 10(10):1287-1293 (2007).
Gerdes et al., "Production of a Mouse Monoclonal Antibody Reactive With a Human Nuclear Antigen Associated With Cell Proliferation," Int J Cancer, 31(1):13-20 (1983).
Gerrero et al., "Bm-3.0: A POU-Domain Protein Expressed in the Sensory, Immune, and Endocrine Systems That Functions on Elements Distinct From Known Octamer Motifs," PNAS USA, 90(22):10841-10845 (1993).
Giles et al., "Pluripotency of Cultured Rabbit Inner Cell Mass Cells Detected by Isozyme Analysis and Eye Pigmentation of Fetuses Following Injection into Blastocysts or Morulae," Mol. Reprod and Dev., 36:130-138 (1993).
Glinka et al., "Dickkopf-1 is a member of a new family of secreted proteins and functions in head induction," Nature, 391:357-362 (1998).
Gordon et al., "Wnt Signaling: Multiple Pathways, Multiple Receptors, and Multiple Transcription Factors," The Journal of Biological Chemistry, 281(32):22429-22433 (2006).
Grappe et al., "Structural basis of BMP signalling inhibition by the cystine knot protein Noggin," Nature, 420:636-642 (2002).
Graves et al., "Derivation and Characterization of Putative Pluripotential Embryonic Stem Cells from Preimplantation Rabbit Embryos," Mol. Reprod and Dev., 36:424-433 (1993).
Hemmati-Brivanlou et al., "Follistatin, an Antagonist of Activin, is Expressed in the Spemann Organizer and Displays Direct Neuralizing Activity," Cell, 77:283-295 (1994).
Hendzel et al., "Mitosis-Specific Phosphorylation of Histone H3 Initiates Primarily Within Pericentromeric Heterochromatin During G2 and Spreads in an Ordered Fashion Coincident With Mitotic Chromosome Condensation," Chromosoma., 106(6):348-360 (1997).
Hogan, "Bone Morphogenetic Proteins: Multifunctional Regulators of Vertebrate Development," Genes Dev., 10(13):1580-1594 (1996).
Huang et al., "Bioinformatics enrichment tools: paths toward the comprehensive functional analysis of large gene lists," Nucleic Acids Res., 37(1):1-13 (2009).
Huang et al., "Systematic and integrative analysis of large gene lists using DAVID Bioinformatics Resources," Nat Protoc., 4(1):44-57 (2009).
Hunter et al., "Retinoic acid stimulates neurite outgrowth in the amphibian spinal cord," PNAS USA, 88:3666-3670 (1991).
Iannaccone et al., "Pluripotent Embryonic Stem Cells from the Rat are Capable of Producing Chimeras," Dev. Biol. 163:288-292 (1994).
International Search Report dated Mar. 29, 2013 in International Patent Application No. PCT/US2012/063339.
International Search Report dated Nov. 11, 2010 in International Patent Application No. PCT/US10/024487.
ISR PCT/US2011/037179 dated Feb. 24, 2012.

Ivanova et al., "Dissecting self-renewal in stem cells with RNA interference," Nature, 442:533-538 (2006).
Jeong et al., "A functional screen for sonic hedgehog regulatory elements across a 1 Mb interval identifies long-range ventral forebrain enhancers," Development, 133:7761-7772 (2005).
Jeong et al., "Distinct regulators of SHH transcription in the floor plate and notochord indicate separate origins for these tissues in the mouse node," Development, 130:3891-3902 (2003).
Jessell et al., "Polarity and patterning in the neural tube: the origin and function of the floor plate," CibaFound Symp., 144:255-276, pp. 255-266 (1989a).
Jessell et al., "Polarity and patterning in the neural tube: the origin and function of the floor plate," CibaFound Symp., 144:255-276, pp. 267-276 (1989b).
Jessell et al., Polarity and patterning in the neural tube: the origin and function of the floor plate. Ciba Found Symp., (discussion) 144:276-280, 290-295 (1989).
Jessell, "Neuronal specification in the spinal cord: inductive signals and transcriptional codes," Nat Rev Genet., 1:20-29 (2000).
Jin et al., "MAPK/ERK and Wnt/β-Catenin pathways are synergistically involved in proliferation of Sca-1 positive hepatic progenitor cells", Biochemical and Biophysical Research Communications 409:803-807 (2011).
Joannides et al., "Automated Mechanical Passaging: A Novel and Efficient Method for Human Embryonic Stem Cell Expansion," Stem Cells, 24(2):230-235 (2006).
Joksimovic et al., "Wnt antagonism of Shh facilitates midbrain floor plate neurogenesis," Developmental Biology, vol. 331, No. 2, Jul. 15, 2009, pp. 507-508.
Joksimovic et al., "Wnt antagonism of SHH facilitates midbrain floor plate neurogenesis," Nat Neurosci., 12:125-131 (2009).
Kakegawa et al., International Association for Dental Research, General Session and Exhibition, Jun. 28-Jul. 1, Abstract #0267, Brisbane Australia.
Katoh et al., "Cross-talk of WNT and FGF Signaling Pathways at GSK3β to Regulate β-Catenin and SNAIL Signaling Cascades," Cancer Biology & Therapy, 5(9):1059-1064 (2006).
Kawasaki et al., "Induction of Midbrain Dopaminergic Neurons from ES Cells by Stromal Cell-Derived Inducing Activity," Neuron, 28:31-40 (2000).
Kikuchi et al., "Multiplicity of the Interactions of Wnt Proteins and Their Receptors," Cell Signal, 19(4):659-671 (2007).
Kim et al., "Oct4-Induced Pluripotency in Adult Neural Stem Cells," Cell, 136:411-419 (2009).
Kim et al., "Robust Enhancement of Neural Differentiation From Human ES and iPS Cells Regardless of Their Innate Difference in Differentiation Propensity," Stem Cell Reviews and Reports, 6(2):270-281 (2010).
Kimura-Yoshida et al., "Crucial roles of Foxa2 in mouse anterior-posterior axis polarization via regulation of anterior visceral endoderm-specific genes," PNAS, 104:5919-59249 with Data Supplement Figs. Legends SFig. 5 and SFig. 6 (2006).
Kirkeby et al., "Predictive Markers Guide Differentiation to Improve Graft Outcome in Clinical Translation of hESC Based Therapy for Parkinson's Disease," Cell Stem Cell, available online Oct. 27, 2016 (2016), downloaded Feb. 2, 2017 from <http://dx.doi.org/10.1016/j.stem.2016.09.004>.
Kitao et al., "Neurogenesis of Subpopulations of Rat Lumbar Dorsal Root Ganglion Neurons Including Neurons Projecting to the Dorsal Column Nuclei," The Journal of Comparative Neurology, 371(2):249-257 (1996).
Kittappa et al., "The foxa2 Gene Controls the Birth and Spontaneous Degeneration of Dopamine Neurons in Old Age," PLoS Biol., 5(12):e325 (2007).
Kodama et al., "Neurogenic Potential of Progenitors Derived from Human Circulating CD14+ Monocytes," Immunol. Cell Biol., 84(2):209-217 (2006).
Kriks S. et al., "Dopamine neurons derived from human ES cells efficiently engraft in animal models of Parkinson's disease," Nature, 480(7378):547-551 (2011).
Laflamme et al., "Cardiomyocytes derived from human embryonic stem cells in pro-survival factors enhance function of infarcted rat hearts," Nat Biotechnol., 25(9):1015-1024 (2007).

(56) References Cited

OTHER PUBLICATIONS

Lee et al., "Directed Differentiation and transplantation of Human Embryonic Stem Cell-Derived Motoneurons," Stem Cells, 25:1931-1939 (2007).
Lee et al., "Instructive Role of Wnt/B-Catenin in Sensory Fate Specification in Neural Crest Stem Cells," Science, 303(5660):1020-1023 (2004).
Lee et al., "Isolation and Directed Differentiation of Neural Crest Stem Cells Derived From Human Embryonic Stem Cells," Nat Biotechnol., 25(12):1468-1475 (2007).
Lee et al., "Modeling Pathogenesis and Treatment of Familial Dysautonomia using Patient-Specific iPSCs," Nature, 461(7262):402-406 (2009).
Lee et al., "The Expression and Posttranslational Modification of a Neuron-Specific B-Tubulin Isotype During Chick Embryo genesis," Cell Motility and the Cytoskeleton, 17(2):118-132 (1990).
Li et al., "Directed differentiation of ventral spinal progenitors and motor neurons from human embryonic stem cells by small molecules," Stem Cells, 4:886-893 (2008).
Li et al., "Rapid induction and long-term self-renewal of primitive neural precursors from human embryonic stem cells by small molecule inhibitors," PNAS 108(20):8299-8304 (2011).
Li et al., "Specification of Motoneurons From Human Embryonic Stem Cells," Nat Biotechnol., 23(2):215-221 (2005).
Lin et al., "Foxa1 and Foxa2 function both upstream of and cooperatively with Lmx1a and Lmx1b in a feedforward loop promoting mesodiencephalic dopaminergic neuron development," Genome & Development Control, Developmental Biology 333:386-396 (2009).
Lois et al., "Germline Transmission and Tissue-Specific Expression of Transgenes Delivered by Lentiviral Vectors," Science, 295:868-872 (2002).
Lyuksyutova et al., "Anterior-Posterior Guidance of Commissural Axons by Wnt-Frizzled Signaling," Science, 302:1984-1988 (2003).
Ma et al., "Neurogenin1 and Neurogenin2 Control Two Distinct Waves of Neurogenesis in Developing Dorsal Root Ganglia," Genes Dev., 13(13):1717-1728 (1999).
MacDonald et al., "Wnt/β-catenin signaling: components, mechanisms, and diseases," Developmental Cell, 17(1):9-26 (2009).
Marmigere and Ernfors, "Specification and Connectivity of Neuronal Subtypes in the Sensory Lineage," Nat Rev Neurosci., 8(2):114-127 (2007).
Martin, "Isolation of a pluripotent cell line from early mouse embryos cultured in medium conditioned by teratocarcinoma stem cells," PNAS USA, 78(12):7634-7638 (1981).
Matise et al., "Gli2 is required for induction of floor plate and adjacent cells, but not most ventral neurons in the mouse central nervous system," Development, 125:2759-2770 (1998).
Mehler et al., "Bone Morphogenetic Proteins in the Nervous System," Trends Neurosci., 20(7):309-317 (1997).
Mizuseki et al., "Generation of neural crest-derived peripheral neurons and floor plate cells from mouse and primate embryonic stem cells," PNAS USA, 100:5828-5833 (2003).
Mizuseki et al., "Generation of neural crest-derived peripheral neurons and floor plate cells from mouse and primate embryonic stem cells," PNAS USA, 100:5828-5833 Supporting Information List (2003).
Mizuseki et al., "Generation of neural crest-derived peripheral neurons and floor plate cells from mouse and primate embryonic stem cells," PNAS USA, 100:5828-5833 Supporting Materials and Methods (2003).
Mizuseki et al., "Generation of neural crest-derived peripheral neurons and floor plate cells from mouse and primate embryonic stem cells," PNAS USA, 100:5828-5833 Supporting Information Fig. 6 (2003).
Mizuseki et al., "Generation of neural crest-derived peripheral neurons and floor plate cells from mouse and primate embryonic stem cells," PNAS USA, 100:5828-5833 Supporting Fig. 6 (2003).

Mizuseki et al., "Generation of neural crest-derived peripheral neurons and floor plate cells from mouse and primate embryonic stem cells," PNAS USA, 100:5828-5833 Supporting Information Fig. 7 (2003).
Mizuseki et al., "Generation of neural crest-derived peripheral neurons and floor plate cells from mouse and primate embryonic stem cells," PNAS USA, 100:5828-5833 Supporting Fig. 7 (2003).
Mizuseki et al., "Generation of neural crest-derived peripheral neurons and floor plate cells from mouse and primate embryonic stem cells," PNAS USA, 100:5828-5833 Supporting Information Fig. 8 (2003).
Mizuseki et al., "Generation of neural crest-derived peripheral neurons and floor plate cells from mouse and primate embryonic stem cells," PNAS USA, 100:5828-5833 Supporting Fig. 8 (2003).
Mizuseki et al., "Generation of neural crest-derived peripheral neurons and floor plate cells from mouse and primate embryonic stem cells," PNAS USA, 100:5828-5833 Supporting Information Fig. 9 (2003).
Mizuseki et al., "Generation of neural crest-derived peripheral neurons and floor plate cells from mouse and primate embryonic stem cells," PNAS USA, 100:5828-5833 Supporting Fig. 9 (2003).
Mukhopadhyay et al., "Dickkopf1 is required for embryonic head induction and limb morphogenesis in the mouse," Dev Cell, 3:423-434 (2001).
Mullor et al., "Pathways and consequences: Hedgehog signaling in human disease," Trends Cell Biol 12:562-569 (2002).
Munoz-Sanjuan et al., "Neural Induction, The Default Model and Embryonic Stem Cells," Nat Rev Neurosci., 3:271-280 (2002).
Notarianni et al., "Maintenance and differentiation in culture of pluripotential embryonic cell lines from pig blastocysts," J. Reprod. Fert. Suppl., 41:51-56 (1990).
Ono et al., "Differences in neurogenic potential in floor plate cells along an anteroposterior location: midbrain dopaminergic neurons originate from mesencephalic floor plate cells," Development, 134:3213-3225 (2007).
Ono et al., "Differences in neurogenic potential in floor plate cells along an anteroposterior location: midbrain dopaminergic neurons originate from mesencephalic floor plate cells," Development, 134:3213-3225 Data Supplement (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 1 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 2 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 3 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 4 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 5 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 6 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 7 (2007).
Ono et al., "Differences in neurogenic potential in floor plate cells along an anteroposterior location: midbrain dopaminergic neurons originate from mesencephalic floor plate cells," Development, 134:3213-3225 Supplemental Fig. 8 (2007).

(56) References Cited

OTHER PUBLICATIONS

Papapetrou et al., "Stoichiometric and Temporal Requirements of Oct4, Sox2, Klf4, and c-Myc Expression for Efficient Human Ipse Induction and Differentiation," PNAS USA, 106(31):12759-12764 (2009).
Paterson et al., "Preclinical Studies of Fibroblast Growth Factor Receptor 3 as a Therapeutic Target in Multiple Myeloma," Br. J. Haematol., 124(5):595-603 (2004).
Patten et al., "Distinct modes of floor plate induction in the chick embryo," Development, 130:4809-4821 (2003).
Perrier et al., "Derivation of midbrain dopamine neurons from human embryonic stem cells," PNAS USA, 101:12543-12548 (2004).
Perrier et al., "Derivation of midbrain dopamine neurons from human embryonic stem cells," PNAS USA, 101:12543-12548 Supporting Materials, Methods, Supplemental Data, and Supporting Fig. 6 (2004).
Placantonakis et al., "BAC Transgenesis in Human Embryonic Stem Cells as a Novel Tool to Define the Human Neural Lineage," Stem Cells 27:521-532 (2009).
Placzek and Briscoe, "The Floor Plate: Multiple Cells, Multiple Signals," Nat. Rev. Neurosci., 6:230-240 (2005).
Placzek et al., "Induction of floor plate differentiation by contact-dependent, homeogenetic signals," Development, 117:205-218 (1993).
Placzek, "The role of the notochord and floor plate in inductive interactions," Curr Opin Genet Dev., 5:499-506 (1995).
Raymon et al., "Immortalized Human Dorsal Root Ganglion Cells Differentiate into Neurons with Nociceptive Properties," J. Neurosci. 19(13):5420-5428 (1999).
Reubinoff et al., "Neural progenitors from human embryonic stem cells," Nature Biotechnology, 19:1134-1140 (2001).
Roelink et al., "Floor plate and motor neuron induction by vhh-1, a vertebrate homolog of hedgehog expressed by the notochord," Cell, 76:761-775 (1994).
Saha et al., "Technical Challenges in Using Human Induced Pluripotent Stem Cells to Model Disease," Cell Stem Cell, 5(6):584-595 (2009).
Sasai et al., "Xenopus chordin: a Novel Dorsalizing Factor Activated by Organizer-Specific Homeobox Genes," Cell, 79(5):779-790 (1994).
Schlosser et al., "Development of Neurogenic Placodes in Xenopus laevis," The Journal of Comparative Neurology, 418:121-146 (2000).
Schlosser et al., "Induction and Specification of Cranial Placodes," Dev Biol., 294(2):303-351 (2006) A: pp. 303-327.
Schlosser et al., "Induction and Specification of Cranial Placodes," Dev Biol., 294(2):303-351 (2006) B: pp. 328-351.
Shen et al., "The timing of cortical neurogenesis is encoded within lineages of individual progenitor cells," Nat Neurosci., 9:743-751 (2006).
Shirasaki et al., "Guidance of cerebellofugal axons in the rat embryo: directed growth toward the floor plate and subsequent elongation along the longitudinal axis," Neuron, 14:961-972 (1995).
Smith et al., "Expression Cloning of noggin, a New Dorsalizing Factor Localized to the Spemann organizer in Xenopus Embryos," Cell, 70:829-840 (1992).
Smith et al., "Inhibition of Activin/Nodal signaling promotes specification of human embryonic stem cells into neuroectoderm," Dev Biol., 313:107-117 (2008).
Steinbeck et al., "Optogenetics enables functional analysis of human embryonic stem cell-derived grafts in a Parkinson's disease model," Nature Biotechnology, 33(2):204-209 (2015).
Stem Cells: Scientific Progress and Future Research Directions. Department of Health and Human Services. Jun. 2001. Chapter 4. pp. 23-42.
Streit, "Early development of the cranial sensory nervous system: from a common field to individual placodes," Dev Biol., 276:1-15 (2004).
Sukoyan et al., "Embryonic Stem Cells Derived from Morulae, Inner Cell Mass, and Blastocysts of Mink: Comparisons of Their Pluripotencies," Mol. Reprod. Dev., 36:148-158 (1993).

Sukoyan et al., "Isolation and Cultivation of Blastocyst-Derived Stem Cell Lines from American Mink (*Mustela vison*)," Mol. Reprod. Dev., 33:418-431 (1992).
Sumi et al., "Defining early lineage specification of human embryonic stem cells by the orchestrated balance of canonical Wnt/β-catenin, Activin/Nodal and BMP signaling," Development, 135:2969-2979 (2008).
Sun et al., "A Central Role for Islet1 in Sensory Neuron Development Linking Sensory and Spinal Gene Regulatory Programs," Nat Neurosci., 11(11):1283-1293 (2008).
Sun et al., "Design, Synthesis, and Evaluations of Substituted 3-[(3- or 4-Carboxyethylpyrrol-2-yl)Methylidenyl]indolin-2-ones as Inhibitors of VEGF, FGF, and PDGF Receptor Tyrosine Kinases," J Med Chem., 42(25):5120-5130 (1999).
Suter et al., "A Sox1 to Pax6 switch drives neuroectoderm to radial glia progression during differentiation of mouse embryonic stem cells," Stem Cells, 27(1):49-58 (2009).
Takahashi et al., "Induction of Pluripotent Stem Cells from Adult Human Fibroblasts by Defined Factors," Cell, 131:861-872 (2007).
Takahashi et al., "Induction of Pluripotent Stem Cells From Mouse Embryonic and Adult Fibroblast Cultures by Defined Factors," Cell, 126(4):663-676 (2006).
Tanaka et al., "FGF-Induced Vesicular Release of Sonic Hedgehog and Retinoic Acid in Leftward Nodal Flow is Critical for Left-Right Determination," Nature, 435(7039):172-177(2005).
Tesar et al., "New cell lines from mouse epiblast share defining features with human embryonic stem cells," Nature, 448:196-199 (2007).
Theos et al., "The Silver Locus Product Pmell 7/Gp100/Silv/Me20: Controversial in Name and in Function," Pigment Cell Res., 18(5):322-336 (2005).
Thomson et al., "Isolation of a primate embryonic stem cell line," PNAS, 92:7844-7848 (1995).
Tomishima et al., "Production of Green Fluorescent Protein Transgenic Embryonic Stem Cells Using the GENSAT Bacterial Artificial Chromosome Library," Stem Cells, 25(1):39-45 (2007).
Valenzuela et al., "Identification of Mammalian Noggin and Its Expression in the Adult Nervous System," J. Neurosci., 15(9):6077-6084 (1995).
Vallier et al., "Nodal Inhibits Differentiation of Human Embryonic Stem Cells Along the Neuroectodermal Default Pathway," Dev Biol., 275(2):403-421 (2004).
Venezia et al., "Molecular Signatures of Proliferation and Quiescence in Hematopoietic Stem Cells," PLoS Biol., 2(10):e301 (2004).
Vierbuchen et al., "Direct Conversion of Fibroblasts to Functional Neurons by Defined Factors," Nature, 463(7284):1035-1041 (2010).
Wang et al., "Noggin and bFGF cooperate to maintain the pluripotency of human embryonic stem cells in the absence of feeder layers," Biochem Biophys Res Commun., 330:934-942 (2005).
Wang et al., "Stem Cells from Human-Exfoliated Deciduous Teeth Can Differentiate into Dopaminergic Neuron-Like Cells," Stem Cells and Development, 19(9):1375-1383 (2010).
Watanabe et al., "A ROCK inhibitor permits survival of dissociated human embryonic stem cells," Nat. Biotechnol., 25(6):681-686 (2007).
Weinstein et al., "Neural Induction," Annu Rev Cell Dev Biol., 15:411-433, pp. 411-424 (1999a).
Weinstein et al., "Neural Induction," Annu Rev Cell Dev Biol., 15:411-433, pp. 425-433 (1999b).
Wichterle et al., "Directed Differentiation of Embryonic Stem Cells into Motor Neurons," Cell, 110:385-397 (2002).
Willert et al., "Wnt Proteins," CSH Perspectives in Biology, 4:1-13 (2012).
Woolf and Ma, "Nociceptors—Noxious Stimulus Detectors," Neuron, 55(3):353-364 (2007).
Written Opinion of the International Searching Authority dated Mar. 29, 2013 in International Patent Application No. PCT/US2012/063339.
Xu et al., "Basic FGF and suppression of BMP signaling sustain undifferentiated proliferation of human ES cells," Nat Methods, 2:185-190 (2005).
Xu et al., "BMP4 initiates human embryonic stem cell differentiation to trophoblast," Nat Biotechnol., 20(12):1261 (2002).

(56) References Cited

OTHER PUBLICATIONS

Xu et al., "NANOG is a Direct Target of TGFβ/Activin-Mediated SMAD Signaling in Human ESCs," Cell Stem Cell, 3:196-206 (2008).
Yamashita et al., "Bone Morphogenetic Protein Receptors," Bone, 19(6):569-574 (1996).
Yan et al., "Directed Differentiation of Dopaminergic Neuronal Subtypes from Human Embryonic Stem Cells," Stem Cells, 23(6):781-790 (2005).
Yu et al., "BMP type I receptor inhibition reduces heterotopic ossification," Nature Medicine 14(12):1363-1369 (2008).
Zhang and Zhang, "Differentiation of Neural Precursors and Dopaminergic Neurons from Human Embryonic Stem Cells," Methods Mal Biol., 584:355-366 (2010).
Zhang et al., "In vitro differentiation of transplantable neural precursors from human embryonic stem cells," Nature Biotechnology, 19:1129-1133 (2001).
Zhou et al., "High-Efficiency Induction of Neural Conversion in Human ESCs and Human Induced Pluripotent Stem Cells With A Single Chemical Inhibitor of Transforming Growth Factor Beta Superfamily Receptors," Stem Cells, 28(10):1741-1750 (2010).
Zhu et al., "Functional Smoothened is Required for Expression of Gli3 in Colorectal Carcinoma Cells," Cancer Letters, 207(2):205-214 (2004).
Zietlow et al., "The Survival of Neural Precursor Cell Grafts is Influenced by In Vitro Expansion," Journal of Anatomy, 207(3):227-240 (2005).
Zoltewicz et al., "oto is a homeotic locus with a role in anteroposterior development that is partially redundant with Lim1," Development, 126:5085-5095 (1999).
U.S. Appl. No. 14/168,835, Apr. 25, 2018 Non-Final Office Action.
U.S. Appl. No. 14/168,835, Apr. 16, 2018 Applicant Initiated Interview Summary.
U.S. Appl. No. 14/168,835, Apr. 16, 2018 Request for Continued Examination (RCE).
U.S. Appl. No. 14/168,835, Apr. 10, 2018 Advisory Action.
U.S. Appl. No. 14/168,835, Mar. 16, 2018 Response after Final Action.
U.S. Appl. No. 14/168,835, Jan. 17, 2018 Final Office Action.
U.S. Appl. No. 14/168,835, Nov. 16, 2017 Response to Non-Final Office Action.
U.S. Appl. No. 14/169,286, May 11, 2018 Response to Non-Final Office Action.
U.S. Appl. No. 14/169,286, Feb. 12, 2018 Non-Final Office Action.
U.S. Appl. No. 14/169,286, Dec. 4, 2017 Response to Non-Final Office Action.
U.S. Appl. No. 14/169,286, Sep. 6, 2017 Non-Final Office Action.
U.S. Appl. No. 14/169,286, Aug. 8, 2017 Response to Restriction Requirement.
U.S. Appl. No. 14/356,042, May 16, 2018 Non-Final Office Action.
U.S. Appl. No. 14/356,042, Mar. 19, 2018 Amendment and Request for Continued Examination (RCE).
U.S. Appl. No. 14/356,042, Mar. 14, 2018 Applicant Initiated Interview Summary.
U.S. Appl. No. 15/077,012, Mar. 22, 2018 Notice of Allowance.
U.S. Appl. No. 15/077,012, Jan. 16, 2018 Response to Restriction Requirement.
U.S. Appl. No. 15/077,012, Nov. 3, 2017 Restriction Requirement.
Andersson et al., "Identification of Intrinsic Determinants of Midbrain Dopamine Neurons," Cell 124:393-405 (2006).
Deng et al., "Specific and integrated roles of Lmx1a, Lmx1b and Phox2a in ventral midbrain development," Development 138:3399-3408 (2011).
NIH (Stem Cell: Scientific Progress and Future Research Directions, Department of Health and Human Services, Chapter 1, pp. 1-4, Jun. 2001.
Wang et al., "Identification of select glucocorticoids as Smoothened agonists: Potential utility for regenerative medicine," PNAS 107(20):9323-9328 (2010).
European Search Report dated Apr. 2, 2019 in EP Application No. 18198365.
Fujiwara et al., "Restoration of spatial memory dysfunction of human APP transgenic mice by transplantation of neuronal precursors derived from human iPS cells," Neuroscience Letters 557:129-134 (2013).
Ohyama et al., "Directed differentiation of neural cells to hypothalamic dopaminergic neurons," Development 132:5185-5197 (2005).
Chambers et al., "Highly efficient neural conversion of human ES and iPS cells by dual inhibition of SMAD signaling", Nature Biotechnology, 2009, vol. 27, No. 3, pp. 275-280.
Fasano et al., "Efficient Derivation of Functional Floor Plate Tissue from Human Embryonic Stem Cells", Cell Stem Cell, 2010, vol. 6, No. 4, pp. 336-347.
International search report dated Sep. 26, 2014 in International Application No. PCT/US2014/035760.
Letinic et al., "Origin of GABAergic neurons in the human neocortex", Nature, 2002, vol. 417, No. 6889, pp. 645-649.
Maroof et al., "Directed differentiation and functional maturation of cortical interneurons from human embryonic stem cells", Cell Stem Cell, Epub. May 2, 2013, vol. 12, No. 5, pp. 559-572.
Menendez et al., "Wnt signaling and a Smad pathway blockade direct the differentiation of human pluripotent stem cells to multipotent neural crest cells", PNAS, 2011, vol. 108, No. 48, pp. 19240-19245.
Watanabe et al., "Directed differentiation of telencephalic precursors from embryonic stem cells", Nature Neuroscience, 2005, vol. 8, No. 3, pp. 288-296.
Hester, et al., "Rapid and Efficient Generation of Functional Motor Neurons From Human Pluripotent Stem Cells Using Gene Delivered Transcription Factor Codes," Molecular Therapy 19:1905-1912 (2011).
Wataya et al., "Human Pluripotent stem cell and neural differentiation," Brain and Nerve 60:1165-1172 (2008) [English abstract].

* cited by examiner

FIGS. 6A-6D2
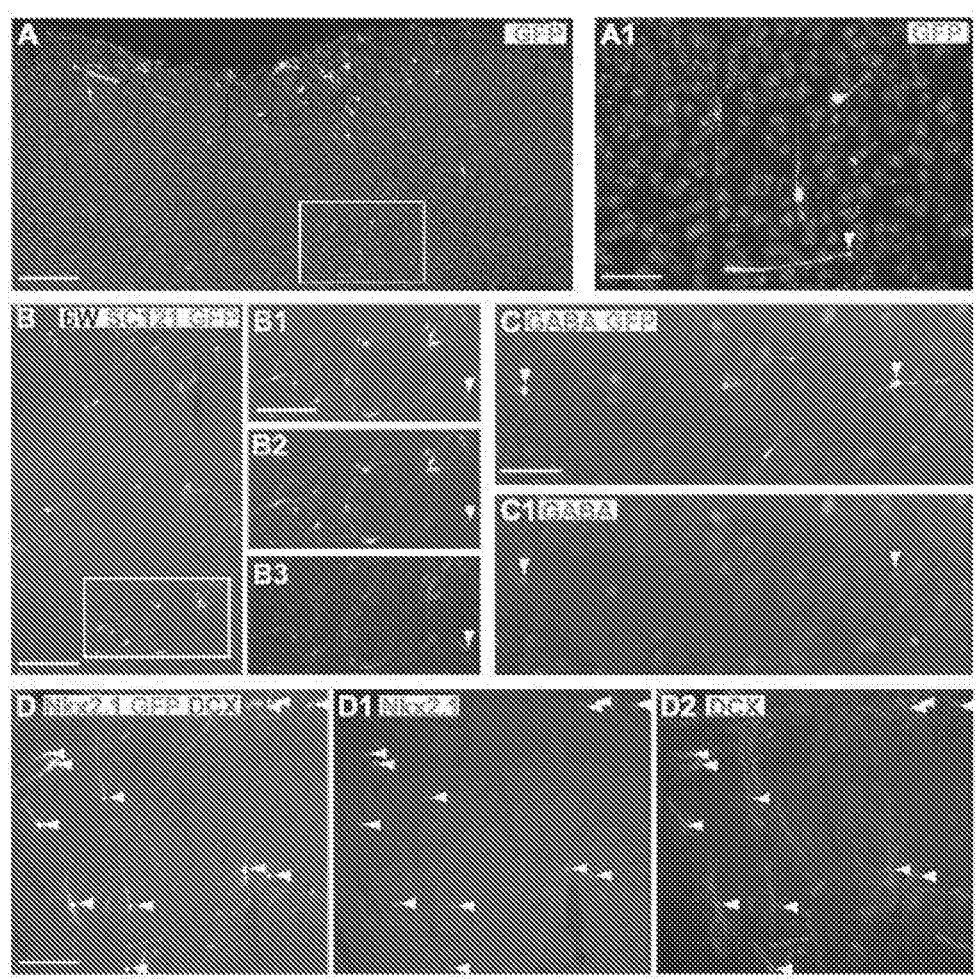

FIGS. 7A-7K
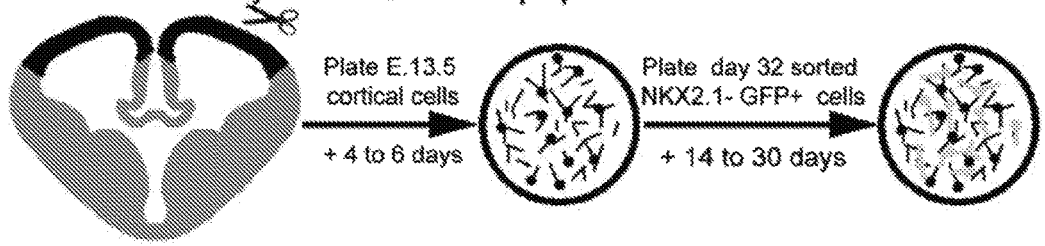
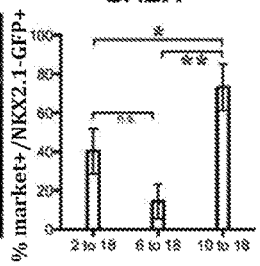 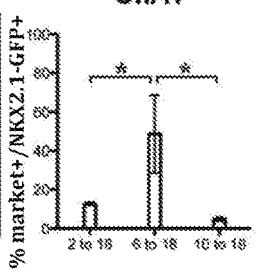
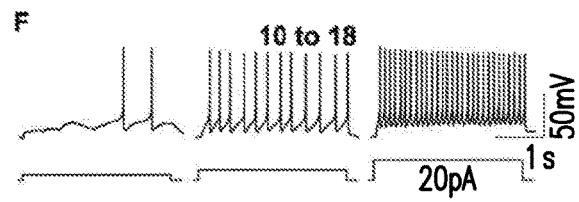
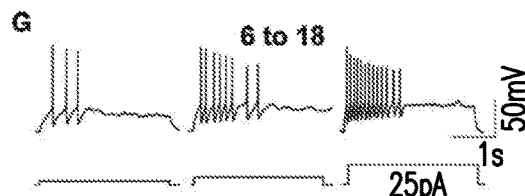
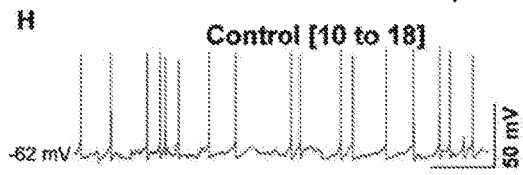
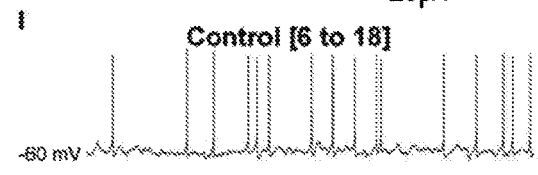
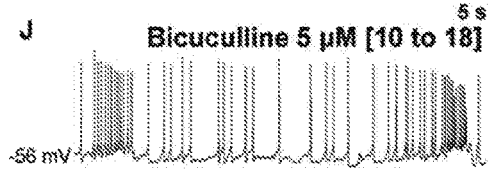
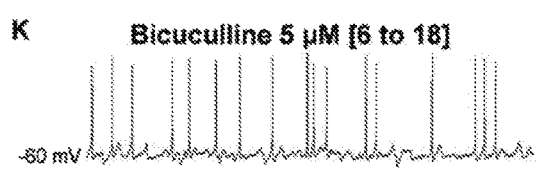

CORTICAL INTERNEURONS AND OTHER NEURONAL CELLS PRODUCED BY THE DIRECTED DIFFERENTIATION OF PLURIPOTENT AND MULTIPOTENT CELLS

CROSS-REFERENCE TO RELATED APPLICATIONS

This application is a continuation of International Application No. PCT/US14/035760, filed on Apr. 28, 2014, which claims the benefit of U.S. Provisional Patent Application No. 61/816,624, filed on Apr. 26, 2013, the contents of each of which are incorporated by reference in their entireties, and priority to each of which is claimed.

GOVERNMENT SPONSORED RESEARCH AND DEVELOPMENT

The work described in this disclosure was funded in part by the Grant Nos. 2RO1 MH066912 and 1RC1MH089690 from the National Institutes of Health. The U.S. government has certain rights in this disclosure.

BACKGROUND OF THE DISCLOSURE

Technical Field

The present disclosure relates, generally, to the in vitro differentiation of stem cells and neural progenitor cells, to the development of in vitro cell-based model systems for the study of disorders and diseases, and to the treatment of disorders and diseases by the administration of cells that are generated in vitro through the directed differentiation of neuronal cells. More specifically, the present disclosure provides in vitro methods for generating and compositions comprising neuronal cells and neuronal cell precursors including, for example, cortical interneurons, hypothalamic neurons, and pre-optic cholinergic neurons and precursor thereof. Such neuronal cells are generated by contacting multipotent, pluripotent, and/or totipotent cells, including stem cells, with inhibitors and/or antagonists of SMAD and Wnt signaling to generate neuronal cells and with activators of one or more SHH signaling pathway at a time and for a duration required to generate neuronal cells producing one or more markers of cortical interneurons, hypothalamic neurons, and/or pre-optic cholinergic neurons. The cortical interneurons, hypothalamic neurons, and pre-optic cholinergic neurons that are generated by the in vitro methods disclosed herein can be used therapeutically to treat neurodegenerative and neuropsychiatric disorders and diseases and can be used as model systems for the study of such neurodegenerative and neuropsychiatric disorders and diseases and for the screening and identification of therapeutic candidate compounds for the treatment of such disorders and diseases.

Description of the Related Art

The treatment of neurological disorders has traditionally included the in vivo administration of one or more small molecules. These therapeutic approaches have, unfortunately, resulted in very modest in vivo efficacy in patients afflicted with neurological disorders.

Neuronal tissues, most specifically neuronal tissues within the brain, exhibit synaptic plasticity and the capacity for remodeling. These properties have not, however, been satisfactorily exploited for the development of therapeutic regimen for neurological disorders. Primary human neurons are difficult to obtain from a live donor and, because mature neurons are post-mitotic, they cannot be cultured in vitro in the timeframe required to yield cell numbers required for achieving therapeutic benefit.

Totipotent, pluripotent, and multipotent cells, including stem cells, are powerful tools for studying disorders and disease and for the development of cell-based therapies for the treatment of disorders and disease, including neurological disorders and disease. Pluripotent cells, including pluripotent stem cells (PSCs) such as embryonic stem cells (ESCs) and induced pluripotent stem cells (iPSCs), can be differentiated towards cell lineages of the central nervous system (CNS).

It has, therefore, been suggested that CNS cells, which are generated in vitro from, for example, ESCs and/or iPSCs, may find use in therapeutic regimen for the treatment of disorders and disease, including neurodegenerative and neuropsychiatric disorders and disease. Protocols have been described for directing certain aspects of neuronal specification in vitro. For example, the neural conversion of human ESCs (hESCs) has been achieved by contacting adherent hESCs with two inhibitors of SMAD signaling—Noggin and SB431542 (an inhibitor of activin/nodal signaling). Chambers et al. *Nat Biotechnol* 27:275-280 (2009).

Early studies using hPSCs focused on neurodegenerative disorders that are associated with a specific subset of neuronal cells, such as midbrain dopamine neurons in Parkinson's disease (Kriks et al., *Nature* 480:547-551 (2011); Soldner et al., *Cell* 136:964-977 (2009); and Soldner et al., *Cell* 146:318-331 (2011)) or motor neurons in amyotrophic lateral sclerosis (Dimos et al., *Science* 321:1218-1221 (2008)) and spinal muscular atrophy (Ebert et al., *Nature* 457:277-280 (2009)).

Similar approaches have been suggested for other complex neuronal disorders such as schizophrenia (Brennand et al., *Nature* 473:221-225 (2011)) and the various autism-related syndromes (Marchetto et al., *Cell* 143:527-539 (2010) and Pasca et al., *Nat Med* 17:1657-1662 (2011)). Unlike Parkinson's disease (PD), amyotrophic lateral sclerosis (ALS), or spinal muscular atrophy (SMA), the specific subset of neurons that are associated with schizophrenia and autism-related syndromes remains poorly defined, which has hampered the development of therapeutic regimen for treating and model systems for studying those neuronal disorders.

Inhibitory neurons, such as cortical interneurons, may play a particularly important role in schizophrenia and autism. Insel, *Nature* 468:187-193 (2010) and Lewis et al., *Nat Rev Neurosci* 6:312-324 (2005). Protocols have recently been described for producing human cortical projection neurons from ESCs. Espuny-Camacho et al., *Neuron* 77:440-456 (2013) and Shi et al., *Nat Neurosci* 15:477-486 and S471 (2012).

Cortical interneurons and their precursors have an amazing ability to migrate, mature, and function after transplantation into adult cerebral cortex. Since these cells normally control cortical activity, it has been proposed to use them in a cell based therapy for chronic seizures of focal origin. Particularly in the case of intractable seizure disorders, cell-based therapy has been proposed as an alternative to surgical intervention. It is anticipated that such cells can also be used in cell-based therapy for forebrain disorders such as medication-intractable seizures and Parkinson's disease. Such therapy could be used either to harness the intrinsic ability of these cells to inhibit activity, or a drug delivery system after genetic manipulation to express therapeutic agents (i.e., agents that suppress seizures, including GABA, neuropeptide Y, adenosine).

Cortical interneurons and other neurons of the forebrain lineages, such as hypothalamic neurons or pre-optic cholinergic neurons and precursors thereof, are difficult to produce in vitro, but have great potential both therapeutically and as disease models. Hypothalamic neurons are predominantly involved in endocrine related disorders, sleep disorders (e.g., narcolepsy), and disorders that are related to abnormal food intake. Pre-optic cholinergic neurons perform a memory function, which is lost in Alzheimer's disease (AD). Transplantation of cortical interneurons and other neurons of the forebrain lineages, such as hypothalamic neurons and pre-optic cholinergic neurons has significant therapeutic potential for the treatment of endocrine, sleep, and food intake disorders and for the treatment of AD, respectively.

Murine cortical interneurons have been derived using an Lhx6::GFP reporter mouse ESC line, although the efficiency of cortical interneuron generation was low. Maroof et al., *J Neurosci* 30:4667-4675 (2010). The developmental origin of human cortical interneurons remains to be established and it has been reported that interneuron specification may differ across mammalian species. Letinic et al., *Nature* 417:645-649 (2002) and Yu and Zecevic, *J Neurosci* 31:2413-2420 (2011). Moreover, the protracted in vivo development of cortical interneurons has presented a challenge to achieving in vitro differentiation with human cells. It remains uncertain, therefore, whether the conditions described by Maroof et al. can be applied to the generation of human cortical interneurons from human ESCs and/or from other pluripotent stem cells.

SUMMARY OF THE DISCLOSURE

The present disclosure is based upon the discovery that forebrain differentiation can be enhanced and that certain neurons of the central nervous system (CNS), including cortical interneurons, hypothalamic neurons, and pre-optic cholinergic neurons and precursors thereof, can be efficiently induced in vitro by contacting certain totipotent, pluripotent and/or multipotent cells (e.g., human embryonic stem cells (hESCs) and/or human induced pluripotent stem cells (hiPSCs)) with one, two, or more inhibitors of the SMAD transcription factor in combination with one or more Wnt antagonists at a suitable concentration and for a suitable duration to generate neuronal precursor cells, which neuronal precursor cells can be contacted with one or more activator of SHH signaling at a suitable concentration, at a suitable time following initiation of stem cell differentiation and/or generation of neuronal cells, and for a suitable duration thereby inducing in the neuronal cells production of one or more markers of a cortical interneuron or precursor cell thereof, one or more markers of a hypothalamic neuron or precursor cell thereof, and/or one or more markers of a pre-optic cholinergic neuron or precursor cell thereof. In addition, cortical projection neurons and precursors thereof can be generated by a similar method lacking the step of contacting with an SHH activator.

Based upon these and other discoveries, which are described in detail herein, in certain embodiments, the present disclosure provides in vitro methods for generating neuronal cells, including neuronal cells comprising one or more markers of a cortical interneuron, a hypothalamic neuron, and/or a pre-optic cholinergic neuron. Also provided are neuronal cells, including cortical interneurons, hypothalamic neurons, and/or pre-optic cholinergic neurons as well as cortical projection neurons and precursors of any of the foregoing that are generated by the methods disclosed herein as well as compositions comprising one or more of such neuronal cells. Further, provided are compositions comprising one and preferably two or more SMAD inhibitors and one or more Wnt antagonists and compositions and formulations, including pharmaceutically appropriate compositions and formulations, comprising one or more activators of SHH signaling as well as kits comprising one, two, or more SMAD inhibitors, one or more Wnt antagonists, and one or more activators of SHH signaling, and optionally instructions for use to prepare one or more neurons of the foregoing type or precursors thereof.

Within certain embodiments, the present disclosure provides in vitro methods for generating neurons, including neurons comprising one or more markers of a cortical interneuron or a cortical interneuron precursor, wherein the methods comprise the differentiation of a totipotent cell, a pluripotent cell, or a multipotent cell by: (a) contacting a totipotent cell, a pluripotent cell, and/or a multipotent cell with one, two, or more inhibitors of SMAD and with one or more antagonists of Wnt signaling, thereby inducing the generation of a neuronal precursor cell from the totipotent, pluripotent, and/or multipotent cell; (b) contacting the neuronal precursor cell with one or more activator of SHH signaling, thereby inducing in the neuronal precursor cell the production of one or more markers of a cortical interneuron and/or of a cortical interneuron precursor cell.

Within certain aspects of these methods, the neuronal precursor cell producing the one or more markers of a cortical interneuron and/or of a cortical interneuron precursor cell is subjected to conditions favoring neuronal precursor cell maturation. Within other aspects, the neuronal precursor cell in contacted with the one or more activator of SHH signaling after the passage of a predetermined period of time following the generation of the neuronal precursor cell and/or following the contacting of the totipotent, pluripotent, and/or multipotent cell with the one, two, or more inhibitors of SMAD and/or the one or more antagonists of Wnt signaling.

Within related aspects of these methods contacting the neuronal precursor cell with one or more activator of SHH signaling is initiated from about 4 days to about 20 days or from about 6 days to about 20 days, or from about 8 days to about 20 days, or from about 8 days to about 18 days after contacting a totipotent cell, a pluripotent cell and/or a multipotent cell with one, two, or more inhibitors of SMAD and with one or more antagonists of Wnt signaling to make a cortical interneuron or a cortical interneuron precursor.

Contacting the neuronal precursor cell with one or more activator of SHH signaling can be for a time period of from about 5 days to about 30 days or from about 8 days to about 16 days. The time of contacting a neuronal cell with an activator of SHH can be determined by the culture medium in which contacting with the one or more SHH activator is carried out. The culture medium can, for example, comprise essential 6 medium and KSR-based medium among others as disclosed above. In practice the SHH activator need not to be withdrawn (e.g. by media change) and the cells can be grown in culture for several weeks or several months.

In particular, the cortical interneurons and/or precursors thereof can be maintained in culture for several weeks to several months. The cortical interneurons and/or precursors thereof can be maintained in culture or in vivo for many months.

Within further aspects of these methods each of the one or more markers of a cortical interneuron and/or of a cortical interneuron precursor cell can be selected from the group consisting of SST, PV, GABA, calbindin, LHX6, RAX, FOXA2, FOXG1, OLIG2, MASH 1, NKX6.2, VGLUT1, MAP2, CTIP2, SATB2, TBR1, DLX2, ASCL1, and ChAT and combinations thereof.

Within other embodiments, the present disclosure provides in vitro methods for generating a neuronal cell producing one or more markers of a hypothalamic neuron and/or of a hypothalamic neuron precursor cell, wherein the neuronal cell is generated by differentiation of a totipotent cell, a pluripotent cell, and/or a multipotent cell, the method comprising: (a) contacting one or more totipotent cells, one or more pluripotent cells, and/or one or more multipotent cells with (i) one, two, or more inhibitors of SMAD and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a hypothalamic neuron and/or of a hypothalamic neuron precursor cell.

Within certain aspects of these methods, the neuronal precursor cell producing the one or more markers of a hypothalamic neuron and/or of a hypothalamic neuron precursor cell is subjected to conditions favoring neuronal precursor cell maturation. Within other aspects, the neuronal precursor cell is contacted with the one or more activator of SHH signaling after the passage of a predetermined period of time following generation of the neuronal precursor cell and/or following the contacting of the totipotent, pluripotent, and/or multipotent cell with the one, two, or more inhibitors of SMAD and/or the one or more antagonists of Wnt signaling. In some other embodiments, a cortical feeder environment was created using embryonic mouse cortical cells to accelerate the maturation of neuronal cells in vitro.

Within other aspects of these methods contacting the neuronal precursor cell with one or more activator of SHH signaling is initiated from about 1 day to about 4 days after contacting a totipotent cell, a pluripotent cell, and/or a multipotent cell with one, two, or more inhibitors of SMAD and with one or more antagonists of Wnt signaling, to produce a hypothalamic neuron or hypothalamic neuron precursor cell. Contacting the neuronal precursor cell with one or more activator of SHH signaling can be for a time period of from about 5 days to about 30 days or from about 8 days to about 20 days. Longer contact with SHH activator is not harmful.

Within further aspects of these methods each of the one or more markers of a hypothalamic neuron and/or of a hypothalamic neuron precursor cell can be selected from the group consisting of NGFI-B, c-fos, CRF, tyrosine hydroxylase (TH), RAX, POMC, hypocretin, vasopressin, oxytocin, nNOS and NADPH and combinations thereof.

Within yet other embodiments, the present disclosure provides in vitro methods for generating a neuronal cell producing one or more markers of a pre-optic cholinergic neuron and/or of a pre-optic cholinergic neuron precursor cell, wherein the neuronal cell is generated by differentiation of a totipotent cell, a pluripotent cell, and/or of a multipotent cell, the method comprising: (a) contacting one or more totipotent cells, one or more pluripotent cells, and/or one or more multipotent cells with (i) one, two, or more inhibitors of SMAD and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a pre-optic cholinergic neuron and/or of a pre-optic cholinergic neuron precursor cell.

Within certain aspects of these methods, the neuronal precursor cell producing the one or more markers of a pre-optic cholinergic neuron and/or of a pre-optic cholinergic neuron precursor cell is subjected to conditions favoring neuronal precursor cell maturation. Within other aspects, the neuronal precursor cell is contacted with the one or more activator of SHH signaling after the passage of a predetermined period of time following generation of the neuronal precursor cell and/or following the contacting of the totipotent, pluripotent, and/or multipotent cell with the one, two, or more inhibitors of SMAD and/or the one or more antagonists of Wnt signaling.

Within other aspects of these methods contacting the neuronal precursor cell with one or more activator of SHH signaling is initiated from about 4 days to about 8 days after contacting a totipotent cell, a pluripotent cell, and/or a multipotent cell with one or more inhibitors of SMAD and with one or more antagonists of Wnt signaling to produce a pre-optic cholinergic neuron or a pre-optic cholinergic neuron precursor. Contacting the neuronal precursor cell with one or more activator of SHH signaling can be for a time period of from about 5 days to about 30 days or from about 8 days to about 24 days.

Within further aspects of these methods each of the one or more markers of a pre-optic cholinergic neuron and/or of a pre-optic cholinergic neuron precursor cell can be selected from the group consisting of ChAT, NGF, Ach, VAChT, LHX8, ISL1, and p75 and combinations thereof.

Within other aspects of the methods according to any of these three embodiments, one or more totipotent cells, pluripotent cells, and/or multipotent cells are human cells or are murine cells. Within yet other aspects of the methods according to any of these three embodiments, the one or more totipotent cells, pluripotent cells, and/or multipotent cells can be selected from the group consisting of embryonic stem cells, adult stem cells, neural stem cells, induced pluripotent cells, engineered pluripotent cells, primary progenitor cells, induced progenitor cells, and engineered progenitor cells.

Within further aspects of the methods according to any of these three embodiments, contacting with SMAD inhibitors and/or contacting with Wnt signaling antagonists can be carried out simultaneously or can be carried out sequentially. Contacting can be for a duration of from about 5 days to about 30 days. Within related aspects of these methods, contacting with one or more Wnt antagonists can be initiated from 0 day to about 5 days or from 0 day to about 1 day after contacting the totipotent, pluripotent, and/or multipotent cell with one, two, or more inhibitors of SMAD signalling and/or one or more antagonists of a Wnt signaling pathway.

Within still further aspects of the methods according to any of these three embodiments, SMAD inhibitors can be selected from the group consisting of SB431542, LDN-193189, Noggin PD169316, SB203580, LY364947, A77-01, A-83-01, BMP4, GW788388, GW6604, SB-505124, lerdelimumab, metelimumab, GC-I008, AP-12009, AP-11OI4, LY550410, LY580276, LY364947, LY2109761, SB-505124, E-616452 (RepSox ALK inhibitor), SD-208, SMI6, NPC-30345, Ki26894, SB-203580, SD-093, activin-M108A, P144, soluble TBR2-Fc, DMH-1, Dorsomorphin dihydrochloride, and a derivative and/or variant thereof, wherein each derivative and/or variant thereof possesses one or more SMAD inhibitory activities, wherein each derivative and/or variant thereof possesses one or more SMAD inhibitory activities. For example, two or more SMAD signaling inhibitors can comprise the dual-SMAD inhibitors SB431542 and LDN-193189, or functional derivatives and/or variants thereof. SB431542 can be contacted with the totipotent, pluripotent, and/or multipotent cell at a final concentration in an in vitro culture of from about 0.1 µM to about 1 mM, or from about 0.1 µM to about 100. LDN-193189 can be contacted with the totipotent, pluripotent and/or multipotent cell at a final concentration in an in vitro culture of from about 1 nM to about 10 µM or from about 1 nM to about 1 µM.

Within yet further aspects of the methods according to any of these three embodiments, Wnt signaling antagonists can be at least one selected from the group consisting of XAV939, DKK1, SFRP-1, SFRP-2, SFRP-5, SFRP-3, SFRP-4, WIF-1, Soggy, IWP-2, IWR1, ICG-001, KY0211, Wnt-059, LGK974, IWP-L6, and a derivative and/or variant thereof, wherein each derivative and/or variant thereof possesses one or more Wnt signaling antagonist activities. For example, the Wnt signaling antagonist can comprise XAV939 or a functional derivative and/or variant thereof. XAV939 can be contacted with the pluripotent and/or multipotent cell at a final concentration in an in vitro culture of from about 10 nM to about 500 µM or from about 0.2 µM to about 200 µM.

Within still further aspects of the methods according to any of these three embodiments, SHH signaling activators can be selected from the group consisting of Smoothened agonist (SAG), SAG analog, SHH, C25-SHH, C24-SHH, purmorphamine, Hg—Ag and a derivative and/or variant thereof, wherein each derivative and/or variant thereof possesses one or more SHH signaling activator activities. For example, the SHH signaling activator can comprise recombinant SHH and/or purmorphamine, or functional derivatives and/or variants thereof. Recombinant SHH can be contacted with the totipotent, pluripotent, and/or multipotent cell at a final concentration in an in vitro culture of from about 5 ng/mL to about 5 µg/mL. Purmorphamine can be contacted with the pluripotent and/or multipotent cell at a final concentration in an in vitro culture of from about 0.1 µM to about 20 µM.

Within still further aspects of the methods according to any of these three embodiments, the neuronal precursor cells comprise one or more markers selected from the group consisting of NKX2.1, NKX2.2, LHX6, LHX8, FOXA2, DLX1, DLX2, DLX5, DLX6, SIX6, SIX3, SOX6, MAFB, NPAS1, ASCL1, SIX6, OLIG2, and NKX6.2.

Within still further aspects of the methods according to any of these three embodiments, contacting with one, two, or more inhibitors of SMAD; one or more antagonists of Wnt signaling; and/or one or more activators of SHH signaling can be carried out in the presence of a feeder cell, such as a mouse cortical pyramidal neuron, for example a mouse cortical pyramidal neuron that is derived from a mouse ESC.

Within further embodiments, the present disclosure provides compositions comprising one or more in vitro differentiated neuronal cells that produce one or more markers of a cortical interneuronal cell and/or of a cortical interneuron precursor cell, wherein the in vitro differentiated neuronal cells are produced by: (a) contacting a multipotent cell, a pluripotent cell, and/or a totipotent cell with one, two, or more inhibitors of SMAD signaling, (b) contacting the multipotent cell, pluripotent cell, and/or totipotent cell with one or more inhibitors of Wnt signaling, and (c) contacting a neural progenitor cell generated from the multipotent cell, pluripotent cell, and/or totipotent cell with one or more activators of SHH signaling.

Within certain aspects of these embodiments, the composition comprises a mixture of two or more cells wherein cortical interneurons comprise at least about 30% of the total number of cells, or at least about 40% of the total number of cells, or at least about 50% of the total number of cells, or at least about 60% of the total number of cells, or at least about 70% of the total number of cells, or at least about 80% of the total number of cells, or at least about 90% of the total number of cells, or at least about 95% of the total number of cells.

Within related aspects of these embodiments, the composition comprises a mixture of two or more cells wherein NKX2.1+/PV+ cortical interneurons comprise at least about 5%, or at least about 10%, or at least about 20%, or at least about 30%, or at least about 40%, or at least about 50% of the total number of cells in the composition.

Within other related aspects of these embodiments, the composition comprises a mixture of two or more cells wherein γ-aminobutyric acid (GABA)-ergic inhibitory interneurons comprise at least about 5%, or at least about 10%, or at least about 20%, or at least about 30%, or at least about 40%, or at least about 50% of the total number of cortical interneurons in the composition.

Within certain aspects of these compositions, the cortical interneurons and/or interneuron precursor cells can comprise a transgene expressing a detectable marker such as, for example, CT-2 or green fluorescence protein (GFP).

Within still further embodiments, the present disclosure provides compositions comprising one or more in vitro differentiated neuronal cells that produce one or more markers of a hypothalamic neuron or a hypothalamic neuron precursor cell, wherein the in vitro differentiated neuronal cells are produced by: (a) contacting multipotent cell, a pluripotent cell, and/or a totipotent cell with two or more inhibitors of SMAD signaling, (b) contacting the multipotent cell, the pluripotent cell, and/or the totipotent cell with one or more inhibitors of Wnt signaling, and (c) contacting a neuronal progenitor cell generated from the multipotent cell, the pluripotent cell, and/or the totipotent cell with one or more activators of SHH signaling.

Within certain aspects of these embodiments, the composition comprises a mixture of two or more cells wherein hypothalamic neurons comprise at least about 30% of the total number of cells, or at least about 40% of the total number of cells, or at least about 50% of the total number of cells, or at least about 60% of the total number of cells, or at least about 70% of the total number of cells, or at least about 80% of the total number of cells, or at least about 90% of the total number of cells, or at least about 95% of the total number of cells.

Within yet other embodiments, the present disclosure provides compositions comprising one or more in vitro differentiated neuronal cells that produce one or more markers of a pre-optic cholinergic neuron or a pre-optic cholinergic neuron precursor cell, wherein the in vitro differentiated neuronal cells are produced by: (a) contacting a multipotent cell or a pluripotent cell with two or more inhibitors of SMAD signaling, (b) contacting the multipotent cell or a pluripotent cell with one or more inhibitors of Wnt signaling, and (c) contacting a neuronal precursor cell generated from the multipotent cell, the pluripotent cell, and/or the totipotent cell with one or more activators of SHH signaling.

Within certain aspects of these embodiments, the composition comprises a mixture of two or more cells wherein pre-optic cholinergic neurons comprise at least about 30% of the total number of cells, or at least about 40% of the total number of cells, or at least about 50% of the total number of cells, or at least about 60% of the total number of cells, or at least about 70% of the total number of cells, or at least about 80% of the total number of cells, or at least about 90% of the total number of cells, or at least about 95% of the total number of cells.

Within other aspects of the compositions of the three embodiments, the cells can be human or murine.

Within certain embodiments, the present disclosure provides an in vitro method for generating neurons through differentiation of human pluripotent or multipotent cells, said neurons comprising one or more markers indicating a forebrain precursor cell, the method comprising:
  a. contacting one or more starting cells selected from the group consisting of pluripotent cells, multipotent cells, and mixtures thereof with at least two inhibitors of SMAD and with at least one Wnt signaling antagonist to favor generation of said forebrain precursors from said pluripotent or multipotent cells or mixtures thereof; and
  b. optionally subjecting said generated forebrain precursors to conditions favoring their further differentiation.

The SMAD inhibitors and Wnt antagonists are as described above.

Within other embodiments, the present disclosure provides: (1) cell based methods for identifying and characterizing inhibitors and/or antagonists of SMAD and/or Wnt signaling and/or activators of SHH signaling; (2) compositions comprising combinations of inhibitors and/or antagonists of SMAD and/or Wnt signaling and/or activators of SHH signaling; and (3) methods for the treatment of neurological disorders and diseases, including neurodegenerative disorders and diseases, such as Parkinson's disease, Alzheimer's disease, ALS, multiple system atrophy, and neuropsychiatric disorders and diseases, such as schizophrenia and autism related disorders, which methods comprise the in vivo administration to a patient of cortical interneurons, hypothalamic neurons, and/or pre-optic cholinergic neurons generated by the in vitro methods disclosed herein.

These and other aspects of the present disclosure will be best understood in conjunction with the following drawings, which exemplify certain aspects of the various embodiments.

BRIEF DESCRIPTION OF THE DRAWINGS

FIGS. 1B, 1C, 1F, 1G, and 1H presents data derived from hESC line HES-3 (NKX2.1::GFP; FIG. 1D presents data from hESC line WA-09/H9; and FIG. 1E presents data from hESC line WA-09/H9 and hiPSC cell lines SeV6 and C72. In total, these data demonstrate that Wnt inhibition and activation of SHH signaling yields highly efficient derivation of forebrain fates and NKX2.1 induction. P: purmorphamine, S: Sonic hedgehog. FIGS. 1B and 1C are bar graphs showing that the addition of either DKK1 or XAV939 (Wnt signaling antagonists) to the dual SMAD inhibition protocol resulted in a significant increase in the percentage of FOXG1+ cells (FIG. 1B) but did not result in a loss of PAX6 expression (FIG. 1C).  p<0.01; * P<0.001; using ANOVA followed by Scheffe test. FIG. 1D is an immunofluorescence image for FOXG 1 and PAX6 expression on differentiation day 10 (XLSB induction). FIG. 1E is a bar graph showing that XLSB induces a robust telencephalic specification at comparable efficiencies in human pluripotent stem cells (hiPSC lines SeV6, C72; n=4). Scale bar in (B) represents 125 /lm. FIG. 1F is a bar graph showing that a combination of SHH with XLSB significantly enhanced the production of NKX2.1::GFP expressing progenitors. FIG. 1G is a bar graph showing that 1 µM purmorphamine added to 5 nM SHH beginning at differentiation day 4 (Sonic C24II) exhibited a synergistic elevation of NKX2.1::GFP expression at differentiation day 10 as compared to SHH (* P<0.001). A range of concentrations of SHH and purmorphamine were compared at differentiation day 18. Cotreatment was greatly superior to quite high concentrations of either SHH or purmorphamine alone as compared to no SHH using ANOVA followed by Scheffe test (* p<0.001). FIG. 1H is a bar graph showing that delaying the timing of initial SHH induction to begin between differentiation days 2-10 did not dramatically affect the synergy of purmorphamine efficiency of NKX2.1::GFP induction measured at differentiation day 18 as compared to cells at differentiation days 0-18 without SHH or purmorphamine, using ANOVA followed by Scheffe test (*** P<0.001).

FIG. 2A is a model of human prosencephalon (sagittal view at Carnegie stage 14 (CS 14)) with expression of forebrain patterning markers based on published data. Kerwin et al., *J Anat* 217:289-299 (2010). FIGS. 2B-2E are coronal (oblique) hemisections of the human prosencephalon at Carnegie stage 15 (CS15), which show production of NKX2.1, OLIG2, and PAX6. NKX2.1 and OLIG2 were produced in various regions throughout the ventral prosencephalon, whereas PAX6 production was restricted to the dorsal prosencephalon and the eye. The production of these proteins was non-overlapping, except in the ganglionic eminence (FIG. 2C) where OLIG2 and NKX2.1 were co-expressed. The scale bar in FIG. 2B represents 200/Lm. FIG. 2F is a schematic representation of the distinct time periods of SHH and purmorphamine treatment used in combination with the XLSB protocol. FIG. 2G is an immunofluorescence image for OL1G2 and FOXG1 in NKX2.1::GFP line in the differentiation day 6-18 SHH treatment group (micrograph column 2) and the differentiation day 10-18 SHH treatment group (micrograph column 3) where a significantly increased percentage of NKX2.1::GFP+ cells that coexpress FOXG1 was measured at differentiation day 18, as compared to the differentiation day 2-18 SHH treatment group (micrograph column 1). The differentiation day 10-18 SHH treatment group also demonstrated an enhanced derivation of NKX2.1::GFP+ cells co-expressing OLIG2, as compared to the differentiation day 2-18 SHH treatment group (* p<0.05, *** P<0.001 using ANOVA followed by Scheffe test). Expression of FOXG1, NKX2.1, and OLIG2 evidenced a pattern characteristic of ganglionic eminence. Tekki-Kessaris et al., *Development* 128:2545-2554 (2001). These immunofluorescence data were quantified and are presented in the bar graph of FIG. 2H. FIG. 2I is microarray gene expression data from cells sorted for NKX2.1::GFP expression at differentiation day 18 comparing the differentiation day 10-18 SHH treatment group versus the no SHH group (e.g., control). FIG. 2J is microarray gene expression data from cells sorted for NKX2.1::GFP expression at differentiation day 18 comparing the differentiation day 10-18 SHH treatment group versus the differentiation day 2-18 SHH treatment group. FIG. 2K is microarray gene expression data from cells sorted for NKX2.1::GFP expression at differentiation day 18 comparing the differentiation day 10-18 SHH treatment group versus the differentiation day 6-18 SHH treatment group. Indicated are genes expressed at higher levels in the differentiation day 10-18 SHH treatment group and genes expressed at lower levels in the differentiation day 10-18 SHH treatment group. All changes are significant at p<0.001.

FIG. 3A is a time course of FOXA2 expression after sorting differentiated NKX2.1::GFP expressing cells at differentiation day 18, then culturing the cells in the absence of SHH for two additional weeks. The percentage of FOXA2 co-labeling decreases over the course of two weeks. FIG. 3B is a representative immunocytochemistry image of the differentiation day 10-18 SHH treated group. Expression of FOXG1 and co-expression of FOXA2 and GFP at differentiation day 18. FIG. 3C is an embryonic day 11.5 coronal section of a developing mouse brain showing the expression of FOXG1, NKX2.1, and FOXA2 (D'Amato et al., *Proc Natl Acad Sci USA* 84:4322-4326 (1987)). There is no expression of FOXG1 in the diencephalon (Di) and there is no FOXA2 expression in the telencephalon (Tel). NKX2.1 is expressed in the medial ganglionic eminence (MGE) and the hypothalamus (HYPO), but is not expressed in the floor plate (FP) and does not co-label with FOXA2. FIG. 3D is a Carnegie stage 15 (CS15; approximately 5.5 gestational weeks) human embryo sectioned for immunohistochemical analysis. FIGS. 3E and 3F are adjacent coronal (oblique) hemisections of the human S15 prosencephalon demonstrating the expression of FOXA2 and NKX2.1. While FOXA2 appears to be specifically expressed in the ganglionic eminence (FIG. 3E) NKX2.1 is expressed in various regions of the ventral prosencephalon (FIG. 3F). FIGS. 3E and 3F demonstrate differences in FOXA2 expression between human and mouse, suggestive of an alternative mechanism to generate NKX2.1 progenitors in the ventral forebrain. However, FOXA2 expression in these NKX2.1 cells may be transient as shown in vitro (FIG. 3A) and as suggested by an in situ hybridization analyses of later stage human embryos (Allen Brain Atlas, human.brain-map.org).

FIGS. 4A-4C shows that at differentiation day 18 cells from the above three SHH treatment groups were subjected to FACS for NKX2.1::GFP expression, replated and evaluated for co-labeling with markers indicated. For all three groups there was a decline in co-labeling with markers of progenitors (upper panels: nestin; Ki67), and an increase in markers of neuronal differentiation (lower panels: GABA; TUn; doublecortin (DCX); calbindin). FIG. 4D is a Western blot showing an increase in the hypothalamic-enriched protein RAX in the differentiation day 2-18 SHH treatment group, and an increase in the medial ganglionic eminence (MGE)-enriched protein LHX6 in the differentiation day 10-18 SHH treatment group. Cells were sorted for NKX2.1::GFP prior to analysis. FIGS. 4E-4G shows that at differentiation day 32, many of the NKX2.1::GFP+ cells from the differentiation day 10-18 SHH treatment group also expressed DLX2 and ASCL1. FIGS. 4H-4N show exemplary data of grafting of differentiation day 32-sorted NKX2.1::GFP+ cells into the MGE of E13.5 coronal mouse slice cultures. FIG. 4H is a schematic of coronal hemisection demonstrating the site of transplantation and the zones for quantification of migration. FIGS. 4I and 4J show that, in both the differentiation day 2-18 SHH treatment group and the differentiation day 6-18 SHH treatment group, very few cells migrated into zone 1 and fewer into zone 2. FIGS. 4K and 4L show that the differentiation day 10-18 SHH treatment group demonstrated a significant and robust migration into the cortical and striatal regions, with many GFP+ cells exhibiting bipolar morphologies consistent with a migratory cell (FIG. 4L). FIGS. 4M-4N show regions of the differentiation day 10-18 SHH treatment group where GFP+ cells were detected and quantified. FIG. 4M: two days post transplantation DPT (* P<0.05; ** P<0.01 using ANOVA followed by Scheffe test). FIG. 4N: six days post transplantation DPT (* p<0.05; ** p<0.01 using ANOVA followed by Scheffe test). FIGS. 4O and 4P shows transplantation of day 32 sorted NKX2.1::GFP+ cells from the differentiation day 10-18 SHH treatment group into the neocortex of neonatal mice. Fixed sections were evaluated at postnatal day 30. In marked contrast to the MGE-like cells from the differentiation day 10-18 SHH treatment group (FIG. 4P), neither the differentiation day 2-18 SHH treatment group (FIG. 4O) nor the differentiation day 6-18 SHH treatment group (data not shown) resulted in extensive migration from the graft site.

FIG. 6A-6D2 presents exemplary data showing a slow pace of differentiation by NKX2.1-GFP+ cells following transplantation into neonatal mouse neocortex. Shown are examples of transplants of the NKX2.1-GFP line on differentiation day 32 from the differentiation day 10-18 SHH treatment group (e.g., the "MGE-like protocol). The cells had 15 been subjected to FACS for GFP determination and then transplanted into the neonatal neocortex of genetically immunocompromised mice, and evaluated in fixed sections after 6 weeks. FIG. 6A is a low magnification view of GFP immunofluorescence labeling. Scale bar=100 µm. The boxed area shows three cells at higher magnification in FIG. 6A1. Note that even after 6 weeks of differentiation in vivo most of these cells continue to have relatively undifferentiated appearance with bipolar or unipolar processes, often tipped by growth cones (arrow). Scale bar=20 µm. FIG. 6B are immunofluorescence images for the human specific cell marker SC121 and GFP (FIG. 6B (SC121/GFP), FIG. 6B1 (GFP), FIG. 6B2 (SC121)). All GFP+ cells express SC121, and most but not quite all SC121 cells at this age express GFP (see arrows). Similar low percentages of SC 121+/GFP− cells are also seen two weeks after transplantation (data not shown). Scale bar=35 µm, FIGS. 6B1-B3 scale bar=40 µm. FIGS. 6C and 6C1 show the same view of a section with immunofluorescence for GABA (red) and GFP (green). Two strongly co-labeled cells are indicated by the arrows. As GABA immunodetection penetrates poorly into sections, co-labeling was quantified by selectively counting only those GFP+ cells with cell bodies located within 5 microns of the cut edges of the section. By this approach, 46 of 51 cells (90.2%) from two 6-week transplants were strongly co-labeled. Scale bar=40 µm. FIG. 6D is an immunofluorescence image for GFP NKX2.1 and the marker of neuronal precursors DCX; pseudocolored Cy5 signal). All the GFP+ cells have NKX2.1-expressing nuclei (arrows), and also co-label for DCX. Scale bar=40 µm.

FIG. 7A-7K presents exemplary data showing maturation of NKX2.1+ cells into physiologically active neurons. FIG. 7A shows the preparation of cortical excitatory neuron cultures from embryonic day 13.5 (E13.5) mice, onto which FACS sorted human NKX2.1::GFP+ cells at differentiation day 32 are plated. FIGS. 7B-7E show that after 30 days in vitro (DIY), cultures from the differentiation day 10-18 SHH treated group were enriched for NKX2.1::GFP+ cells that co-express GABA (FIG. 7B, quantified in FIG. 7C; * p<0.05; ** P<0.01 using ANOVA followed by Scheffe test). In contrast, the differentiation day 6-18 SHH treated group was enriched for NKX2.1::GFP co-labeling with choline acetyltransferase (ChAT) (FIG. 7D, quantified in FIG. 7E; * P<0.05 using ANOV A followed by Scheffe test). FIG. 7F shows spiking patterns of differentiation day 10-18 SHH treated group neurons recorded at 28 DIV. Action potentials were initiated by protocols shown at bottom. FIG. 7G shows spiking patterns of differentiation day 6-18 SHH treated group neurons recorded at 28 DIV. Action potentials were initiated by protocols shown at bottom. FIG. 7H shows spontaneous spiking recorded from cultures enriched for GABAergic neurons (differentiated day 10-18 SHH treated group) in the absence of the $GABA_A$ receptor antagonist bicuculline. FIG. 7I shows spontaneous spiking recorded from cultures enriched for cholinergic neurons (differentiated days 6-18 SHH treated group) in the absence the GABAA receptor antagonist bicuculline. FIG. 7J shows spontaneous spiking recorded from cultures enriched for GABAergic neurons (differentiated day 10-18 SHH treated group) in the presence of the $GABA_A$ receptor antagonist bicuculline. FIG. 7K shows spontaneous spiking recorded from cultures enriched for cholinergic neurons (differentiated days 6-18 SHH treated group) in the presence of the GABAA receptor antagonist bicuculline. Bicuculline had little effect on the spontaneous firing activity in the differentiation day 6-18 SHH treatment group, consistent with the lack of GABAergic cells from either the mouse feeder or the human NKX2.1::GFP+ cells generated by this protocol.

FIGS. 8A-8E show collapsed z-stack confocal image showing NKX2.1::GFP+, vesicular GABA transporter (VGAT; FIG. 8A), and the post-synaptic GABAergic marker gephyrin (FIG. 8A). The dendrites of this GFP+ cell that co-label with gephyrin are receiving VGAT expressing pre-synaptic terminals (arrows). In addition, a GFP+ axonal process formed a VGAT+ pre-synaptic terminal adjacent to a GFP negative, gephyrin-expressing post-synaptic process (asterisk). FIG. 8F shows whole-cell patch clamp reveals spontaneous inhibitory post-synaptic currents (sIPSCs) recorded from differentiation day 10-18 SHH treatment group NKX2.1::GFP+ neurons, which are reversibly blocked by the addition of the $GABA_A$ receptor antagonist bicuculline. FIGS. 8G-8K show collapsed z-stack confocal image showing NKX2.1::GFP, vesicular glutamate transporter 1 (VGLUT1; FIG. 8G), and the post-synaptic marker PSD-95 (FIG. 8G). This GFP+ cell has dendrites that co-label with PSD-95 that are adjacent to VGLUT1-expressing pre-synaptic terminals. The presence of a GFP negative cell expressing VGLUT1 (FIG. 8G arrowheads) confirmed the presence of excitatory glutamatergic neurons in the culture. FIG. 8L shows consistent with the apparent presence of glutamatergic synaptic inputs, spontaneous excitatory postsynaptic currents (sEPSCs) were detected in the differentiation day 10-18 SHH treatment group NKX2.1::GFP+ neurons. All cells were plated on mouse cortical feeder following FACS for NKX2.1::GFP at differentiation day 32.

FIG. 9B presents an exemplary overlay of an averaged sIPSCs (gray; n=1S0) and mIPSCs (black; n=S6). Neurons were recorded on differentiation days 26-30 plated upon mouse cortical feeder cells. FIG. 9C presents an exemplary cumulative probability histogram of IPSCs (gray) and mIPSCs (black). FIG. 9D presents exemplary grouped data comparing the frequency of sIPSPs (gray; n=\ markers (MAP2), astrocytic markers (GFAP), GABA, and cortical markers (SATB2, TBR1) in human ESC derived cortical precursors at day 30 of differentiation. All cells were plated on mouse or human ESC-derived cortical feeder following FACS for NKX2.1::GFP at differentiation day 32.

FIGS. 10A-10D are data from FACS-mediated isolation of cortical neuron precursors based on expression of CD24 and lack of expression of CD44 and CXCR4 (CD184). FIGS. 10E-10L are images from immunocytochemical analyses for expression of neuronal markers (MAP2), astrocytic markers (GFAP), GABA, and cortical markers (SATB2, TBR1) in hESC-derived cortical precursors at differentiation day 30. FIGS. 10M-10T are images from immunocytochemical analyses for expression of neuronal markers (MAP2), astrocytic markers (GFAP), GABA, and cortical markers (SATB2, TBR1) in mouse E13.S cortical cultures.

FIGS. 11A-11C are representative tracings from GFP-positive neurons from the differentiation day 10-18 SHH treated group recorded on mouse cortical feeder cells (FIG. 11A and FIG. 11B) or human ESC-derived neurons enriched for putative cerebral cortical projection neurons (FIG. 11C). Depolarized voltage responses were initiated using protocols shown below each set of traces. The holding potential was −60 mV for all recordings. All cells were plated on mouse or human ESC-derived cortical feeder following FACS for NKX2.1::GFP at differentiation day 32.

FIGS. 12C and 12H), somatostatin (SST; (FIGS. 12D and 12I), and parvalbumin (PV; FIGS. 12E and 12J), each of which is present in subpopulations of mature cortical interneurons in humans.

Figures 1A, 1B, 1C, 1D, 1E, 1F, 1G, 1H:
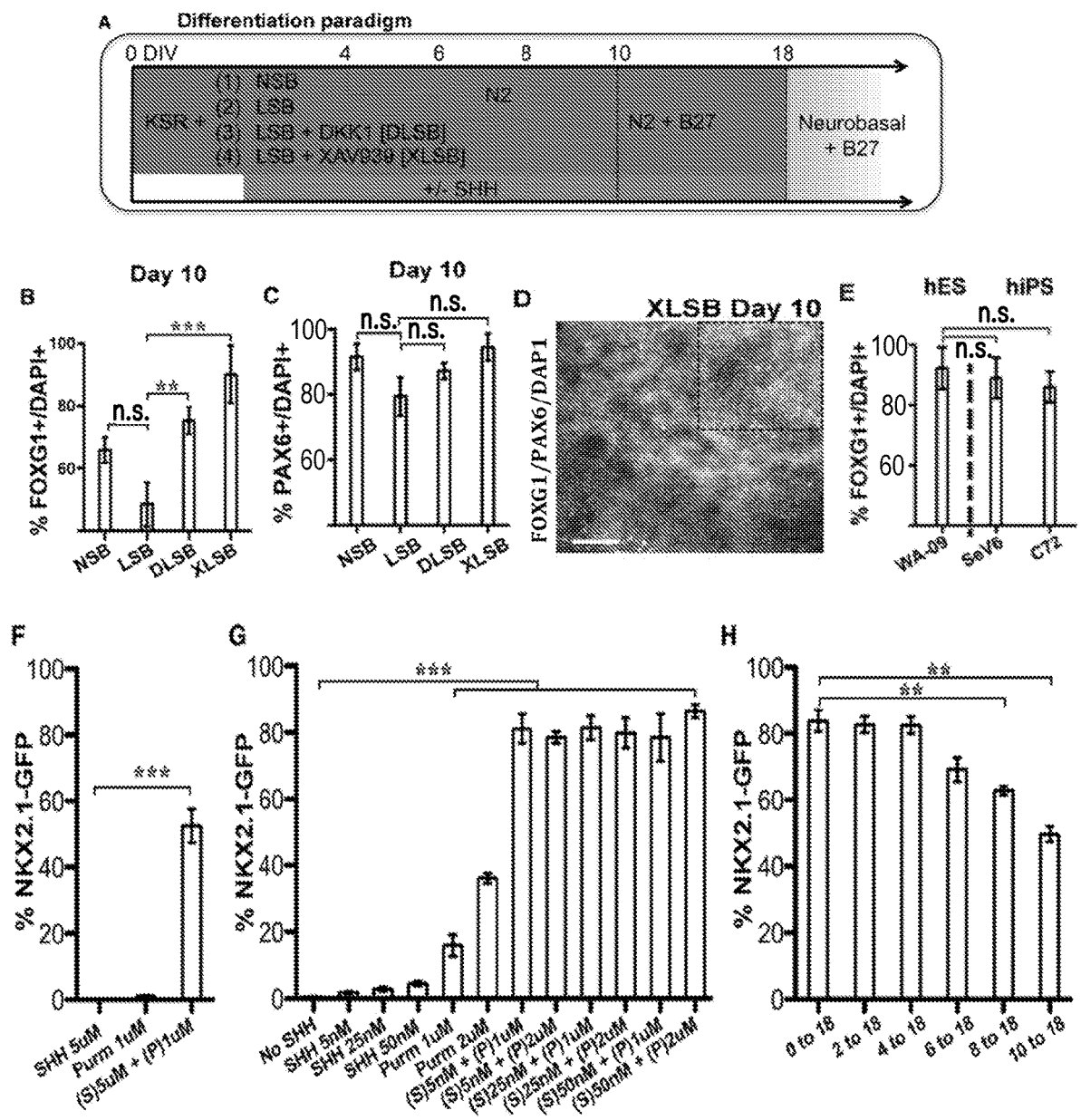
FIG. 1A-1H presents a schematic representation of a differentiation protocol using a dual SMAD inhibition paradigm to generate anterior neural progenitors. NSB: Noggin+ SB431542. LSB: LDN193189+ SB31542.

All cells were plated on mouse cortical feeder following FACS for NKX2.1::GFP at day 32. The scale bars in (FIGS. 12F-12J) represent 50 mm.

DETAILED DESCRIPTION

The present disclosure is based upon the discovery that forebrain neuron differentiation can be enhanced and that certain neurons of the central nervous system (CNS), including cortical interneurons, hypothalamic neurons, and pre-optic cholinergic neurons, can be efficiently induced in vitro by contacting certain pluripotent and/or multipotent cells (e.g., human embryonic stem cells (hESCs) and/or human induced pluripotent stem cells (hiPSCs)) with one and preferably two or more inhibitors of the SMAD transcription factor in combination with one or more Wnt antagonists at a suitable concentration and for a suitable duration to generate neuronal precursor cells, which neuronal precursor cells can be contacted with one or more activator of SHH signaling at a suitable concentration and for a suitable duration thereby inducing the production of one or more markers of a cortical interneuron or precursor cell thereof, one or more markers of a hypothalamic neuron or precursor cell thereof, and/or one or more markers of a pre-optic cholinergic neuron or precursor cell thereof.

Using an NKX2.1::GFP hESC reporter line, it was discovered that three distinct ventral forebrain precursor populations can be derived treating cells with XAV939 in conjunction with the timed activation of SHH signaling. As disclosed herein, results in both human pluripotent stem cells (PSCs) and in human embryos reveals distinctions between mouse and human forebrain development, including the transient expression of human FOXA2 within the ventral forebrain. The mature functional properties and expression of late cortical interneuron markers, including parvalbumin and somatostatin, evidenced the in vitro differentiation hPSCs into human cortical interneurons despite the protracted development of these cells in vivo. It was further discovered that, by adjusting the timing of SHH signal activation, neuronal differentiation can be directed towards the production of hypothalamic neurons or pre-optic cholinergic neurons.

XAV939 is a commercially available small molecule with the name 3,5,7,8-Tetrahydro-2-[4-(trifluoromethyl)phenyl]-4H-thiopyrano[4,3-d]pyrimidin-4-one, and a chemical formula of $C_{14}H_{11}F_3N_2OS$. The structure of XAV939 listed below. XAV929 is a tankyrase (TNKS) inhibitor and it antagonizes Wnt signaling via stimulation of β-catenin degradation and stabilization of axin. XAV939 inhibits proliferation of the μ-catenin-dependent colon carcinoma cell line DLD-1.

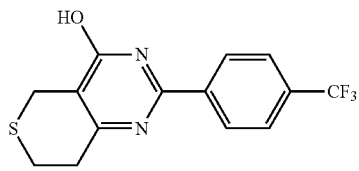 [SMILES: Oc1nc(-c2ccc(C(F)(F)F)cc2)nc2c1CSCC2]

Thus, the present disclosure provides methods for inducing the directed differentiation of pluripotent and/or multipotent cells, such as stem cells and progenitor cells, to generate a variety of stable neuronal cells (e.g., cortical interneuron cells, hypothalamic cells, and pre-optic cholinergic neurons) via the controlled induction of human pluripotent stem cells and the controlled induction of neuronal cells that result from directed differentiation of such stem cells with one or more SMAD inhibitor and/or Wnt antagonist to form populations of cells comprising cortical interneuron cells, hypothalamic cells, and/or pre-optic cholinergic neurons that can being advantageously employing for transplantation grafting or as a research platform for neurological disorders and diseases as well as for the identification and characterization of therapeutic drug candidates.

Provided herein are various differentiation inducers and experimental protocols that can be used to control directed neural cell differentiation. A highly efficient derivation of human cortical interneurons in a NKX2.1::GFP hESC reporter line is disclosed herein. In addition to harnessing the effects of SMAD and Wnt inhibition to guide the differentiation of stem cells into neuronal precursor cells, the present disclosure further describes manipulating the timing and duration of SHH activation to, thereby, achieve the generation of three distinct GFP+ neuronal cell populations, each exhibiting specific marker profiles, including specific transcriptional profiles, as well as corresponding neurotransmitter phenotypes and migratory behaviors.

As further disclosed herein, the differentiation in an in vivo murine cortical environment yields parvalbumin and somatostatin expressing neurons that exhibit synaptic inputs and electrophysiological properties of cortical interneurons. SHH-mediated signaling is, therefore, defined in sufficient detail to permit the generation of in vitro cell-based models of human ventral forebrain development, including cortical interneuron models, which can be employed for the developed of efficacious cell therapies, for drug screening, and for the study of human neurodegenerative and neuropsychiatric disease pathology.

Based upon these and other discoveries, which are described in detail herein, in certain embodiments, the present disclosure provides:

(1) In vitro methods for generating neurons, including neurons comprising one or more markers of a cortical interneuron or a cortical interneuron precursor, wherein the methods comprise the differentiation of a pluripotent cell or a multipotent cell by:
   a. contacting a pluripotent cell and/or a multipotent cell with one or more inhibitors of SMAD and with one or more antagonists of Wnt signaling, thereby inducing the generation of a neuronal precursor cell from said pluripotent and/or multipotent cell; and
   b. contacting the neuronal precursor cell with one or more activator of SHH signaling, thereby inducing in the neuronal precursor cell the production of one or more markers of a cortical interneuron and/or of a cortical interneuron precursor cell;

(2) In vitro methods for generating a neuronal cell producing one or more markers of a hypothalamic neuron and/or of a hypothalamic neuron precursor, wherein the neuronal cells is generated by differentiation of a pluripotent cell or a multipotent cell, the method comprising:
   a. contacting one or more pluripotent cells and/or one or more multipotent cells with (i) two or more inhibitors of SMAD and (ii) one or more antagonists of Wnt signaling, thereby inducing the generation of a neuronal precursor cell and
   b. contacting the neuronal precursor cell with one or more activator of SHH signaling, thereby inducing in the neuronal precursor cell the production of one or more marker of a hypothalamic neuron and/or of a hypothalamic neuron precursor cell;

(3) In vitro methods for generating a neuronal cell producing one or more markers of a pre-optic cholinergic neuron and/or of a pre-optic cholinergic neuron precursor cell, wherein the neuronal cell is generated by differentiation of a pluripotent cell and/or of a multipotent cell, the method comprising:
 a. contacting one or more pluripotent cells and/or one or more multipotent cells with (i) two or more inhibitors of SMAD and (ii) one or more antagonists of Wnt signaling, thereby inducing the generation of a neuronal precursor cell and
 b. contacting the neuronal precursor cell with one or more activator of SHH signaling, thereby inducing in the neuronal precursor cell the production of one or more marker of a pre-optic cholinergic neuron and/or of a pre-optic cholinergic neuron precursor cell;

(4) Compositions comprising one or more in vitro differentiated neuronal cells that produce one or more markers of a cortical interneuron cell and/or of a cortical interneuron precursor cell, wherein the in vitro differentiated neuronal cells are produced by:
 a. contacting a multipotent cell or a pluripotent cell with two or more inhibitors of SMAD signaling,
 b. contacting the multipotent cell or a pluripotent cell with one or more inhibitors of Wnt signaling, and
 c. contacting the multipotent cell or a pluripotent cell with one or more activators of SHH signaling;

(5) Compositions comprising one or more in vitro differentiated neuronal cells that produce one or more markers of a hypothalamic neuron or a hypothalamic neuron precursor cell, wherein the in vitro differentiated neuronal cells are produced by:
 a. contacting a multipotent cell or a pluripotent cell with two or more inhibitors of SMAD signaling,
 b. contacting the multipotent cell or a pluripotent cell with one or more inhibitors of Wnt signaling, and
 c. contacting the multipotent cell or a pluripotent cell with one or more activators of SHH signaling;

(6) Compositions comprising one or more in vitro differentiated neuronal cells that produce one or more markers of a pre-optic cholinergic neuron or a pre-optic cholinergic neuron precursor cell, wherein the in vitro differentiated neuronal cells are produced by:
 a. contacting a multipotent cell or a pluripotent cell with two or more inhibitors of SMAD signaling,
 b. contacting the multipotent cell or a pluripotent cell with one or more inhibitors of Wnt signaling, and
 c. contacting the multipotent cell or a pluripotent cell with one or more activators of SHH signaling;

(7) Cell based methods for identifying and characterizing inhibitors and/or antagonists of SMAD and Wnt signaling nad activators of SHH;

(8) Compositions comprising combinations of inhibitors and/or antagonists of SMAD and Wnt signaling and activators of SHH signaling;

(9) In vitro methods for generating a forebrain cell.

(10) Methods for the treatment of neurological disorders and diseases, including neurodegenerative disorders and diseases, such as Parkinson's disease, Alzheimer's disease, ALS, multiple system atrophy, and neuropsychiatric disorders and diseases, such as schizophrenia and autism related disorders, which methods comprise the in vivo administration to a patient of cortical interneurons, hypothalamic neurons, and/or pre-optic cholinergic neurons.

As described in greater detail herein, the presently disclosed methods and compositions are based upon the newly discovered, and presently disclosed, relationships between SMAD inhibition and Wnt antagonism in inducing the differentiation of a cell, such as a multipotent, pluripotent, and/or a totipotent cell, to generate a neuronal precursor cell and the further differentiation of such a neuronal precursor cell into cell within the cortical interneuron, hypothalamic, and pre-optic cholinergic lineages by contacting the neuronal cell with an activator of SHH under specific conditions of activator concentration and timing such that neuronal cells are generated having one or more markers of a cortical interneuron or precursor thereof, a hypothalamic cell or precursor thereof, and/or a pre-optic cholinergic cell or precursor thereof.

These and other aspects of the present disclosure are described in further detail herein, including: (1) methodology for generating neuronal cells from multipotent, pluripotent, and/or totipotent cells, including induced pluripotent stem cells (iPSCs) and embryonic stem cells (ESCs), in particular human cells, including human iPSCs (hiPSCs) and human ESCs (hESCs); (2) exemplary SMAD inhibitors, Wnt antagonists, and SHH activators that may be advantageously employed to generate cells of the cortical interneuron, hypothalamic neuron, and pre-optic cholinergic neuron lineages; (4) suitable conditions for generating neuronal cells from multipotent, pluripotent, and/or a totipotent cells and for generating cells of the cortical interneuron, hypothalamic neuron, and pre-optic cholinergic neuron lineages; (4) markers of cortical interneuronal cells and precursors, markers of hypothalamic cells and precursors, and markers of pre-optic cholinergic cells and precursors and methodology for detecting such markers in a cell; (5) compositions and formulations, including pharmaceutical compositions and formulations that are suitable for in vivo delivery to a patient, which compositions and formulations comprising cells of one or more of the cortical interneuron, hypothalamic neuron, and/or pre-optic cholinergic neuron lineages; (6) compositions and kits comprising suitable combinations and concentrations of SMAD inhibitors, Wnt antagonists, and SHH activators that can be used in in vitro cultures of multipotent, pluripotent, and/or totipotent cells to induce neuronal cell generation and in cultures of such neuronal cells to induce the generation of cells of the cortical interneuron, hypothalamic neuron, and pre-optic cholinergic neuron lineages; and (7) cell therapy based methodology for the treatment of a patient afflicted with and/or at risk for developing a neurodegenerative or neuropsychiatric disorder or disease by administering cells of the cortical interneuron, hypothalamic neuron, and pre-optic cholinergic neuron lineages.

Definitions

As used herein, the following terms (and cognates thereof) will have the meanings ascribed to them below unless the context requires otherwise.

The term "signaling" in reference to a "signal transduction protein" refers to proteins that are activated or otherwise affected (e.g., inhibited), directly or indirectly, by ligand binding to a membrane receptor protein or some other stimulus. Examples of signal transduction proteins include SMAD, Wnt, and SHH complex proteins. The term includes ligand-receptor interactions that are not directly linked to the cell's response. The ligand activated receptor thus may first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway and is included in the meaning of this term. As used herein, the following terms (and cognates thereof) will have the meanings ascribed to them below unless the context requires otherwise.

The term "Small Mothers Against Decapentaplegic" or "SMAD" refers to a class of signaling molecules capable of modulating directed cell differentiation of stem cells. SMADs are intracellular proteins that transduce extracellular signals from transforming growth factor beta ligands to the nucleus where they activate downstream gene transcription and are members of a class of signaling molecules capable of modulating directed differentiation of stem cells.

The term "wingless" or "Wnt" refers to a signal pathway composed of Wnt family ligands and Wnt family receptors, such as Frizzled and LRPDerailed/RYK receptors, whose signal transduction is mediated with or without β-catenin.

The term "sonic hedgehog" or "SHH" as used herein, refers to one of three proteins in the mammalian signaling pathway family called hedgehog (the other two being Indian hedgehog (IHH) and desert hedgehog (DHH)). SHH is believed to play a role in regulating vertebrate organogenesis, such as the growth of digits on limbs and organization of the brain. Sonic hedgehog protein is thus a morphogen that diffuses to form a concentration gradient and has different effects on the cells of the developing embryo depending on its concentration. SHH may also control cell division of adult stem cells and has been implicated in development of some cancers. SHH is associated with the regulation of various processes during embryogenesis, including cell-fate determination, reconstruction of organization, polarity, morphology, proliferation, and differentiation (Bertrand & Dahmane, Trends Cell Biol. 2006; 16: 597-605).

The term "inhibitor" in reference to inhibiting a signaling molecule or a signaling molecule's pathway, such as an inhibitor of SMAD signaling or Wnt signaling, refers to a compound or other molecule (e.g., small molecule, peptide, peptidomimetic, natural compound, siRNA, antisense nucleic acid, aptamer, or antibody) that interferes with (i.e. reduces or suppresses or eliminates or blocks) the signaling function of the molecule or pathway. In other words, an inhibitor is any compound or molecule that changes any activity of a named protein (signaling molecule, any molecule involved with the named signaling molecule, a named associated molecule, such as a glycogen synthase kinase 3β (GSK3β)) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules (e.g. within the extracellular domain, examples of a signaling molecule and an effect include: Noggin which sequesters bone morphogenic proteins, inhibiting activation of ALK receptors 1, 2, 3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFβ signaling molecules. Antibodies that block activins, nodal, TGFβ, and BMPs are contemplated for use to neutralize extracellular activators of SMAD signaling, and the like). Thus in one embodiment, an inhibitor of the present disclosure induces (changes) or alters differentiation from a default to a non-default cell type, for example, one of the methods of the present disclosure comprising at least 3 inhibitors that produced a non-default neural progenitor cell. In a preferred embodiment, an inhibitor disclosed herein "alters" or "lowers" or "blocks" default signaling in order to direct cellular differentiation towards a nondefault cell type, such as described herein for producing cortical interneurons as disclosed herein. Thus, an inhibitor of the present disclosure can be a biological compound, natural or synthetic, or a small molecule for increased or decreased signal molecule activity that assists in producing for example cortical interneurons of the present disclosure. Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule.

The term "LSB" refers to a combination of two compounds LDN-193189 and SB431542 capable of lowering or blocking signaling consisting of transforming growth factor beta (TGFβ)/Activin-Nodal signaling and Small Mothers Against Decapentaplegic (SMAD) signaling in a cell.

The term "XLSB" refers to a combination of three compounds, the first two of which include LDN-193189 and SB431542 capable of lowering or blocking signaling consisting of transforming growth factor beta (TGFβ)/Activin-Nodal signaling and Small Mothers Against Decapentaplegic (SMAD) signaling in a cell, and the last of which is XAV939, a tankyrase inhibitor capable of inhibiting Wnt signaling.

The term "SHH signaling pathway activator" is intended to refer to a substance activating the SHH signaling pathway. No particular limitations are imparted to the SHH signaling pathway activator if it enhances SHH-mediated signaling pathway. The SHH signaling pathway involves two transmembrane proteins, Ptc (Patched) and Smo (Smoothened), Examples of the SHH signaling pathway activators useful in the present invention include proteins belonging to the hedgehog family (e.g., purified SHH, recombinant SHH), SHH receptor activators (e.g. purmorphamine, Hg—Ag, etc.), inhibitors of Ptc's interaction with Smo, Smo receptor activators, substances increasing Ci/Gli family levels, inhibitors of the intracellular degradation of Ci/Gli factors, and Shh overexpression constructs or Ci/Gli overexpression constructs resulting from transfection. In some preferred embodiments, the "SHH signaling pathway activator" in the present disclosure include a recombinant SHH and purmorphamine.

The term "differentiation" as used with respect to cells in a differentiating cell system refers to the process by which cells differentiate from one cell type (e.g., a multipotent, totipotent or pluripotent differentiable cell) to another cell type such as a fully differentiated cell. More generally, the term "differentiation" refers to a process whereby an unspeciaiized stem cell or a precursor cell acquires the features of a specialized or fully differentiated cell such as a brain, heart, liver, or muscle cell. Differentiation is controlled by the interaction of a cell's genes with the physical and chemical conditions outside the cell, usually through signaling pathways involving proteins embedded in the cell surface.

The term "directed differentiation" refers to a manipulation of culture conditions of stem cells and precursor cells to induce differentiation into a particular (for example, desired) cell type, such as cortical interneuron cells according to the present disclosure.

The term "differentiation agent" refers to the use of one or more of small molecules, growth factor proteins, and other growth conditions to promote the transition of a unspecialized state, e.g., that of a stem cell into a more specialized cell fate (e.g. central nervous system cell, neural cell, forebrain neuronal cell, cortical interneurons, etc.). In other words, a differentiation gent is a substance which has the property of causing a stem cell to commit to a cellular pathway leading to a somatic cell. For example, such compounds may include, but are not limited to, Wnt activators or SMAD inhibitors.

The term "inducing differentiation" in reference to a cell refers to changing the default cell type (genotype and/or phenotype) to a non-default cell type (genotype and/or phenotype). Thus "inducing differentiation in a stem cell" refers to inducing the cell to divide into progeny cells with characteristics that are different from the stem cell, such as genotype (i.e. change in gene expression as determined by genetic analysis such as a micro array) and/or phenotype (i.e. change in expression of a protein, such as NKX2.1).

In some embodiment of this aspect of the present invention, the population of cells can be a population of transdifferentiated cells, preferably a population of human transdifferentiated cells. Transdifferentiated cells encompass mature differentiated cells of one tissue type whose phenotype is transdifferentiated or redirected into the phenotype of a mature cell of a different tissue without necessarily reverting to a pluripotent or multipotent phenotype. Cells that can undergo transdifferentiation include any somatic cell as well as adult stem cells. Methods of transdifferentiating cells are known in the art (see e.g., Thomas Kuntziger and PhilippeCollas, Transdifferentiation, in HANDBOOK OF STEM CELLS 147 (Robert Lanza ed., 2004), which is hereby incorporated by reference in its entirety). Methods of producing transdifferentiated neural progenitor cells and neuronal progenitor cells are described in U.S. Pat. Nos. 6,949,380, 6,087,168, and 7,041,507 to Levesque et al., and U.S. Patent Publication Nos. 20060099190 to Suh et al. and 2006/0251624 to Dezawa, which are hereby incorporated by reference in their entirety).

The term "contacting" cells with a molecule or substance as disclosed herein refers to placing the molecule in a location that will allow it to act upon the cell, such as by placing the molecule or substance in the culture medium of by introducing the molecule intracellularly, as the context may require. The molecule can be a small molecule compound, a polynucleotide, a polypeptide (e.g., a purified protein and/or a recombinant protein). Additionally, contacting also includes induced expression of a gene in a cell, e.g., transfecting the cell with a vector containing nucleic acid encoding the molecule. Contacting may be accomplished using any suitable method and may be extracellular or intracellular. For example, in one embodiment, contacting is by introducing the compound/substance intracellularly either as such or by genetically modifying the cell, such that it expresses the compound or substance. Contacting can be achieved by a variety of methods, including exposing cells to a molecule or to a vehicle containing a molecule, delivering a polynucleotide encoding for a polypeptide to the cells through transfection. Contacting may also be accomplished by adding the compound or substance to a culture of the cells so that the contacting occurs on the outer cell membrane. Contacting may also be accomplished within a given cell by the production of a recombinant protein.

The term "differentiation day" as used herein, refers to a time line having twenty-four hour intervals (i.e., days) after a stem cell culture is contacted by differentiation inducer molecules. For example, such inducer molecules may include, but are not limited to, Wnt inhibitors and SMAD inhibitor molecules. The day of contacting the culture with the inducer molecules is referred to as differentiation day 1. For example, differentiation day 2 represents anytime between twenty-four and forty-eight hours after the stem cell culture had been contacted by a differentiation inducer molecule.

The term "differentiation inducing molecule" refers to a molecule that has the property under certain culture conditions of causing differentiation of a multipotent, totipotent or pluripotent cell, leading, for example, to a neuronal cell. Such inducing compounds may include Wnt inhibitors or SMAD inhibitors or SHH activators without limitation.

The term "default" or "passive" in reference to a cell differentiation pathway refers to a pathway where a less specialized cell becomes a certain differentiated cell type in culture, when not treating with certain molecules i.e. normal cell cultures conditions. In other words, a default cell results when a cell is not contacted by a molecule capable of changing the differentiated cell type (i.e. a morphogen). In contrast, "non-default" in reference to a cell refers to a differentiated cell type that results that is different from a default cell, i.e. a nondefault cell is a differentiated cell type resulting from a non-default condition, such as cell of the present disclosure, including a cortical interneuron, hypothalamic neuron or pre-optic neuron, etc.

The term "ALK" or "anaplastic lymphoma kinase" or "anaplastic lymphoma receptor tyrosine kinase" or "Ki-1" refers to a membrane associated tyrosine kinase receptor.

The term "paired box gene 6" or "PAX6" refers to a marker of a nondefault neuroprogenitor cell.

The term "stem cell" refers to a cell that is totipotent or pluripotent or multipotent and is capable of differentiating into one or more different cell types. The term includes without limitation as embryonic stem cells, stem cells isolated from organs, for example, skin stem cells, and induced pluripotent stem cells (iPSC). The term "totipotent" refers to an ability of a cell to differentiate into any type of cell in a differentiated organism, as well as cell of extraembryonic materials such as placenta. As used herein, the term "induced pluripotent stem cell" or "iPSC" refers to a type of pluripotent stem cell that is similar to an embryonic stem cell but is created when somatic (e.g., adult) cells are reprogrammed to enter an embryonic stem cell-like state by being forced to express factors important for maintaining the "sternness" of embryonic stem cells (ESCs), i.e., their ability to be led to commit to different differentiation pathways. As used herein, the term "progenitor" in reference to a cell refers to an intermediate cell stage wherein said cell is no longer a pluripotent stem cell and is also not yet a fully committed cell. Progenitor cells in this disclosure are included within somatic cells.

The term "pluripotent" refers to a cell line capable of differentiating into any terminally differentiated cell type.

The term "multipotent" refers to a cell line capable of differentiating into at least two terminally differentiated cell types.

The term "embryonic stem cell" refers to a primitive (undifferentiated) cell that is derived from preimplantation-stage or early-stage embryo (for example, up to and including the blastocyst stage), capable of dividing without differentiating for a prolonged period in culture, and capable of developing into cells and tissues of the three primary germ layers. Embryonic stem cells can also be isolated from an embryo or placenta or umbilical cord.

The term "embryonic stem cell line" refers to a population of embryonic stem cells which have been cultured under in vitro conditions that allow proliferation without differentiation for days, months or even years.

The term "induced pluripotent stem cell" or "iPSC" refers to a type of pluripotent stem cell, similar to an embryonic stem cell, formed by the introduction of certain embryonic genes (such as a OCT4, SOX2, and KLF4 trans genes) (see, for example, Takahashi and Yamanaka Cell 126, 663-676 (2006), herein incorporated by reference) into a somatic cell. Examples of somatic cells include, but are not limited to, bone marrow cells, epithelial cells, fibroblast cells, hematopoietic cells, hepatic cells, intestinal cells, mesenchymal cells, myeloid precursor cells and spleen cells. Alternatively, the iPSC can be produced by reprogramming a somatic cell to enter an embryonic stem cell-like state by being forced to express factors important for maintaining the "sternness" of embryonic stem cells (ESCs), i.e., their ability to be led to commit to different differentiation pathways.

Methods for culturing stems cells, particularly human embryonic stem cells, are known in the art and described in WO2006/029297, WO2006/019366 and WO2006/029198 all to Thomson and Ludwig, and WO2008/089351 to Bergendahl and Thomson, which are hereby incorporated by reference in their entirety.

The term "neural cell culture" refers to a cell line displaying characteristics including, but are not limited to, expression of FOXA2, SHH, Netrin-1, F-Spondin.

The term "cell culture" refers to any in vitro culture of cells. Included within this term are continuous cell lines (e.g., with an immortal phenotype), primary cell cultures, finite cell lines (e.g., non-transformed cells), and any other cell population (notably neurons) maintained in vitro, including embryos, pluripotent stem cells, oocytes and embryos without limitation.

The term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

The term "precursor" in reference to a cell or an area of cells refers to the type of cell or area of cells that would develop (differentiate into) under the appropriate conditions, i.e. when contacted with a proper growth factor, compound, extracellular signal, intracellular signal, etc. For example, a "neuronal precursor cell" refers to a cell that is committed to becoming a neuron but has the potential of developing into more than one type of neuron, e.g., cortical interneuron or hypothalamic neuron etc.

The term "marker" or "cell marker" refers to a molecular or morphologic trait such as a gene or protein that, individually or as a member of a combination of two or more markers, identifies a particular cell or cell type. Thus, markers may refer to a "pattern" or combination of markers such that a designated group of markers may identify a cell or cell type from another cell or cell type. For example, forebrain cells express one or more markers that distinguish a forebrain cell, i.e. FOXA2 positive and NKX2.1 positive.

The term "forebrain" or "prosencephalon" refers to the rostral-most (forward-most) portion of the brain, and is one primary portion of the brain during early development of the central nervous system (CNS). The prosencephalon separates into the diencephalon (prethalamus, thalamus, hypothalamus, subthalamus, epithalamus, and pretectum) and the telencephalon (cerebrum).

The term "telencephalon" refers the embryonic structure of brain from which the mature cerebrum develops. In mammals, the dorsal telencephalon, or pallium, develops into the cerebral cortex, and the ventral telencephalon, or subpallium, becomes the basal ganglia. Exemplary markers for dorsal telencephalon include EMX2 and PAX6, and exemplary markers for ventral telencephalon include NKX2.1, NKX2.2, ASCL1, SIX6, OLIG2, and NKX6.2.

The term "cerebral cortex" refers to the outermost layered structure of neural tissue of the cerebrum (brain), in humans and other mammals.

The term "interneuron" is defined as a neuron which receives a neural signal from the target neuron and transmits the neural signal to a post-synaptic neuron. The interneuron's signal transmittal may be via its direct synaptic connection with the output neuron, or it may be via transmittal through one or more interneurons.

The term "cortical interneuron" refers to the interneurons of the cortex, including, but not limited to parvalbumin (PV)-expressing interneurons, CCK-expressing interneurons, VIP-expressing interneurons and SOM-expressing interneurons. In addition to these markers, other exemplary markers for cortical interneurons include GABA.

The term "cortical interneuron precursor cell" refers to a not fully differentiated neuronal cell that can be differentiated into cortical interneuron under suitable conditions. For example, cortical interneuron precursor cells can include NKX2.1+ ventral prosencephalic progenitor cells, cells from OLIG2+ ganglionic eminence, and neuronal progenitor cells expressing OLIG2, MASH1 and NKX6.2.

The terms "purified," "to purify," "purification," "isolated," "to isolate," "isolation," and grammatical equivalents thereof as used herein, refer to the reduction in the amount of at least one contaminant from a sample. For example, a cell type is purified by at least a 10%, preferably by at least 30%, more preferably by at least 50%, yet more preferably by at least 75%, and most preferably by at least 90%, reduction in the amount of undesirable cell types, such as isolated differentiated forebrain cells from non-forebrain cells, such as cells present in a mixed cell culture. Thus purification of a cell type results in an "enrichment," i.e., an increase in the amount and/or the percentage, of the cell type in the cell culture.

As used herein the term, "in vitro" refers to an artificial environment and to processes or reactions that occur within an artificial environment. In vitro environments exemplified, but are not limited to, test tubes and cell cultures.

As used herein the term, "in vivo" refers to the natural environment (e.g., an animal or a cell) and to processes or reactions that occur within a natural environment, such as embryonic development, cell differentiation, neural tube formation, etc.

The term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vivo, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

As used herein, the term "cultured cells" generally refer to cells that are maintained in vitro. Cultured cells include "cell lines" and "primary cultured cells. Included within this term are continuous cell lines (e.g., with an immortal phenotype), primary cell cultures, finite cell lines (e.g., non-transformed cells), and any other cell population (notably neurons) maintained in vitro, including embryos, pluripotent stem cells. Many cultured cells can proliferate in vitro but some, e.g., neurons, cannot.

The terms "monolayer," "monolayer culture," and "monolayer cell culture," refers to a cell that has adhered to a substrate and grow as a layer that is one cell in thickness, in other words, an "attached cell." Monolayers may be grown in any format, including but not limited to flasks, tubes, coverslips (e.g., shell vials), roller bottles, et cetera. The terms "feeder cells" refers to cells used to provide attachment molecules and/or growth factors for an adjacent cell, for example, used in co-culture to maintain pluripotent stem cells. For example, a feeder cell population may comprise embryonic mouse cortical cells or embryonic human cortical cells. Feeder cells commonly form a monolayer (i.e., "feeder cell layer"), or can exist in suspension. In some embodiments, these feeder cells include mouse embryonic fibroblasts.

The terms "culture media," and "cell culture media," refer to media that are suitable to support the growth of cells in vitro (i.e., cell cultures, cell lines, etc.). It is not intended that the term be limited to any particular culture medium. For example, it is intended that the definition encompass outgrowth as well as maintenance media. Indeed, it is intended that the term encompass any culture medium suitable for the growth of the cell cultures and cells of interest. Nonlimiting examples of culture media are Essential 6, Essential 8, KSR-based MEF conditioned media and mTESr.

The term "cell" refers to a single cell as well as to a population of (i.e., more than one) cells. The population may be a pure population comprising one cell type, such as a population of neuronal cells or a population of undifferentiated embryonic cells. Alternatively, the population may comprise more than one cell type, for example a mixed cell population. The use of the singular "cell" is not meant to limit the number of cells in a population, for example, a mixed population of cells may comprise at least one differentiated cell.

As used herein, the terms "diseases" or "disorders" refer to impairments of the normal state of a living animal, including a human, which interrupt or modify the performance of vital functions. In the context of the present disclosure, the terms "diseases" and "disorders" refer to neurological diseases and disorders, which include biochemical or electrical abnormalities of the nervous system (i.e., the brain, spinal cord, or other nerves). Within certain aspects of the present disclosure, neurological diseases and disorders include neurodegenerative diseases and disorders, which include, but are not limited to, diseases and disorders that are associated with a progressive loss of in the structure or function of neurons such as, for example, amyotrophic lateral sclerosis (ALS), Parkinson's disease (PD), Alzheimer's disease (AD), Huntington's disease (HD), multiple system atrophy (MSA), and multiple sclerosis (MS), which are characterized by one or more neurodegenerative processes. Within other aspects of the present disclosure, neurological diseases and disorders include neuropsychiatric diseases and disorders, which include, but are not limited to, diseases and disorders that are associated with changes in mood, disordered perceptions of reality, changes in personality, and eating disorders such as, for example, anxiety disorders, bipolar disorders, schizophrenia, anorexia nervosa, and bulimia nervosa, autism and related disorders. Within further aspects of the present disclosure, neurological diseases and disorders include neurodevelopmental disorders, which include, but are not limited to, holoprosencephaly or microcephaly.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "patient", as used herein, is a human or animal (e.g., a mammal for example a non-human primate, rodent etc.) and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies. Thus, the terms "subject" and "patient" are interchangeable.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "activator" or "activating" refers to compounds that have the property of activating molecules resulting in directed differentiation of cells of the present.

As used herein, the term "antagonist" refers to a compound that binds to and blocks or dampens an agonist-mediated biochemical response. In reference to the methods of the present disclosure, "antagonist" refers to a compound that binds to and blocks or dampens an agonist-mediated biochemical response that is a component of Wnt signaling. Wnt antagonists include agents that binds to receptors but does not provoke the normal biological response. Thus, an antagonist potentiates or recapitulates, for example, the bioactivity of patched, such as to repress transcription of target genes. The term "Wnt antagonist" as used herein refers not only to any agent that may act by directly inhibiting the normal function of the Wnt protein, but also to any agent that inhibits the Wnt signaling pathway, and thus recapitulates the function of Wnt. Examples of the Wnt signaling antagonists include XAV939 (Hauang et al., *Nature* 461:614-620 (2009)), vitamin A (retinoic acid), lithium, flavonoid, Dickkopf1 (Dkk1), insulin-like growth factor-binding protein (IGFBP) (WO2009/131166), and siRNAs against β-catenin.

The term "derivatives" of a molecule refer to molecules having structures sufficiently similar to the molecule of interest so as to function in a manner substantially similar to or substantially identical to the molecule of interest. For example, derivatives of a chemical compound can be modified through a variety of methods including acylation, methylation, alkali modification, acid modification, and inorganic salts modifications, oxidation, sulfonation, phenolation, hydroxymethylation, and enzymatic modification methods include protease modification, papain and urease modification, and chymotrypsin modification. For example, derivatives of a polypeptide can include mutant polypeptides with changes in one or more amino acids.

As used herein, the term "engineered" cell is intended to refer to a cell into which a desired nucleic acid, such as a nucleic acid encoding a variant NKX2.1, has been introduced. Engineered cells are distinguished from naturally occurring cells which do not contain introduced nucleic acid. Nucleic acid of the present disclosure includes nucleic acid obtained from a natural source, chemically synthesized, or produced by techniques of recombinant technology.

In Vitro Methods for Generating Neuronal Cells Producing Markers of Cortical Interneurons, Hypothalamic Neurons, and/or Pre-Optic Cholinergic Neurons The present disclosure provides in vitro methods for generating neuronal cells, including neuronal cells comprising one or more markers of a cortical interneuron, a hypothalamic neuron, a pre-optic cholinergic neuron. The present methods include contacting a pluripotent cell and/or a multipotent cell with one or more inhibitors of SMAD signaling and with one or more antagonists of Wnt signaling, thereby inducing the generation of a neuronal precursor cell, which neuronal precursor cell can be induced to differentiate into a neuronal cell comprising one or more markers of a cortical interneuron, a hypothalamic neuron, a pre-optic cholinergic neuron by contacting the neuronal precursor cell with one or more activators of SHH signaling.

Within certain embodiments, the present disclosure provides in vitro methods for generating a neuronal cell producing one or more markers of a cortical interneuron and/or of a cortical interneuron precursor cell, wherein the neuronal cell is generated by differentiation of a pluripotent cell or a multipotent cell, the method comprising: (a) contacting one or more pluripotent cells and/or one or more multipotent cells with (i) two or more inhibitors of SMAD signaling and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a cortical interneuron and/or of a cortical interneuron precursor cell.

Within other embodiments, the present disclosure provides in vitro methods for generating a neuronal cell producing one or more markers of a hypothalamic neuron and/or of a hypothalamic neuron precursor, wherein the neuronal cells is generated by differentiation of a pluripotent cell or a multipotent cell, the method comprising: (a) contacting one or more pluripotent cells and/or one or more multipotent cells with (i) two or more inhibitors of SMAD signaling and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a hypothalamic neuron and/or of a hypothalamic neuron precursor cell.

Within further embodiments, the present disclosure provides in vitro methods for generating a neuronal cell producing one or more markers of a pre-optic cholinergic neuron and/or of a pre-optic cholinergic neuron precursor cell, wherein the neuronal cell is generated by differentiation of a pluripotent cell and/or of a multipotent cell, the method comprising: (a) contacting one or more pluripotent cells and/or one or more multipotent cells with (i) two or more inhibitors of SMAD signaling and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a pre-optic cholinergic neuron and/or of a pre-optic cholinergic neuron precursor cell.

In some embodiments, the initiation and/or duration of exposure of a pluripotent cell and/or of a multipotent cell to SHH activators to produce different neuronal cell types (i.e., cortical interneurons, hypothalamic neurons, pre-optic cholinergic neurons) may overlap, depending on the culture medium used. In some embodiments, the initiation of SHH activation after starting SMAD/Wnt inhibition may happen from about 4 to about 20 days, commonly between about 6 and 15 days after SMAD signal inhibitor/Wnt antagonist introduction to produce cortical interneurons, while the initiation of SHH activation may also happen for example about 4 to about 8 days after SMAD/Wnt introduction to produce pre-optic cholinergic neurons. These time intervals will vary somewhat depending on culturing conditions, notably depending on the culturing medium used. Thus, when making hypothalamic neurons, exposure to SHH can start as early as simultaneously with or slightly after SMAD inhibitor/Wnt antagonist addition or prior to Pax6 or FoxG1 expression. When making cholinergic neurons, SHH can be initiated 2 days after SMAD/Wnt inhibition or up to 3 days before or up to 3 days after expression of these markers. When making interneurons on the other hand, SHH exposure can be initiated at least 2 days after expression of these markers and up to 10 and even 14 days after expression of these markers. Thus, the expression of these markers can be used as an alternative guide of when to commence SHH exposure.

When making interneurons or hypothalamic neurons or pre-optic cholinergic neurons, the duration of SHH activator exposure can be 5 to about 30 days or longer, commonly between about 8 and about 16 days. Specific combinations may include for example: For cortical interneurons start SHH activator 8 to 18 days after SMAD/Wnt inhibition and conclude (change medium) 8 to 16 days or 8-20 days thereafter. For hypothalamic neurons start SHH activator 1 to 4 days after SMAD/Wnt inhibition and conclude 5 to 30 or 8-16 days thereafter. For pre-optic basal forebrain cholinergic neurons start SHH activator 4 to 8 days after SMAD/Wnt inhibition and conclude 8 to 24 days thereafter.

Prolonged exposure to SHH activator is generally harmless. The cells can be expanded in the presence of SHH for extended periods of time. For example, in general, under the XLSB paradigm, 90% of the forebrain precursor cells will have been regionally patterned by 20 days. Stated another way, forebrain precursors in the presence of SHH will not be patterned to dorsal cortical projection neurons, and the unpatterned progenitors will diminish to insignificant levels by 20 days. Once the cells are NKX2.1 positive for any lineage, SHH can be left in the culture medium to expand precursors of any of these lineages. For example, interneuron precursors can be maintained for several months (e.g. 250 and 300 days or more) until use, such as engraftment or in vitro modeling of development or disease.

The neurons can be maintained in culture without exogenous factors for prolonged periods of time, such as several months.

As used herein, the term "signaling" has been defined previously. As disclosed herein, the SMAD and Wnt signaling pathways are important in mediating the differentiation of a pluripotent or multipotent cell, such as a pluripotent or multipotent stem or progenitor cell, to a neuronal precursor cell and the SHH signaling cascade is important in mediating the differentiation of a neuronal precursor cell to a neuronal cell that produces one or more markers of a cortical interneuron, a hypothalamic neuron, and/or a pre-optic chorionic neuron.

Differentiation of Stem Cells to Forebrain Neuronal Precursor Cells

As disclosed herein, cortical interneurons, hypothalamic neurons, and pre-optic chorionic neurons can be generated by inducing the differentiation of neuronal precursor cells with one or more activator of SHH signaling. Anterior/forebrain fate can be specified as a default program during neuronal differentiation of hPSCs. Chambers et al., *Nat Biotechnol* 27:275-280 (2009); Eiraku et al., *Cell Stem Cell* 3:519-532 (2008); Espuny-Camacho et al., *Neuron* 77:440-456 (2013); and Gaspard et al., *Nature* 455:351-357 (2008). Not all cells or cell lines adopt neural and anterior fates at equal efficiencies. Kim et al., *Cell Stem Cell* 8:695-706 (2011) and Wu et al., *Proc Natl Acad Sci USA* 104:13821-13826 (2007). Patterning factors that are secreted by differentiating cells include, for example, fibroblast growth factors (FGFs), Wnts, and retinoids, which factors can suppress forebrain induction and, thereby, trigger the induction of caudal cell fates.

Thus, the methods of the present disclosure achieve the generation of neuronal precursor cells by inducing the differentiation of multipotent and/or pluripotent cells by contacting the multipotent and/or pluripotent cells with a combination of one or more inhibitors of SMAD signaling and one or more antagonists of Wnt signaling.

Neuronal differentiation of hESCs via a dual SMAD-inhibition protocol is described in Chambers et al., *Nat Biotechnol* 27:275-280 (2009), which protocol employs the combination of Noggin and SB431542 (a/k/a NSB) to achieve the robust induction of FOXG1+/PAX6+ precursor cells.

As disclosed herein, the combination of an ALK2/3 inhibitor (e.g., LDN-193189) and SB431542 (a/k/a LSB) is also effective in inducing PAX6 expression albeit with a corresponding reduction in the percentage of cells expressing FOXG1. See, FIGS. 1B and 1C. FOXG1 expression in LSB-treated cultures was, however, greatly enhanced by the addition of one or more potent inhibitors of canonical Wnt signaling such as, for example, recombinant DKK1 and/or a tankyrase inhibitor (i.e., XA V939). See, FIGS. 1B-1D; Huang et al., *Nature* 461:614-620 (2009). Moreover, the XAV939-mediated induction of FOXG1 expression was consistent across multiple independent hESCs (HES-3 and WA-09) and human iPSCs (C72 and SeV6) tested. Papapetrou et al., *Proc Natl Acad Sci USA* 106:12759-12764 (2009) and Kriks et al., *Nature* 480:547-551 (2011). FIG. 1E.

Based, in part, upon these observations, the present disclosure provides methods that employ one or more inhibitor of SMAD signaling in combination with one or more antagonist of Wnt signaling to generate a neuronal precursor cell by inducing the differentiation of a multipotent and/or a pluripotent cell. As disclosed herein, the use of various combinations of Wnt antagonists and SMAD inhibitors including, but not limited to, DKK1, XA V939, LDN-193189, and SB431542 enables the rapid and robust induction of forebrain fates across a range of human ESCs and iPSC lines.

Multipotent, Pluripotent, and Totipotent Cells

The methods of the present disclosure are based, in part, of the observation that undifferentiated and/or uncommitted cells, including certain multipotent, pluripotent, and/or totipotent cells, can be induced by contacting with a combination of one or more SMAD inhibitors and one or more Wnt antagonists to generate neuronal cells. As part of the present disclosure, it was discovered that such neuronal cells can be further induced to generate cortical neurons, hypothalamic neurons, and pre-optic cortical neurons by contacting the neuronal cells with one or more activators of SHH under appropriate conditions, which include both the nature and concentration of the SHH activator as well as the timing of contact, including the duration of contact, with the SHH activator.

The terms "totipotent," "multipotent," "progenitor" have been described above. Progenitor cells in this disclosure are included within somatic cells. Progenitor cells are multipotent cells. Totipotent, pluripotent, and multipotent cells can be "stem cells," which are capable of differentiating into one or more different cell types. The term "stem cells," "embryonic stem cell", "induced pluripotent stem cell" have been described above.

Human pluripotent stem cells (hPSCs) are believed to be involved in modeling brain development and disease. Generally, the human cortex comprises two different types of neuronal populations, projection neurons and local interneurons. Cortical interneurons comprise a diverse class of cell types expressing the neurotransmitter GABA. Dysfunction of cortical interneurons has been implicated in neuropsychiatric diseases, including schizophrenia, autism and epilepsy.

Human pluripotent stem cells (hPSCs) have been used for studying human development and disease and for applications in regenerative medicine. The use of hPSCs differentiated towards central nervous system lineages has been of particular interest given the lack of effective therapies for many neurodegenerative and neuropsychiatric disorders and the availability of protocols to efficiently direct neuronal specification in vitro (Chambers et al., *Nat Biotechnol* 27:275-280 (2009)).

Early studies using hPSCs have been primarily geared towards neurodegenerative disorders, which are known to affect specific neuron types such as midbrain dopamine neurons in Parkinson's disease (PD; (Kriks et al., *Nature* 480:547-551 (2011); Soldner et al., *Cell* 136:964-977 (2009); and Soldner et al., *Cell* 146:318-331 (2011)) or motor neurons in amyotrophic lateral sclerosis (ALS; Dimos et al., *Science* 321:1218-1221 (2008)) and spinal muscular atrophy (SMA; Ebert et al., *Nature* 457:277-280 (2009)).

More recent studies suggest the possibility of tackling complex neuronal disorders such as schizophrenia (Brennand et al., *Nature* 473:221-225 (2011)) or autism-related syndromes. Marchetto et al., *Cell* 143:527-539 (2010) and Pasca et al., *Nat Med* 17:1657-1662 (2011)). Unlike in PD, ALS, or SMA, the neuron types critical for modeling schizophrenia or autism are less well defined, and no attempts have been made to direct neuron subtype identity in those studies. Recently, protocols were established for the derivation of human ESC-derived cortical projection neurons. Espuny-Camacho et al., *Neuron* 77:440-456 (2013) and Shi et al., *Nat Neurosci* 15:477-486, S471 (2012).

Inhibitory neurons such as cortical interneurons may, however, play a role in schizophrenia or autism. Insel, *Nature* 468:187-193 (2010) and Lewis et al., *Nat Rev Neurosci* 6:312-324 (2005). Previously, the derivation of cortical interneurons using a Lhx6::GFP reporter mouse ESC line was demonstrated. Maroof et al., *J Neurosci* 30:4667-4675 (2010). However, the efficiency of cortical interneuron generation was low, and it was uncertain whether those conditions would apply for generating human cortical interneurons from hPSCs. Modeling human cortical interneuron development in vitro is a particularly interesting challenge as the developmental origin of human cortical interneurons is controversial with studies suggesting that interneuron specification may differ considerably across mammalian species. Letinic et al., *Nature* 417:645-649 (2002) and Yu and Zecevic, *J Neurosci* 31:2413-2420 (2011). Furthermore, the protracted in vivo development of several cortical interneuron types (Anderson et al., *Neuroscience* 67:7-22 (1995)), represents another challenge for modeling their differentiation using human cells in vitro.

In some embodiments, the present disclosure relates to the use of human embryonic stem cells (ESC) (e.g., WA-09/H9). In some other embodiments, the present disclosure relates to the use of human induced pluripotent stem cells (iPSC) (e.g., SeV6, C72).

In some other embodiments, the present disclosure relates to the use of an adult stem cell. In some preferred embodiments, it is a human neural stem cell. Neural stem cells (NSCs) are self-renewing, multipotent cells that generate the main phenotypes of the nervous system. They undergo asymmetric cell division into two daughter cells, one non-specialized and one specialized. NSCs primarily differentiate into neurons, astrocytes, and oligodendrocytes. Alenzi and Bahkali, *African J Biotechnol* 10(86):19929-40 (2011).

The main distinction between stem cells is that one is an adult stem cell which is limited in its ability to differentiate and one is an embryonic stem cell (ESC) that is pluripotent. ESCs are not limited to a particular cell fate; rather they have the capability to differentiate into any cell type. Clarke et al., *Science* 288(5471):1660-63 (2000). ESCs are derived from the inner cell mass of the blastocyst with the potential to self-replicate. Alenzi and Bahkali, African *J Biotechnol* (2011).

Neural stem cells are considered adult stem cells because they are limited in their capability to differentiate. NSCs are generated throughout an adult's life via the process of neurogenesis. Paspala et al., *Neurology India* 59(4):558-65 (2011). Since neurons do not divide within the central nervous system (CNS), NSCs can be differentiated to replace lost or injured neurons or in many cases even glial cells. NSCs are differentiated into new neurons within the SVZ of lateral ventricles, a remnant of the embryonic germinal neuroepithelium, as well as the dentate gyrus of the hippocampus. Adult NSCs were first isolated from mouse striatum in the early 1990s. They are capable of forming multipotent neurospheres when cultured in vitro. Neurospheres can produce self-renewing and proliferating specialized cells. These neurospheres can differentiate to form the specified neurons, glial cells, and oligodendrocytes. Paspala et al., *Neurology India* 59(4):558-65 (2011). Cultured neurospheres have been transplanted into the brains of immunodeficient neonatal mice and have shown engraftment, proliferation, and neural differentiation.

In some other embodiments, the present disclosure relates to the use of a progenitor cell. In some preferred embodiments, it is a human neural progenitor cell. In the adult, neural stem cells persist within the forebrain ventricular zone, and give rise to a variety of more restricted progenitor phenotypes. The major progenitor pools of the adult human brain, include ventricular zone neuronal progenitor cells, hippocampal neuronal progenitors and parenchymal glial progenitor cells. Goldman et al., *Novartis Found Symp* 265:66-80 (2005). Each of these phenotypes exists within a local environmental niche, which tightly regulates both the mitotic activity and derivatives of its resident progenitors. For example, ventricular zone neuronal progenitor cells can be further differentiated into cortical interneurons.

Inhibitors of "Small Mothers Against Decapentaplegic" (SMAD)

Small Mothers against Decapentaplegic (SMAD) refers, generally, to a class of signaling molecules that are capable of modulating the directed cell differentiation of stem cells. SMADs are intracellular proteins that transduce extracellular signals from transforming growth factor beta ligands to the nucleus where they activate downstream gene transcription and are members of a class of signaling molecules capable of modulating directed differentiation of stem cells.

The term "inhibitor" has been described above.

In reference to the presently disclosed methods, inhibitors of SMAD signaling include compounds that interact with and reduce or block the activity of SMAD and/or a molecule that is associated with SMAD or other component molecules of SMAD signaling. Inhibitors can bind directly to and cause a conformational change in SMAD signaling, can reduce or prevent the expression of the gene encoding SMAD or a SMAD target gene, can decrease SMAD protein levels, and/or can interfere with SMAD interactions with one or more signaling partners.

Inhibitors also include molecules that indirectly regulate SMAD biological activity by intercepting upstream signaling molecules (e.g., within the extracellular domain, examples of a signaling molecule and an effect include: Noggin which sequesters bone morphogenic proteins, inhibiting activation of ALK receptors 1, 2, 3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFβ signaling molecules.

Antibodies that block activins, nodal, TGFβ, and BMPs are contemplated for use to neutralize extracellular activators of SMAD signaling, and the like). Thus in one embodiment, an inhibitor of the present disclosure induces (changes) or alters differentiation from a default to a non-default cell type, for example, one of the methods of the present disclosure comprising at least three inhibitors that produced a non-default neural progenitor cell.

Inhibitors disclosed herein "alter" or "lower" or "block" default signaling in order to direct cellular differentiation towards a nondefault cell type, such as described herein for producing cortical interneurons as disclosed herein. Thus, an inhibitor of the present disclosure can be a biological compound, natural or synthetic, or a small molecule for increased or decreased signal molecule activity that assists in producing for example cortical interneurons of the present disclosure.

Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule.

SMAD inhibitors that may be advantageously employed in the methods disclosed herein include those SMAD inhibitors that are well known in and are readily available to those having skill in the art. SMAD inhibitors that have been employed for the neural conversion of human ESCs and iPSCs are described in Chambers et al., *Nat Biotechnol* 27:275-280 (2009).

Exemplary SMAD inhibitors that can be used in the methods and compositions disclosed herein include the compounds designated SB431542, LDN-193189, Noggin PD169316, SB203580, LY364947, A77-01, A-83-01, BMP4, GW788388, GW6604, SB-505124, lerdelimumab, metelimumab, GC-I008, AP-12009, AP-11OI4, LY550410, LY580276, LY364947, LY2109761, SB-505124, E-616452 (RepSox ALK inhibitor), SD-208, SMI6, NPC-30345, Ki26894, SB-203580, SD-093, activin-M108A, P144, soluble TBR2-Fc, DMH-1, Dorsomorphin dihydrochloride, and a derivative and/or variant thereof, wherein each derivative and/or variant thereof possesses one or more SMAD inhibitory activities.

(a) TGFβ/Activin/Nodal Pathway Inhibitors

Inhibition of SMAD signaling pathway includes inhibition of TGFβ/Activin/Nodal pathway and the BMP pathway.

Exemplary TGFβ/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGF beta receptor (e.g., ALK5) inhibitors can include antibodies to, dominant negative variants of, and antisense nucleic acids that suppress expression of, TGF beta receptors (e.g., ALK5). Exemplary TGFβ receptor/ALK5 inhibitors include, but are not limited to, SB431542 (see, e.g., Inman, et al., Molecular Pharmacology 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., Cancer Science 96(11):791-800 (2005), and commercially available from, e.g., Toicris Bioscience); 2-(3-(6-Methylpyridin-2-yl)-IH-pyrazol-4-yl)-1,5-naphthyridine, Wnt3a/BIO (see, e.g., Dalton, et at., WO2008/094597, herein incorporated by reference), BMP4 (see, Dalton, supra), GW788388 (–{4-[3-(pyridin-2-yl)-1H-pyrazol-4-yl] pyridin-2-yl}-N(tetrahydro-2H-pyran-4-yl)benzamide) (see, e.g., Gellibert, et al., Journal of Medicinal Chemistry 49(7): 2210-2221 (2006)), SM16 (see, e.g., Suzuki, et al., Cancer Research 67(5):2351-2359 (2007)), IN-I 130 (3-((5-(6-methylpyridin-2-yl)-4-(quinoxalin-6-yl)-IHimidazol-2-yl) methyl)benzamide) (see, e.g., Kim et al., *Xenobiotica* 38(3): 325-339 (2008)), GW6604 (2-phenyl-4-(3-pyridin-2-yl-IH-pyrazol-4-yl)pyridine) (see, e.g., de Gouville, et al., Drug News Perspective 19(2):85-90 (2006)), SB-505124 (2-(5-benzo[1,3]dioxol-5-yl-2-tertbutyl-3H-imidazol-4-yl)-6-methylpyridine hydrochloride) (see, e.g., DaCosta et al., *Molecular Pharmacology* 65(3):744-752 (2004)) and pyrimidine derivatives (see, e.g., those listed in WO2008/006583, herein incorporated by reference).

Further, while "an ALK5 inhibitor" is not intended to encompass non-specific kinase inhibitors, an "ALK5 10 inhibitor" should be understood to encompass inhibitors that inhibit ALK4 and/or ALK7 in addition to ALK5, such as, for example, SB-431542. See, e.g., Inman et al., *J Mol Phamacol* 62(1):65-74 (2002). Without intending to limit the scope of the disclosure, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e., reprogramming) process.

Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-I008; ID11; AP-12009; AP-11OI4; LY550410; LY580276; LY364947; LY2109761; SB-505124; SB-431542; SD-208; SMI6; NPC-30345; Ki26894; SB-203580; SD-093; Gleevec; 3,5,7,2',4'-entahydroxyflavone (Morin); activin-M108A; P144; soluble TBR2-Fc; and antisense transfected tumor cells that target TGF beta receptors. See, e.g., Wrzesinski et al., *Clinical Cancer Research* 13(18):5262-5270 (2007); Kaminska et al., *Acta Biochimica Polonica* 52(2):329-337 (2005); and Chang et al., *Frontiers in Bioscience* 12:4393-4401 (2007).

Inhibitors of SMAD 2/3 phosphorylation can include antibodies to, dominant 5 negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., Oncogene 26:3311-3320 (2007); and Kataoka, et at., EP 1992360, incorporated herein by reference.)

SB-431542 (i.e., CAS 301836-41-9; IUPAC 4-[4-(1,3-benzodioxol-5-yl)-5-(2-pyridinyl)-1H-imidazol-2-yl]-benzamide) is a commercially available small molecule inhibitor of SMAD, which is capable of lowering or blocking transforming growth factor beta (TGFβ)/Activin-Nodal signaling.

The structure of SB431542 is listed below:

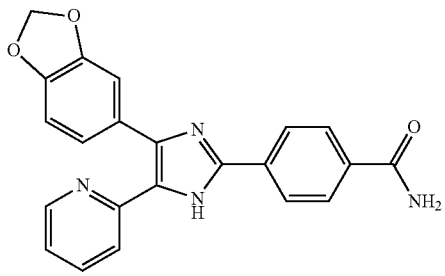 [SMILES: NC(=O)c1ccc(-c2nc(-c3ccc4c(c3)OCO4)c(-c3ccccn3)[nH]2)cc1]

Inhibitors of the interaction of SMAD 2/3 and SMAD 4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., Oncogene 24:3864-3874 (2005) and Zhao, et al., Molecular Biology of the Cell, 17:3819-15 3831 (2006).)

(b) BMP Inhibitors

Exemplary BMP pathway inhibitors include, but are not limited to: Noggin, BMP receptor inhibitors, inhibitors of SMAD 1/5/8 phosphorylation, inhibitors of the interaction of SMAD 1/5/8 and SMAD 4, and activators/agonists of SMAD 6 and SMAD 7. The categorizations described below are merely for organizational purposes and one of skill in the art would know that compounds can affect one or more points within a pathway, and thus compounds may function in more than one of the defined categories.

Inhibitors of SMAD 1/5/8 phosphorylation include, but are not limited to, antibodies to, dominant negative variants, antisense nucleic acids, and small molecules that target SMAD 1, SMAD 5, or SMAD 8. Specific examples of inhibitors include LDN-193189 and Dorsomorphin (commercially available from, e.g., Stemgent)

BMP receptor inhibitors include, but are not limited to, antibodies to, dominant negative variants of, siRNA or antisense nucleic acids, or small molecules that target BMP receptors. Specific examples of inhibitors include, but are not limited to, DMH-1, Dorsomorphin dihydrochloride, and LDN-193189 (commercially available, from, e.g., Tocris Biosciences).

LDN193189 (i.e., DM-3189, IUPAC 4-(6-(4-(piperazin-1-yl)phenyl)pyrazolo[1,5-a]pyrimidin-3-yl)quinolone) is a commercially available small molecule inhibitor of SMAD signaling. LDN193189 is also a highly potent small molecule inhibitor of ALK2, ALK3, ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8. Yu et al., Nat Med 14:1363-1369 (2008) and Ctmy et al., Bioorg Med Chem Lett 18: 4388-4392 (2008).

The structure of LDN193189 is listed below:

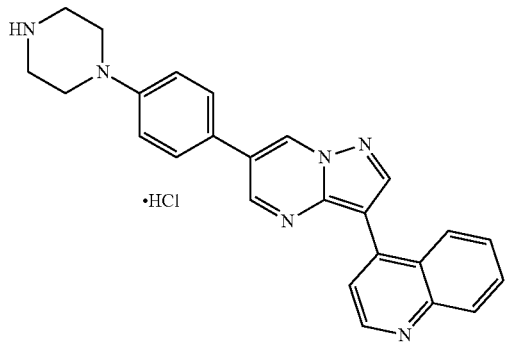 [SMILES: c1ccc2c(-c3cnn4cc(-c5ccc(N6CCNCC6)cc5)cnc34)ccnc2c1 ; Cl]

(c) Dual SMAD Inhibitors

SMAD signaling inhibitors can comprise the dual-SMAD inhibitors SB431542 and LDN-193189, or functional derivatives and/or variants thereof. As used herein, the terms "LSB" and "XLSB" have been described previously in the Definitions section. Dual SMAD inhibitors substantially increase the efficiency of the differentiation.

According to the methods of the present disclosure, SB431542 can be contacted with the pluripotent and/or a multipotent cell at a final concentration in an in vitro culture of from about 0.1 μM to about 1 mM. LDN-193189 can be contacted with the pluripotent and/or a multipotent cell at a final concentration in an in vitro culture of from about 1 nM to about 10 μM.

Antagonists of Wingless (Wnt) Signaling

"Wingless" or "Wnt" refers to a signal pathway composed of Wnt family ligands and Wnt family receptors, such as Frizzled and LRPDerailed/RYK receptors, mediated with or without β-catenin. Wnt proteins have been implicated in oncogenesis and in several developmental processes, including regulation of cell fate and patterning during embryogenesis.

The Wnt pathway includes any of the proteins downstream or upstream of Wnt protein activity. For example, this could include LRPS, LRP6, Dkk, GSK-3, Wnt10B, Wnt6, Wnt3 (e.g., Wnt 3A), Wnt1 or any of the other proteins discussed herein, and the genes that encode these proteins.

The Wnt pathway also includes pathways that are downstream of Wnt, such as the LRPS or HBM pathways, the Dkk pathway, the p-catenin pathway, the MAPKAPK2 pathway, the OPG/RANK pathway, and the like. By "LRP5 pathway" and "IBM pathway" is meant any proteins/genes including LRP5 or the HBM mutant and proteins downstream of LRPS or the HBM mutant. By "β-catenin pathway" is meant any proteins/genes including β-catenin and proteins downstream of β-catenin. By "MAPKAPK2 pathway" is meant any proteins/genes including MAPKAPK2 and proteins downstream of MAPKAPK2. By "OPG/RANKL pathway" is meant any proteins/genes including OPG/RANKL and proteins downstream of OPG and RANKL. By "Dkk pathway" is meant to include any proteins/genes involved in Dkk-1 and LRP5 and/or LRP6 interaction that is part of the Wnt pathway. Dkk-I inhibits LRP5 activity.

As used herein, the term "antagonist" has been described previously. The term "Wnt antagonist" as used herein refers not only to any agent that may act by directly inhibiting the normal function of the Wnt protein, but also to any agent that inhibits the Wnt signaling pathway, and thus recapitulates the function of Wnt. Examples of the Wnt signaling antagonists include XAV939 (Hauang et al. Nature 461:614-620 (2009)), vitamin A (retinoic acid), lithium, flavonoid, Dickkopf1 (Dkk1), insulin-like growth factor-binding protein (IGFBP) (WO2009/131166), and siRNAs against β-catenin.

Exemplary Wnt antagonists include, but are not limited to, XAV939, IWP-2, DKK1 (Dickkopf protein 1), and IWR1. Additional Wnt inhibitors include, but are not limited to, IWR compounds, IWP compounds, and other Wnt inhibitors described in WO09155001 and Chen et al., Nat Chem Biol 5:100-7 (2009).

XAV939 is a potent, small molecule inhibitor of tankyrase (TNKS) 1 and 2 with $IC_{50}$ values of 11 and 4 nM, respectively. Huang et al., Nature 461:614-620 (2009). By inhibiting TNKS activity, XAV939 increases the protein levels of the axin-GSK3β complex and promotes the degradation of β-catenin in SW480 cells. Known antagonists of Wnt signaling also include Dickkopf proteins, secreted Frizzled-related proteins (sFRP), Wnt Inhibitory Factor 1 (WIF-1), and Soggy. Members of the Dickkopf-related protein family (Dkk-1 to -4) are secreted proteins with two cysteine-rich domains, separated by a linker region. Dkk-3 and -4 also have one prokineticin domain. Dkk-1, -2, -3, and -4 function as antagonists of canonical Wnt signaling by binding to LRP5/6, preventing LRP5/6 interaction with Wnt-Frizzled complexes. Dkk-1, -2, -3, and -4 also bind cell surface Kremen-1 or -2 and promote the internalization of LRP5/6. Antagonistic activity of Dkk-3 has not been demonstrated. Dkk proteins have distinct patterns of expression in adult and embryonic tissues and have a wide range of effects on tissue development and morphogenesis.

The Dkk family also includes Soggy, which is homologous to Dkk-3 but not to the other family members. The sFRPs are a family of five Wnt-binding glycoproteins that resemble the membrane-bound Frizzleds. The largest family of Wnt inhibitors, they contain two groups, the first consisting of sFRP1, 2, and 5, and the second including sFRP3 and 4. All are secreted and derived from unique genes, none are alternate splice forms of the Frizzled family. Each sFRP contains an N-terminal cysteine-rich domain (CRO). Other antagonists of Wnt signaling include WIF-1 (Wnt Inhibitory Factor 1), a secreted protein that binds to Wnt proteins and inhibits their activity.

In some embodiments, the present disclosure relates to inhibitors and/or antagonists of the SMAD and Wnt signaling pathways. SMAD inhibitors include, but not limited to, SB431542, LDN-193189, Noggin PD169316, SB203580, LY364947, A77-01, A-83-01, BMP4, GW788388, GW6604, SB-505124, lerdelimumb, metelimumab, GC-I008, AP-12009, AP-110I4, LY550410, LY580276, LY364947, LY2109761, SB-505124, SB-431542, SD-208, SMI6, NPC-30345, Ki26894, SB-203580, SD-093, activin-M108A, P144, soluble TBR2-Fc, DMH-1, Dorsomorphin dihydrochloride and their derivatives. Wnt antagonists include, but not limited to, XAV939, DKK1, SFRP-1, SFRP-2, SFRP-5, SFRP-3, SFRP-4, WIF-1, Soggy, IWP-2, IWR1 and their derivatives.

In some aspects of these methods, SB431542 and LDN193189 can be used in combination to inhibit SMAD signaling pathway. In other aspects, XAV939 can be employed to antagonize the Wnt signaling pathway.

In other aspects of these methods, the concentration of XAV939 in a cell culture can be about 0.2 µM to 20 µM; the concentration of LDN193189 in a cell culture can be from about 10 nM to about 1000 nM, and the concentration of SB431542 in a cell culture can be from about 1 µM to about 100 µM. For example, the concentrations of XAV939 can be about 2 µM, the concentration of LDN193189 can be about 100 nM, and the concentration of SB431542 can be about 10 µM.

In further aspects of these methods, forebrain progenitor cells are generated by contacting stem cells with XAV939, LDN193189, and/or SB431542 for a duration of from about 5 days to about 40 days. In related aspects, forebrain progenitor cells are generated by contacting stem cells with XAV939, LDN193189, and/or SB431542 for a duration of from about 10 days to about 25 days.

Within further aspects of the methods according to any of these three embodiments, Wnt signaling antagonists can be selected from the group consisting of XAV939, DKK1, DKK-2, DKK-3, Dkk-4, SFRP-1, SFRP-2, SFRP-5, SFRP-3, SFRP-4, WIF-1, Soggy, IWP-2, IWR1, ICG-001, KY0211, Wnt-059, LGK974, IWP-L6, and a derivative and/or variant thereof, wherein each derivative and/or variant thereof possesses one or more Wnt signaling antagonist activities. For example, the Wnt signaling antagonist can comprise XAV939 or a functional derivative and/or variant thereof. XAV939 can be contacted with the pluripotent and/or multipotent cell at a final concentration in an in vitro culture of from about 10 nM to about 500 µM.

A variety of cell culture media and supplement can be used to differentiate stem cells into forebrain progenitor cells, including KSR-medium, N2 medium (DMEM/F12 with NaHCO3, N2B supplement (Stem Cell Technologies), and Neurobasal media with B27 (Gibco) and N2 supplements (Invitrogen). Kriks et al., *Nature* 480:547-551 (2011). In some embodiments, the cells are maintained on mouse embryonic fibroblasts (MEFs) as described previously and dissociated with Accutase (Innovative Cell Technologies) for differentiation or dispase for passaging (Chambers et al., *Nat Biotechnol* 27:275-280 (2009)).

Directed Differentiation to Generate Neuronal Cells Producing Markers of Cortical Interneurons, Hypothalamic Neurons, and/or Pre-Optic Cholinergic Neurons Provided herein are in vitro methods for generating neuronal cells that comprise one or more markers of a cortical interneuron, a hypothalamic neuron, and/or a pre-optic cholinergic neuron. Neuronal precursor cells are generated by contacting a pluripotent cell or a multipotent cell with one or more inhibitors of SMAD signaling and with one or more antagonists of Wnt signaling, thereby inducing the differentiation of the pluripotent cell or multipotent cell to generate a neuronal precursor cell, which can then be contacted with one or more activator of SHH signaling, thereby inducing in the neuronal precursor cell the production of one or more markers of a cortical interneuron, a hypothalamic neuron, a pre-optic cholinergic neuron, or a precursor thereof.

Activators of Sonig Hedgehog (SHH)

SHH signaling pathway is associated with the regulation of various processes during embryogenesis, including cell-fate determination, reconstruction of organization, polarity, morphology, proliferation, and differentiation (Bertrand & Dahmane, *Trends Cell Biol* 16:597-605 (2006). Sonic hedgehog (SHH) is one of three proteins in the mammalian signaling pathway family called hedgehog, the others being Indian hedgehog (IHH) and desert hedgehog (DHH). The SHH signaling pathway involves two transmembrane proteins, Ptc (Patched) and Smo (Smoothened). In the absence of SHH, Ptc interacts with and inhibits Smo. When SHH binds to Ptc, Ptc's interactions with Smo are altered such that Smo is no longer inhibited, leading to Ci/Gli protein entering the nucleus and acting as a transcriptional activator for target genes. No particular limitations are imparted to the SHH signaling pathway activator if it enhances SHH-mediated signaling pathway.

As used herein, the terms "sonic hedgehog" or "SHH" have been described previously in the Definitions section.

It has been reported that high-dose SHH treatment of hESC suppresses forebrain markers such as FOXG1 by inhibiting the induction of DKK1 thereby promoting the generation of floor plate like cells. Fasano et al., *Cell Stem Cell* 6:336-347 (2010). The generation of cortical interneurons, however, requires strong SHH activation at the NKX2.1+ progenitor stage. See, Xu et al., *J Neurosci* 24:2612-2622 (2004) and Xu et al., *Neuron* 65:328-340 (2010).

The ventral prosencephalic progenitor population transcription factor marker, NKX2.1, can be used to monitor differentiation. Sussel et al., *Development* 126:3359-3370 (1999) and Xu et al., *J Neurosci* 24:2612-2622 (2004). It was discovered, as part of the present disclosure, that inhibition of Wnt signaling enhances the production of FOXG1 and, subsequently, promotes ventralization by inducing the controlled, SHH-mediated differentiation of multipotent and pluripotent cells towards an NKX2.1+ forebrain progenitor fate. See, FIG. 1A. Ventral fate induction was further characterized by using combinations of XAV939, LDN-193189, SB431542 (XLSB), and SHH. See, FIG. 1A. The NKX2.1::GFP knock-in reporter hESC line was used to observe GFP induction by differentiation day 10 following activation of the SHH pathway by a recombinant SHH (R&D Systems, C-25II) and/or purmorphamine (FIG. 1F; Goulbum et al., 2011). Maximal induction of NKX2.1::GFP was observed at differentiation day 18 following treatment with a combination of 1 µM purmorphamine and 5 nM SHH. FIG. 1G.

Previous studies on the derivation of hESC derived floor plate cells suggested that early treatment with SHH (e.g., on differentiation day 1) resulted in the efficient induction of FOXA2. Fasano et al., *Cell Stem Cell* 6:336-347 (2010). The data presented herein demonstrates, however, that contacting cells with SHH at late differentiation stages (e.g., on differentiation day 10) induces robust NKX2.1::GFP expression as measured by FACS. FIG. 1H. Thus, as disclosed herein, it was discovered that XLSB in combination with SHH induced the generation of NKX2.1+ progenitor cells at high efficiencies.

The use of Wnt-inhibitory molecules, such as DKK1, has been previously proposed for generating telencephalic and optic progenitors during mouse and human ESC differentiation. Lamba et al., *Proc Natl Acad Sci USA* 103:12769-12774 (2006); Meyer et al., *Stem Cells* 29:1206-1218 (2011); and Watanabe et al., *Nat Neurosci* 8:288-296 (2005). It has also been shown that one or more SHH activators can enhance forebrain induction. For example, the SHH activator XAV939 (a tankyrase-inhibitor) can replace recombinant DKK1 for enhancing forebrain induction using a dual-SMAD inhibition protocol. Huang et al., *Nature* 461:614-620 (2009).

It has been reported that SHH can modulate in vitro ventral forebrain specification by using SHH concentrations that induce hESC-derived neuroepithelial progenitors to differentiate toward GSX2 positive, NKX2.1 negative progenitors that are capable of generating medium spiny striatal projection neurons. Ma et al., *Cell Stem Cell* 10:455-464 (2012). In addition to SHH-dose, it was further reported that the timing of SHH treatment affected the efficiency of ventral cell fate specification relative to hESC-based floor plate formation. Fasano et al., *Cell Stem Cell* 6:336-347 (2010).

Based, in part, upon those observations, the present disclosure provides methods for generating neuronal cells, in particular cortical interneurons and precursors thereof, hypothalamic neurons and precursors thereof, and pre-optic chorionic neurons and precursors thereof. According to these aspects of the present disclosure, the generation of such neuronal cell lineages and populations is achieved by contacting a neuronal precursor cells, such as a neuronal precursor cell generated as disclosed herein, with one or more activator of SHH signaling at a predetermined time after contacting a multipotent and/or pluripotent cell with one or more inhibitors of SMAD signaling and one or more antagonists of Wnt signaling and for a duration that is sufficient to induce the production of one or more markers of a cortical interneuron or precursor thereof, one or more markers of a hypothalamic neuron or precursor thereof, and/or one or more markers of a pre-optic chorionic neuron or precursor thereof.

As used herein, the term "activator" or "activating" has been described previously in the Definitions section. More specifically, and in reference to the methods of the present disclosure, the term "activator" refers to a compound that promotes and/or enhances SHH signaling thereby inducing a neuronal precursor cell to differentiate into a cortical interneuron or precursor thereof, a hypothalamic neuron or precursor thereof, and/or a pre-optic chorionic neuron or precursors thereof.

As used herein, the term "SHH signaling pathway activator" has been described previously in the Definitions section. Examples of the SHH signaling pathway activators useful in the present disclosure include proteins belonging to the hedgehog family (e.g., SHH), inhibitors of Pte's interaction with Smo, Smo receptor activators, Shh receptor activators (e.g., Hg—Ag, purmorphamine, etc.), substances increasing Ci/Gli family levels, inhibitors of the intracellular degradation of Ci/Gli factors, and SHH overexpression constructs or Ci/Gli overexpression constructs resulting from transfection.

In some aspects of the present methods, an SHH signaling pathway activator, (e.g., SHH+ purmorphamine), is added to the cell culture for the full or partial duration of the culture. In some embodiments, the concentrations of SHH activators in cell culture are about 10 ng/mL to about 5000 ng/mL for SHH (or recombinant SHH) and about 0.1 µM to about 20 µM for purmorphamine. In some preferred embodiments, the concentrations of SHH activators in cell culture are about 50 ng/mL to about 500 ng/mL for SHH (or recombinant SHH) and about 0.5 µM to about 4 µM for purmorphamine.

Purmorphamine is a commercially available small molecule with the name 9-cyclohexyl-N-[4-(morpholinyl)phenyl]-2-(1-naphthalenyloxy)-9H-purin-6-amine, and a chemical formula of $C_{31}H_{32}N_6O_2$. The structure of purmorphamine listed below. Purmorphamine binds to and activates the 7-transmembrane Smo receptor of the Hedgehog signaling pathway.

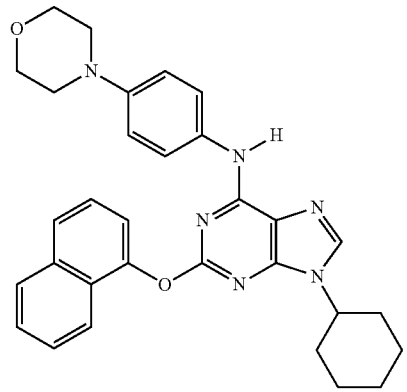 [SMILES: c1ccc2c(Oc3nc(Nc4ccc(N5CCOCC5)cc4)c4ncn(C5CCCCC5)c4n3)cccc2c1]

Within still further aspects of the methods according to any of these three embodiments, SHH signaling activators can be selected from the group consisting of Smoothened agonist (SAG), SAG analog, SHH, C25-SHH, C24-SHH, purmorphamine, Hg—Ag and a derivative and/or variant thereof, wherein each derivative and/or variant thereof possesses one or more SMAD inhibitory activities. For example, the SHH signaling activator can comprise recombinant SHH and purmorphamine, or functional derivatives and/or variants thereof. Recombinant SHH can be contacted with the pluripotent and/or multipotent cell at a final concentration in an in vitro culture of from about 5 ng/mL to about 5 µg/mL. Purmorphamine can be contacted with the pluripotent and/or multipotent cell at a final concentration in an in vitro culture of from about 0.1 µM to about 20 µM.

The data presented herein demonstrate that the difference in timing of SHH differentiation activation is crucial to trigger the generation of distinct ventral progenitors of divergent anterior-posterior identity. Early activation of SHH signaling in the derivation of hESC-derived progenitors expressing markers of the hypothalamic anlage requires the presence of FGF-8. Kriks et al., *Nature* 480:547-551 (2011). In contrast, some embodiments described herein demonstrate that addition of FGF-8 is not necessary for directing hypothalamic progenitor fate.

Neuronal precursor cells can be contacted with the one or more activator of SHH signaling after the passage of a predetermined period of time following generation of the neuronal precursor cell and/or following the contacting of the pluripotent and/or multipotent cell with the one or more inhibitors of SMAD and/or the one or more antagonists of Wnt signaling. For example, contacting the neuronal precursor cell with one or more activator of SHH signaling can be initiated from about 4 days to about 20 days or from about 8 days to about 18 days after contacting a pluripotent cell and/or a multipotent cell with one or more inhibitors of SMAD and with one or more antagonists of Wnt signaling. Contacting the neuronal precursor cell with one or more activator of SHH signaling can be for a time period of from about 5 days to about 30 days or from about 8 days to about 16 days.

Markers of Cortical Interneurons, Hypothalamic Neurons, and Pre-Optic Cholinergic Neurons As used herein, the term "marker" or "cell marker" has been described previously in the Definitions section, and refers to gene or protein that identifies a particular cell or cell type. A marker for a cell may not be limited to one marker. Markers may refer to a "pattern" of markers such that a designated group of markers may identify a cell or cell type from another cell or cell type. For example, forebrain cells of the present disclosure express one or more markers that distinguish a forebrain cell, i.e. FOXA2 positive and NKX2.1 positive. As used herein, the term "forebrain" or "prosencephalon" has been described previously in the Definitions section, and refers to the rostral-most (forward-most) portion of the brain, and is one primary portion of the brain during early development of the central nervous system (CNS). The prosencephalon separates into the diencephalon (prethalamus, thalamus, hypothalamus, subthalamus, epithalamus, and pretectum) and the telencephalon (cerebrum).

Markers of cortical interneurons and/or of cortical interneuron precursor cells have been described and are readily available to those of skill in the art and include, for example, SST, PV, GABA, calbindin, LHX6, RAX, FOXA2, FOXG1, OLIG2, MASH1, NKX6.2, VGLUT1, MAP2, CTIP2, SATB2, TBR1, DLX2, ASCL1, and ChAT.

Within other embodiments, the present disclosure provides in vitro methods for generating a neuronal cell producing one or more markers of a hypothalamic neuron and/or of a hypothalamic neuron precursor, wherein the neuronal cells is generated by differentiation of a pluripotent cell or a multipotent cell, the method comprising: (a) contacting one or more pluripotent cells and/or one or more multipotent cells with (i) two or more inhibitors of SMAD and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a hypothalamic neuron and/or of a hypothalamic neuron precursor cell.

Neuronal precursor cells producing the one or more markers of a hypothalamic neuron and/or of a hypothalamic neuron precursor cell can be subjected to conditions favoring neuronal precursor cell maturation. For example the neuronal precursor cell can be contacted with the one or more activator of SHH signaling after the passage of a predetermined period of time following generation of the neuronal precursor cell and/or following the contacting of the pluripotent and/or multipotent cell with the one or more inhibitors of SMAD and/or the one or more antagonists of Wnt signaling. In some other embodiments, a cortical feeder environment was created using embryonic mouse cortical cells to accelerate the maturation of neuronal cells in vitro.

Contacting the neuronal precursor cell with one or more activator of SHH signaling can, for example, be initiated from about 1 day to about 4 days after contacting a pluripotent cell and/or a multipotent cell with one or more inhibitors of SMAD and with one or more antagonists of Wnt signaling to produce a hypothalamic neuron or a hypothalamic neuron precursor. Contacting the neuronal precursor cell with one or more activator of SHH signaling can be for a time period of from about 5 days to about 30 days or from about 8 days to about 20 days.

Markers of a hypothalamic neurons and of hypothalamic neuron precursor cells have been described and are readily available to those of skill in the art and include NGFI-B, c-fos, CRF, tyrosine hydroxylase (TH), RAX, POMC, hypocretin, and NADPH.

Within further embodiments, the present disclosure provides in vitro methods for generating a neuronal cell producing one or more markers of a pre-optic cholinergic neuron and/or of a pre-optic cholinergic neuron precursor cell, wherein the neuronal cell is generated by differentiation of a pluripotent cell and/or of a multipotent cell, the method comprising: (a) contacting one or more pluripotent cells and/or one or more multipotent cells with (i) two or more inhibitors of SMAD and (ii) one or more antagonists of Wnt signaling, thereby inducing the generation of a neuronal precursor cell and (b) contacting the neuronal precursor cell with one or more activator of SHH signaling, thereby inducing in the neuronal precursor cell the production of one or more marker of a pre-optic cholinergic neuron and/or of a pre-optic cholinergic neuron precursor cell.

Neuronal precursor cells producing markers of a pre-optic cholinergic neuron and/or of a pre-optic cholinergic neuron precursor cell can be subjected to conditions favoring neuronal precursor cell maturation.

Neuronal precursor cells can be contacted with one or more activator of SHH signaling after the passage of a predetermined period of time following the generation of the neuronal precursor cells and/or following the contacting of the pluripotent and/or multipotent cell with two or more inhibitors of SMAD and/or one or more antagonists of Wnt signaling.

Contacting the neuronal precursor cell with one or more activator of SHH signaling can be initiated from about 4 days to about 8 days after contacting a pluripotent cell and/or a multipotent cell with one or more inhibitors of SMAD and with one or more antagonists of Wnt signaling to produce a pre-optic cholinergic neuron or a pre-optic cholinergic neuron precursor. Contacting the neuronal precursor cell with one or more activator of SHH signaling can be for a time period of from about 5 days to about 30 days or from about 8 days to about 24 days.

Markers of a pre-optic cholinergic neurons and/or of a pre-optic cholinergic neuron precursor cells are known and readily available to those of skill in the art. Such markers of pre-optic cholinergic neurons and/or of a pre-optic cholinergic neuron precursor cells include, for example, ChAT, NGF, Ach, VAChT, LHX8, Isl1, and p75.

It will be understood that pluripotent cells and/or multipotent cells can be human cells or murine cells, which can be selected from the group consisting of embryonic stem cells, adult stem cells, neural stem cells, induced pluripotent cells, engineered pluripotent cells, primary progenitor cells, induced progenitor cells, and engineered progenitor cells.

Contacting with SMAD inhibitors and/or contacting with Wnt signaling antagonists can be carried out simultaneously or can be carried out sequentially. Contacting can be for a duration of from about 5 days to about 30 days.

Within still further aspects of the methods according to any of these three embodiments, the neuronal precursor cells comprise one or more markers selected from the group consisting NKX2.1, NKX2.2, LHX6, LHX8, DLX1, DLX2, DLX5, DLX6, SOX6, MAFB, NPAS1, ASCL1, SIX6, OLIG2, and NKX6.2.

Within still further aspects of the methods according to any of these three embodiments, the contacting with one or more inhibitors of SMAD, one or more antagonists of Wnt signaling, and/or one or more activators of SHH signaling can be carried out in the presence of a feeder cell, such as a mouse cortical pyramidal neuron, for example a mouse cortical pyramidal neuron that is derived from a mouse ESC.

In some embodiments, methods by the current disclosure can be used to produce a variety of cells, including cortical interneurons and their precursors, at an amount and purity that cannot be obtained by the state of the art. A large number of pure, functional cortical interneurons obtained by using methods of the present disclosure, in some embodiments, can be used to study schizophrenia or autism, and other neurological disease. Similarly, these cells can also be used in drug screening and in cell therapy.

Methods for Generating Ventral Precursor Cells

Within certain embodiments, the present disclosure provides methods for generating ventral progenitor cells, which methods comprise exposing cells to a ventralization factor, such a sonic hedgehog (SHH). Alternatively, the cells are exposed to an agent that mimics Shh or to an agonist of SHH.

In some embodiments of the present disclosure, the activation of SHH pathway is initiated at least 8 days and up to 18 days after initiation of the inhibition of SMAD and Wnt to produce cortical interneurons or their precursors. In some embodiments, the activation of SHH pathway is concluded from about 5 days and to about 30 days after its initiation. In some embodiment, SHH activators can be added to the cultured cells for a longer duration, from about 30 days to about 60 days. In some preferred embodiments, the activation of SHH pathway is initiated between about 8 days and about 18 days after initiation of the inhibition of SMAD and Wnt, and concluded between about 8 days and to about 16 days after its initiation to produce cortical interneurons or their precursors.

In some other embodiments of the present disclosure, the activation of SHH pathway is initiated at least 1 days and up to 4 days after initiation of the inhibition of SMAD and Wnt to produce hypothalamic neurons or their precursors. In some embodiments, the activation of SHH pathway is concluded from about 5 days and to about 30 days after its initiation. In some embodiments, SHH activators can be added to the cultured cells for a longer duration, from about 30 days to about 60 days. In some preferred embodiments, the activation of SHH pathway is initiated between about 1 days and about 4 days after initiation of the inhibition of SMAD and Wnt, and concluded between about 8 days and to about 20 days after its initiation to produce hypothalamic neurons or their precursors.

In some other embodiments of the present disclosure, the activation of SHH pathway is initiated at least 4 days and up to 10 days after initiation of the inhibition of SMAD and Wnt to produce pre-optic cholinergic neurons or their precursors. In some embodiments, the activation of SHH pathway is concluded from about 5 days and to about 30 days after its initiation but may be maintained longer. In some embodiments, SHH activators can be added to the cultured cells for a longer duration, from about 30 days to about 60 days. In some embodiments, the activation of SHH pathway is initiated between about 4 days and about 8 days after initiation of the inhibition of SMAD and Wnt, and concluded between about 8 days and to about 24 days after its initiation to produce pre-optic cholinergic neurons or their precursors.

In some embodiment of the present disclosure, after permitting the isolated population of cells to differentiate to immature interneuron precursor cells, a purified and enriched population of the immature interneuron precursor cells is recovered. This recovery procedure is preferably carried out by the promoter based separation procedure, utilizing an enhancer/promoter which functions only in the immature interneuron precursor cells and not other cell types.

The identity of cortical interneurons produced by methods described by the present disclosure can be ascertained by molecular and morphological signatures of the cells. Some molecular markers of cortical interneurons and their precursors have been described, including, but not limited to SST, PV, GABA, calbindin, LHX6, RAX, FOXA2, FOXG1, OLIG2, MASH1, NKX6.2, VGLUT1, MAP2, CTIP2, SATB2, TBR1, DLX2, ASCL1, ChAT and combinations of thereof. See, Wonders and Anderson, *Nat Rev Neurosci* 7:687-696 (2006).

The identity of hypothalamic neurons produced by methods described by the present disclosure can be ascertained by molecular and morphological signatures of the cells. Some molecular markers of hypothalamic neurons and their precursors have been described, including, but not limited to NGFI-B, c-fos, CRF, tyrosine hydroxylase (TH), RAX, POMC, hypocretin, NADPH and combinations thereof (see Cheng M F. Front Neuroendocrinol. 2013 August; 34(3): 167-78.).

The identity of pre-optic cholinergic neurons produced by methods described by the present disclosure can be ascertained by molecular and morphological signatures of the cells. Some molecular markers of pre-optic cholinergic neurons and their precursors have been described, including, but not limited to, ChAT, NGF, Ach, VAChT (see Bruel-Jungerman E et al., Behav Brain Res. 2011 Aug. 10; 221(2):379-88), LHX8, Isl1, p75 and combinations thereof.

NKX2.1 Precursor Neuronal Differentiation and Migratory Properties

Cortical interneurons derived from the ganglionic eminence may be involved in balancing excitation and inhibition within cortical circuitry. In addition, cortical interneurons also play roles in controlling developmental plasticity, and may become dysfunctional in various pathological conditions ranging from epilepsy to autism and schizophrenia. Baraban et al., *Proc Natl Acad Sci USA* 106:15472-15477 (2009); Eagleson et al., *Autism Res* 4:68-83 (2011); Insel, *Nature* 468:187-193 (2010); Lewis et al., *Nat Rev Neurosci* 6:312-324 (2005); and Penagarikano et al., *Cell* 147:235-246 (2011).

Figures 4A, 4P:
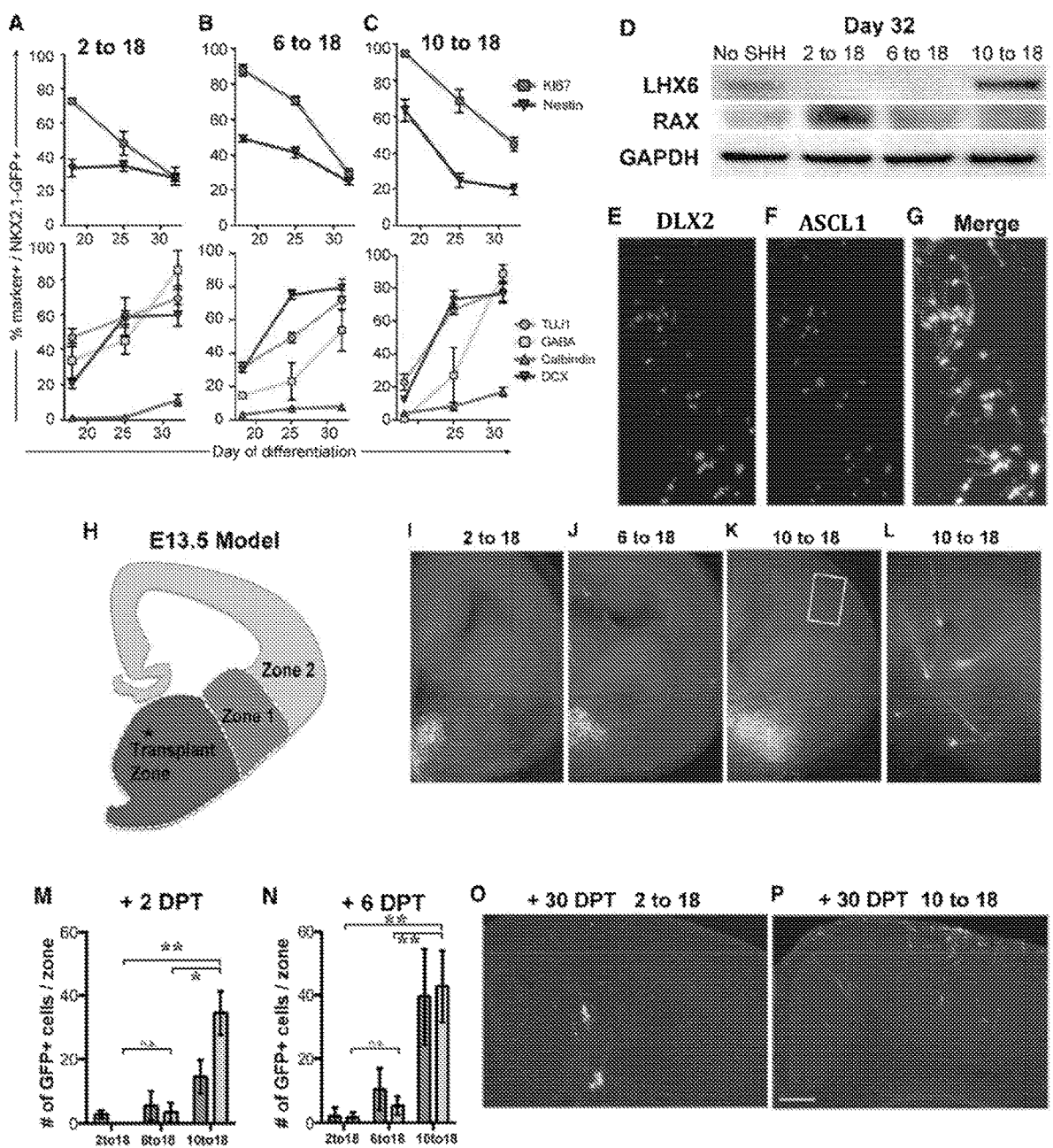
FIG. 4A-4P presents exemplary data showing a conversion from cycling neural progenitors to neuronal precursors and the assessment of their migratory potential.

The data presented herein suggest that the differentiation day 10-18 SHH treated precursor cells express many of the transcription factors known to mark portions of the cortical interneuron progenitor domain during mouse development, including OLIG2, MASH1, and NKX6.2. Most NKX2.1::GFP cells at differentiation day 18 exhibit progenitor cell properties, as shown by Nestin and Ki67 expression. However, prolonged culture in the absence of extrinsic SHH activation led to a gradual decrease in cycling NKX2.1::GFP cells (FIGS. 4A-4C, upper panels). For example, decreased Ki67 rates were paralleled by increases in the percentage of cells expressing the neuronal precursor markers DCX and TUJ1 (FIGS. 4A-4C, lower panels).

In addition, many of the GFP+ cells in the differentiation day 10-18 SHH treatment group and the differentiation day 2-18 SHH treatment group express GABA and show a time-dependent increase in the expression of calbindin (FIGS. 4A-4C, lower panels), a marker of tangentially-migrating cortical interneuron precursors as well as other populations. Anderson et al., *Science* 278:474-476 (1997).

Importantly, Western Blot analysis at differentiation day 32 showed that LHX6 protein, a marker of post-mitotic migratory cortical interneuron precursors in the mouse, was selectively enriched in the differentiation day 10-18 SHH treated group. In contrast, the hypothalamic marker RAX was selectively enriched in the differentiation day 2-18 SHH treated group (FIG. 4D).

Additional immunocytochemical data showed expression of DLX2 and ASCL1 in most neuronal progeny derived from the differentiation day 10-18 SHH treated NKX2.1::GFP+ progenitors (FIGS. 4E-4G). These data suggest that following withdrawal of extrinsic SHH signaling activators, NKX2.1::GFP+ progenitors give rise to region-specific post-mitotic neurons, including the precursors of cortical interneurons.

It was also of interest whether human ESC-derived putative cortical interneuron precursors (e.g., differentiation day 10-18 SHH treatment group) exhibit the previously observed characteristic migratory potential observed for primary cortical interneurons in the mouse (Anderson et al., *Science* 278:474-476 (1997)) and human (Letinic et al., *Nature* 417:645-649 (2002)) brain. In both species, major subclasses of cortical interneurons are believed to undergo tangential migration while differentiating from ventral telencephalon into cortex (Anderson et al., *Science* 278:474-476 (1997); Fertuzinhos et al., *Cereb Cortex* 19(9):2196-2207 (2009); and Letinic et al., *Nature* 417:645-649 (2002)).

NKX2.1::GFP+ cells were collected by FACS at differentiation day 32 and injected into forebrain slices isolated from embryonic day 13.5 mouse embryos. Cell injections were carefully targeted to the medial ganglionic eminence under microscopic visual guidance (FIG. 4H). The migratory potential of NKX2.1::GFP+ cells and their ability to reach the cortex (see Zone 2 in FIG. 4H) was compared among the differentiation day 2-18 SHH treatment group, the differentiation day 6-18 SHH treatment group and the differentiation day 10-18 SHH treatment group. (FIGS. 4I-4L).

GFP+ cells were observed migrating from the injection site towards the cortex (zone 2) at day 2 and, more pronounced at day 6 after injection (FIGS. 4M and 4N, respectively). Remarkably, human cells from the differentiation day 10-18 SHH treated group, but not the two other treatment groups, showed a robust propensity for migration into the neocortical portions of the murine slice (FIGS. 4I-4N). These data suggest that differentiation day 10-18 SHH treated cells exhibit migratory properties previously described for primary mouse MGE-derived interneuron precursors. Lavdas et al., *J Neurosci* 19:7881-7888 (1999); Sussel et al., *Development* 126:3359-3370 (1999); and Wichterle et al., *Nat Neurosci* 2:461-466 (1999).

Migratory capacity of the differentiation day 2-18 SHH treated cells versus the differentiation day 10-18 treated cells was determined by transplanting FACS-isolated NKX2.1::GFP+ cells into the neocortex of neonatal, genetically immunocompromised mice. Four weeks after transplantation the differentiation day 10-18 SHH treated cells showed extensive migration in both the radial and tangential planes within the mouse cortex (FIGS. 4O and 4P). Similar results were obtained upon transplantation into the adult cortex though overall migration of NKX2.1::GFP+ cells by day 30 in vivo was less extensive compared to the neonatal grafts (FIG. 5A-5D).

Figures 5A, 5B, 5C, 5D:
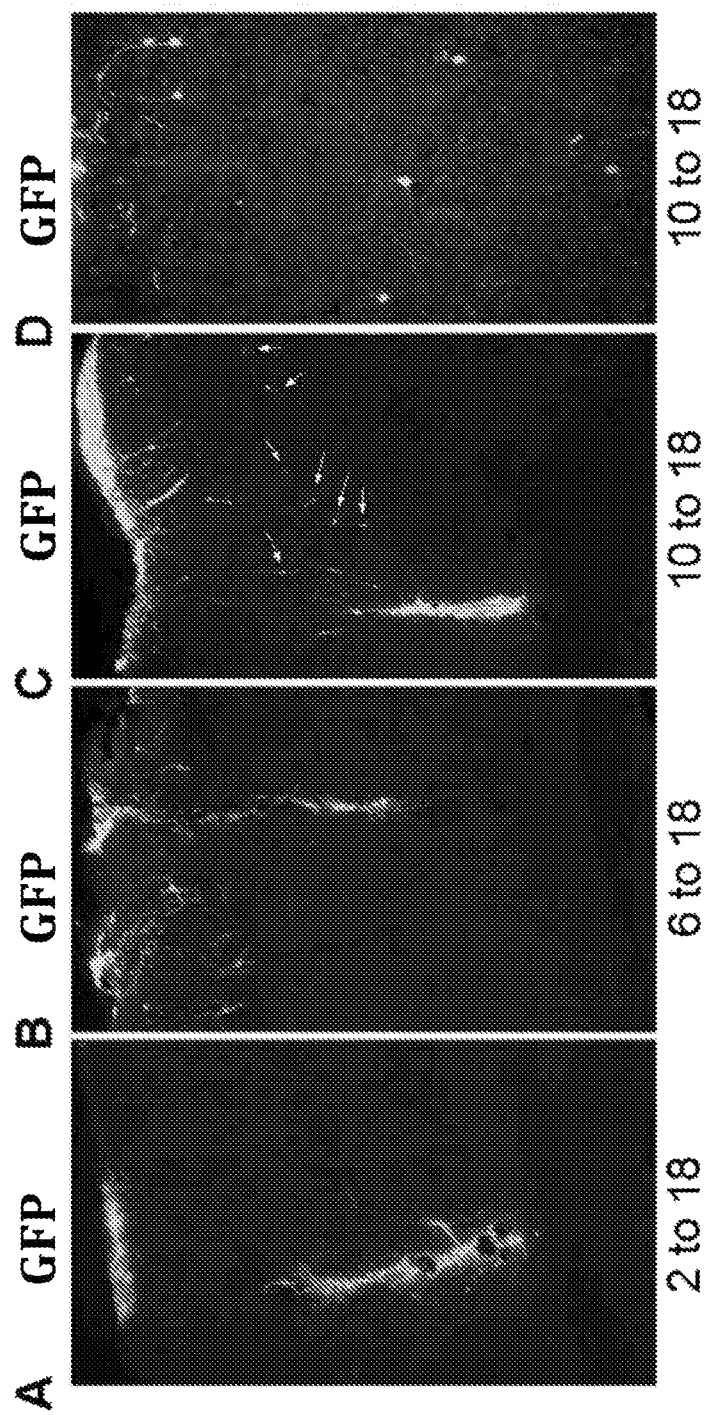
FIG. 5A-5D presents exemplary data showing the distribution of NKX2.1::GFP+ neuronal precursors within the adult mouse cortex. NKX2.1::GFP expressing cells were sorted at differentiation day 32 and grafted into adult IL2RG immunocompromised mice. The differentiation day 2-18 SHH treatment group (FIG. 5A) and the differentiation day 5 6-18 SHH treatment group (FIG. 5B) showed regions of GFP expression in the cortex after 30 days, meaning that the GFP cell bodies did not leave the graft core. The differentiation day 10-18 SHH treatment group (FIG. 5C) showed that GFP expressing cells left the graft core and distributed throughout the cortical parenchyma. In addition, the GFP expressing cells from the differentiation day 10-18 SHH treatment group distributed throughout the cortical layers and 10 display neuronal morphologies (FIG. 5D).

To determine the extent of interneuron precursor maturation in vivo, morphological appearance and the expression of interneuron-related markers in the grafted cells was assessed using the differentiation day 10-18 SHH treated group (FIG. 5C). At both 1 and 2 months after transplantation into neonatal mouse cortex, most human cells exhibited an undifferentiated appearance with bipolar or unipolar morphologies and continued to express NKX2.1. Furthermore, essentially all grafted cells expressed the neuronal precursor marker DCX, including those with multipolar morphologies. A large majority of the transplanted human interneuron precursors expressed GABA (e.g., 46/51 GFP+ cells are observable at the section surface). In contrast, co-labeling for parvalbumin (PV) or somatostatin (SST), two proteins detected in the major subclasses of NKX2.1-lineage interneurons, was not present. This result indicates that even by six weeks post-transplant, the NKX2.1-GFP+ cells had not yet differentiated into mature interneurons.

Although it is not necessary to understand the mechanism of a disclosed method it is believed that the apparent lack of differentiation of the grafted GFP+ cells in the mouse host cortex could be that NKX2.1 is downregulated following maturation, as occurs in mouse cortical interneurons (Marin et al., *J Soc Neurosci* 20:6063-6076 (2000)), resulting in the loss of GFP expression by the more differentiated cells. For example, sections were examined for expression of SC121, a human-specific pan-neuronal marker. Kelly et al., *Proc Natl Acad Sci USA* 101:11839-11844 (2004). As expected, all GFP+ cells also expressed SC121 (FIG. 6A-6D2). However, even at 6 weeks after transplantation, less than 10% of human cells expressed SC121 but not GFP (i.e., for example, 25 out of 372 GFP+ cells, counted from two 6 week transplants). In sum, perhaps due to the human interneuron precursor's tendency to follow a protracted pace of maturation in vivo, transplantation studies did not result in mature interneuron differentiation within the first two months of transplant.

Phenotypic and Synaptic Maturation of Cortical Interneurons In Vitro

Cortical interneuron development have been studied using a co-culture system in which mouse embryonic MGE-derived progenitors are plated over a "feeder culture" composed mainly of mouse cortical pyramidal neurons and glia. Xu et al., *J Neurosci* 24:2612-2622 (2004). To determine whether aspects of human interneuron maturation would be accelerated in this system relative to the xenografts, NKX2.1::GFP+ cells were collected by FACS at differentiation day 32 and replated onto cultures of dissociated embryonic mouse cortex (FIG. 7A). Cortical cells were isolated from embryonic day 13.5 mouse embryos; a stage prior to the migration into dorsal neocortex of the ventrally-derived cortical interneurons. Anderson et al., *Science* 278: 474-476 (1997).

Thus, this co-culture system mimics aspects of normal development with human NKX2.1+ cells developing in the presence of the glutamatergic cortical pyramidal neurons. Studies were performed in parallel using GFP+ cells derived from each of the three SHH treatment regimens (FIGS. 7B-7E).

Remarkably, in contrast to the in vivo studies, roughly 80% of the GFP+ cells from the differentiation day 10-18 SHH treated group ("MGE-like") versus 40% from the differentiation day 2-18 SHH treated group ("hypothalamic-like") and 15% from the differentiation day 6-18 SHH treated group, expressed GABA. Further, the differentiation day 6-18 SHH treated group was enriched in telencephalic (FOXG1+) cells and choline acetyltransferase (ChAT) but not the interneuron precursor LHX6. (See FIG. 4D).

GFP+ cells from the differentiation day 10-18 SHH treated cells were enriched for GABA neurons relative to the differentiation day 6-18 SHH treated cells. It was of interest to determine whether these cells would give rise to neurons that undergo GABAergic synaptic transmission. Whole-cell patch-clamp electrophysiological studies of identified GFP+

To further analyze synaptic inputs onto the NKX2.1:: GFP+ cells generated using the differentiation day 10-18 SHH treated group, spontaneous postsynaptic currents and localization of inhibitory or excitatory synaptic markers were analyzed. GFP+ cells cultured on the mouse cortical feeder cells for 30 days expressed high levels of vesicular GABA transporter (VGAT), present within the presynaptic terminal of GABAergic synapses. The subcellular localization of VGAT within GFP+ cells closely matched expression of the GABAergic postsynaptic marker gephyrin. (FIG. 8A-8E).

Figures 8A, 8B, 8C, 8D, 8E, 8F, 8G, 8H, 8I, 8J, 8K, 8L:
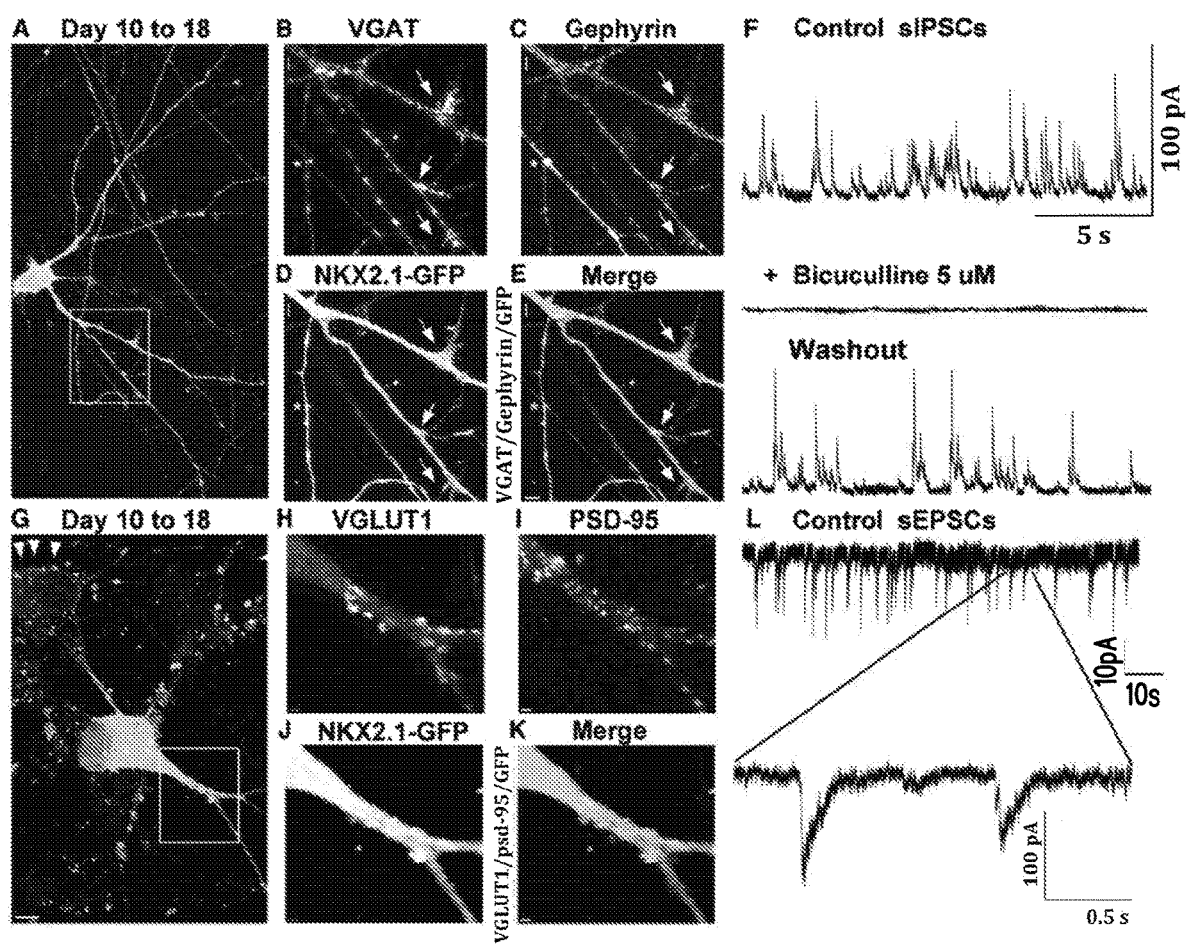
FIG. 8A-8L presents exemplary data showing that NKX2.1::GFP+ GABAergic interneurons receive both excitatory and inhibitory synaptic inputs.

Whole-cell patch clamp analyses demonstrated that NKX2.1::GFP+ cells receive spontaneous inhibitory postsynaptic currents (sIPSCs) which are reversibly blocked by the addition of the GABAA receptor antagonist bicuculline (FIG. 8F). In addition to inhibitory inputs NKX2.1::GFP+ cells also receive excitatory inputs, as demonstrated by the presence of vesicular glutamate transporter 1 (VGLUT1) expression adjacent to GFP+ putative dendrites, and colabeling with the post-synaptic excitatory synapse marker PSD-95 (FIGS. 8G-8K).

Consistent with the presence of glutamatergic synaptic inputs, spontaneous excitatory postsynaptic currents (sEPSCs) were also readily detected in the NKX2.1::GFP+ neurons (FIG. 8L). More detailed analyses on the spontaneous synaptic activities in NKX2.1::GFP+ cells are provided (FIG. 9A-9D; Tables 2A and 2B).

A) Electrophysiological Properties of hESC-Derived NKX2.1::GFP+ Neurons (Day 10-18 and Day 6-18 Group) on Mouse Versus Human Cortical Feeders.

|  | 10 to 18 on mouse feeder | | 6 to 18 on mouse feeder | | 10 to 18 on human feeder |
|---|---|---|---|---|---|
| DIV | 14-16 | 20-30 | 14-16 | 20-30 | 20-30 |
| RMP (mV) | −38.6 ± 2.4 | −65.6 ± 1.6** | −36.1 ± 2.4 | −62.6 ± 3.6** | −44.8 ± 6.6† |
| AP Amp (mV) | 57.4 ± 8.3 | 66.2 ± 4.1 | 56.2 ± 7.3 | 64.2 ± 5.1 | 62.5 ± 5.1 |
| AP Rise time (ms) | 1.472 ± 0.07 | 1.08 ± 0.03** | 1.52 ± 0.08 | 1.11 ± 0.09* | 1.9 ± 0.38† |
| AP ½ Width (ms) | 3.05 ± 0.06 | 2.42 ± 0.12* | 3.02 ± 0.05 | 2.5 ± 0.11* | 4.8 ± 0.32†† |
| AHP peak (mV) | 10.1 ± 3.5 | 15.6 ± 2.4 | 11.2 ± 3.5 | 16.3 ± 2.6 | 8.8 ± 3.72 |
| $R_I$ (GΩ) | 1.5 ± 0.1 | 0.72 ± 0.05** | 0.94 ± 0.05 | 0.68 ± 0.12 | 1.66 ± 0.2†† |
| No. of cells | 8 | 15 | 8 | 12 | 5 |

DIV: days in vitro; $R_I$: Input resistance; AP: action potential; AHP: after-hyperpolarization.
*P < 0.01, unpaired t-test, compared to corresponding 14-16 DIV group
**P < 0.001, unpaired t-test, compared to corresponding 14-16 DIV group
†P < 0.001, unpaired t-test, compared to 10 to 18 mouse (20-30 DIV)
††P < 0.0001, unpaired t-test, compared to 10 to 18 mouse (20-30 DIV)
Action potential properties were measured at threshold as elicited by current injection.

cells showed spontaneous firing in both differentiation day 10-18 SHH treated cells and differentiation day 6-18 SHH treated cells (FIGS. 7F-7K). However, only the differentiation day 10-18 SHH treated group showed modulation of the firing rate of NKX2.1::GFP+ cells in response to the GABAA receptor antagonist bicuculline (FIG. 7J). Since the cortical feeder cells contained only a very few murine interneurons in both the differentiation day 10-18 SHH treated group and the differentiation day 6-18 SHH treated group, these results indicate that hPSC-derived GABAergic neurons mediate the inhibitory synaptic output. Accordingly, in the differentiation day 6-18 SHH treated group in which GABAergic neurons are more rare, the firing rates following bicuculline exposure remained unchanged (FIG. 7C); and FIG. 7K, respectively.

B) Averaged Properties of GABAergic Synaptic Currents in GFP-Positive GABAergic Interneurons

|  | sIPSC | mIPSC |
|---|---|---|
| Amplitude (pA) | 62.6 ± 5.2 | 35.1 ± 2.3* |
| Rise time (ms) | 2.4 ± 0.3 | 2.3 ± 0.4 |
| Decay time (ms) | 66.2 ± 5.4 | 51.2 ± 3.6* |
| ½ width (ms) | 54.5 ± 5.3 | 41.3 ± 3.2* |
| No. of cells | 8 | 4 |

Recordings were made at 26-30 DIV.
*P < 0.05, unpaired t-test

Cortical interneurons include a diverse set of neuron types with distinct roles in cortical development and function.

Batista-Brito et al., *Curr Top Dev Biol* 87:81-118 (2009). The relatively rapid pace of maturation in this mouse cortical feeder system allows an assessment of the co-expression of other, more mature interneuron markers, and to define neurotransmitter phenotypes beyond GABA and ChAT in NKX2.1::GFP+ cells.

Figures 12A, 12B, 12C, 12D, 12E, 12F, 12G, 12H, 12I, 12J:
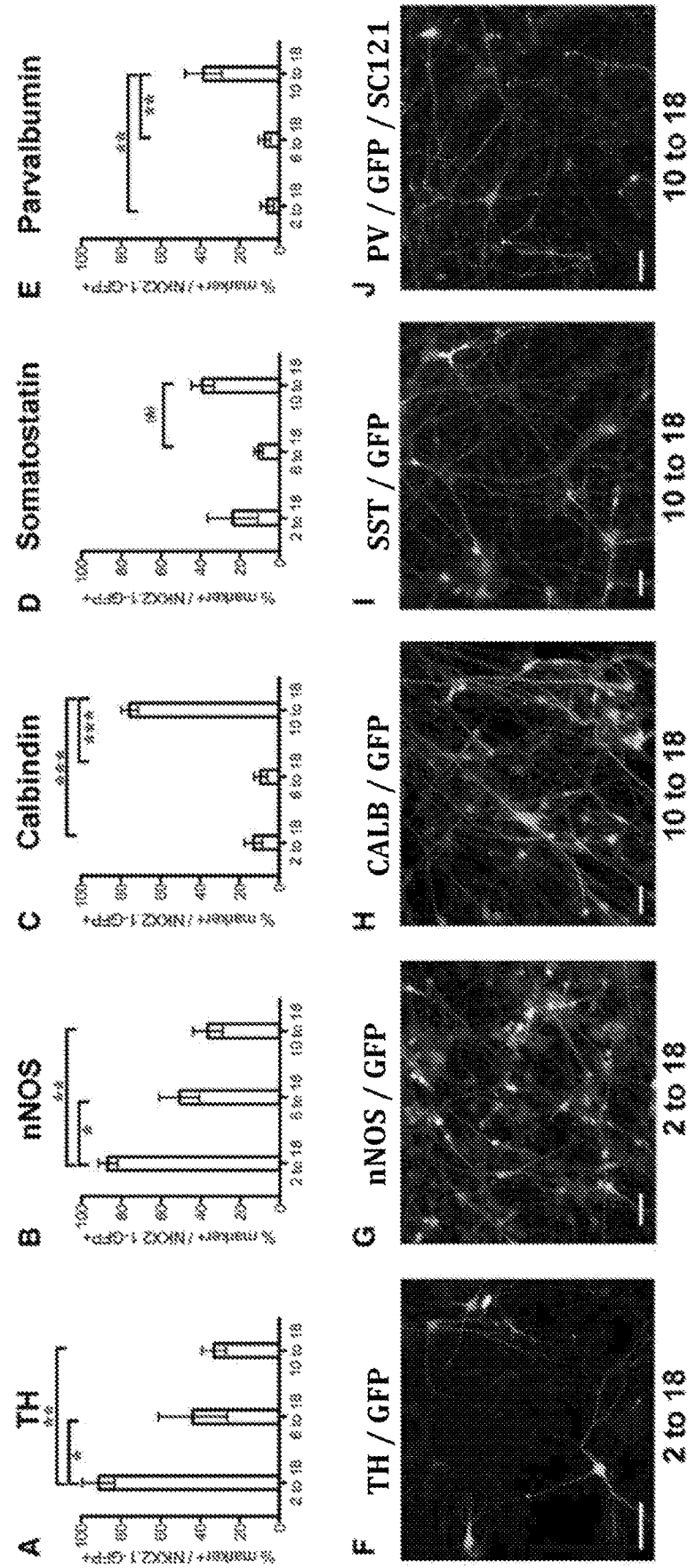
FIG. 12A-12J presents exemplary data showing the neurochemical profiling of NKX2.1::GFP+ Cells Grown on Mouse Cortical Feeders for 30 DIY Cells were labeled by immunofluorescence for the markers indicated, and the results were quantified in graphs (FIGS. 12A-12E: mean±SEM; *p<0.05, p<0.01, *p<0.001 using ANOVA followed by Scheffe test: (*) p<0.05 when compared directly to the 6-18 group; the p value did not reach significance in the standard Scheffe test: p=0.08). Representative images of cellular labeling are shown in (FIGS. 12F-12J). In the SHH 2 to 18 condition, most of the cells co-labeled with TH (FIGS. 12A and 12F) and nNOS (FIGS. 12B and 12G). In the 10 to 18 condition, many of the GFP+ cells co-labeled with calbindin (Calb.

For example, in the differentiation day 2-18 SHH treated group a large percentage of GFP+ cells expressing tyrosine hydroxylase (TH) was observed. (FIG. 12A). These data are consistent with the dopaminergic nature of many NKX2.1-lineage hypothalamic neurons. Yee et al., *J Comp Neurol* 517:37-50 (2009). Immunohistochemistry for nNOS and calbindin showed high percentages of nNOS cells in GFP+ cells from the differentiation day 2-18 SHH treated group while high percentages of calbindin+ neurons were present in the differentiation day 10-18 SHH treated group (FIGS. 12B and 12C, respectively). Other markers were also expressed that are characteristic of differentiated cortical interneurons, including SST and PV (FIGS. 12D and 12E). Each subgroup marker, co-expressed together with NKX2.1::GFP, was also identified. (FIGS. 12F-12J). VIP and calretinin were not expressed in these neuron cultures. These data suggest that a lack of cells exhibiting features such as the caudal ganglionic eminence during mouse development. Xu et al., *J Neurosci* 24:2612-2622 (2004).

The derivation of NKX2.1+IPV+ was particularly remarkable given the late developmental expression of this marker in cortical interneurons in vivo. Zecevic et al., *Dev Neurobiol* 71:18-33 (2011). Only a subset of the cells counted as GFP+ IPV+ by the automated image analyses (e.g., for example, using an Operetta high content scanner) showed high levels of PV expression and exhibited interneuron-like morphologies (about § % of total GFP+ cells (FIG. 12J). Although it is not necessary to understand the mechanism of an disclosure, it is believed that further optimization of the derivation of selective cortical interneuron subtypes would be useful, however, the data demonstrate that the presently disclosed co-culture strategy using embryonic mouse cortical neurons provides a successful platform to facilitate expression of subtype-specific neurochemical markers in hPSC-derived interneurons (e.g., for example, PV+hPSC-derived neurons).

Given the protracted maturation of NKX2.1-GFP+, putative interneuron precursors in vivo, it is surprising to obtain morphological, marker-based and physiological evidence of interneuron-like differentiation in the co-culture system. To determine whether the same GFP+ cells grown on cultures enriched for human cortical projection neurons would also show accelerated maturation, FACS-purified NKX2.1:: GFP+ cells were co-cultured in parallel either on mouse versus human cortical neurons.

Figures 10A, 10T:
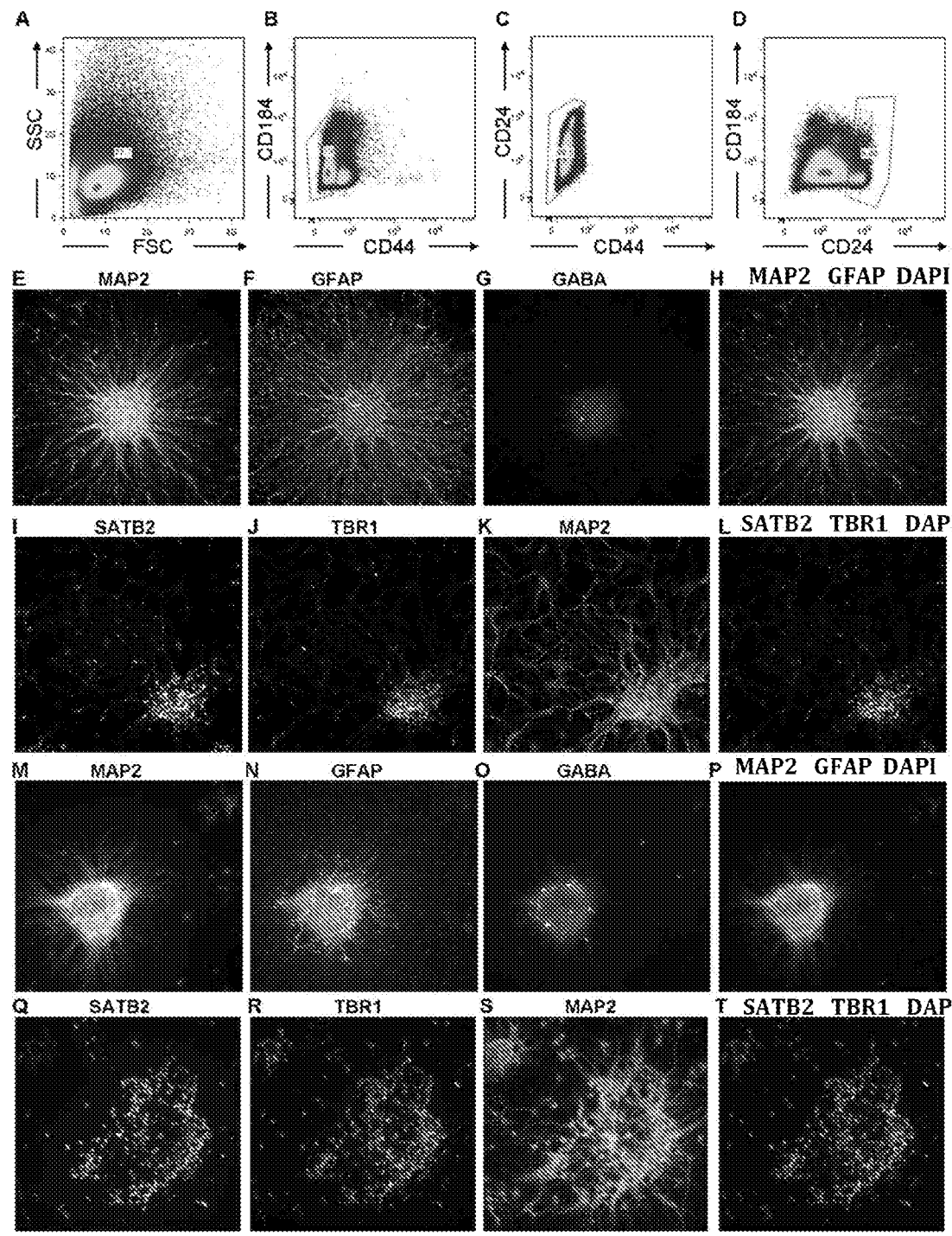
FIG. 10A-10T presents data from a representative phenotypic characterization of human ESC-derived versus primary mouse cortical feeder cells. Overall, comparable marker expression was seen between primary mouse and hESC derived cortical feeders.

The human cortical feeders were obtained upon differentiation of hESCs (e.g., for example, modified XLSB conditions) followed by FACS for CD44−/CD184+/CD24+ neurons (Yuan et al., *PLoS One* 6:7540 (2011)); (FIGS. 10A-10D). The cortical identity of the hESC-derived neurons was confirmed by the expression of VGLUT1, MAP2, CTIP2, and SATB2, with only very few GFAP+ or Nestin+ cells present (FIGS. 10E-10T).

Figures 11A, 11B, 11C:
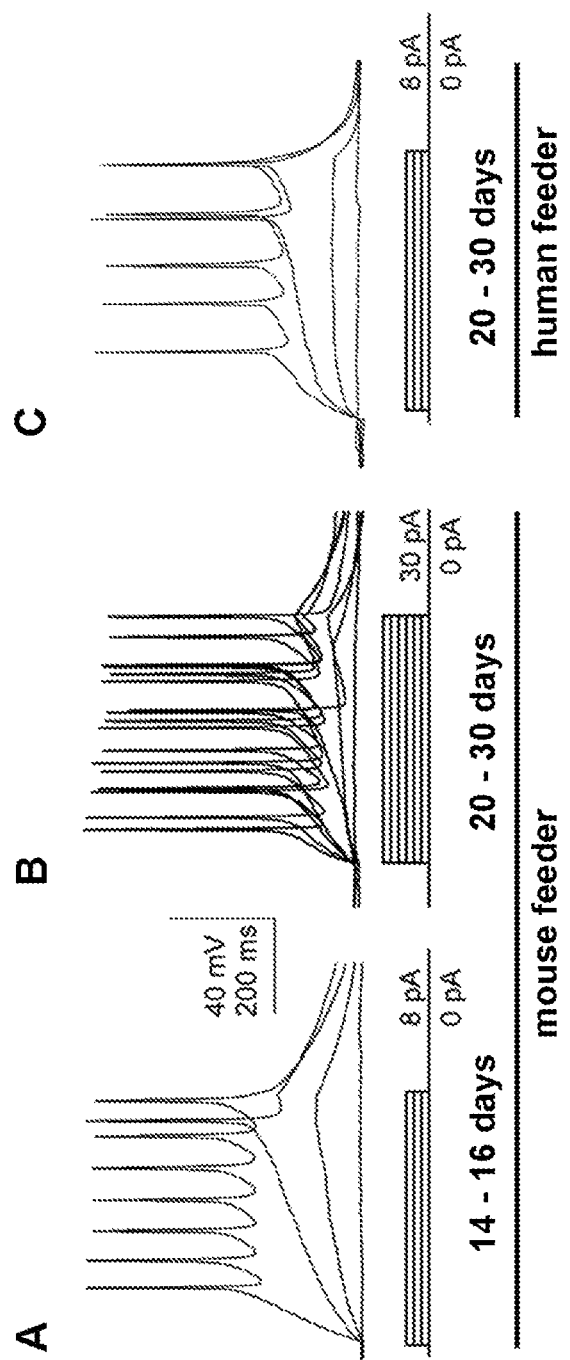
FIG. 11A-11C presents representative current clamp recordings from NKX2.1+ cortical interneurons.

A consistent difference was observed in electrophysiological maturation of NKX2.1+ cells plated on mouse versus human cortical feeders whether the recordings were obtained at either 14-16 DIV, 20-30 DN for the mouse feeder condition, or 20-30 DIV for the human cortical feeder condition (Tables 2A and 2B). Analysis of the basic electrophysiological properties of both the differentiation day 10 to 18 SHH treated group and the differentiation day 6 to 18 SHH treated group plated on mouse cortical feeder cells showed more mature characteristics at later time-points of differentiation. There was significant hyperpolarization of the resting membrane potential (RMP) with time, as well as a decrease in the input resistance. In addition, the action potentials became faster and narrower as evidenced by the decrease in the rise time and half width. In contrast, GFP+ neurons from the day 10-18 SHH treatment group that were recorded 20-30 DIY on the human cortical feeder cells retained relatively immature characteristics, comparable to the measurements seen in the younger 14-16 DIY neurons plated onto a mouse cortical feeder cells. For example, the RMP, action potential rise time, action potential half width, and input resistance in the differentiation day 10-18 SHH treated cells were significantly different when using the human cortical feeder cells as compared to mouse cortical feeder cells when recorded at the same DIY range. Sample traces depicting qualitative firing properties under the various conditions were collected. FIG. 11A-11C.

These data suggest that the pace of functional maturation is influenced by the local environment. Independent of mechanism, these data demonstrate that mouse cortical cell feeder co-culture conditions described herein allow for efficient maturation of hESC-derived cortical interneurons suitable for performing functional in vitro studies.

Compositions Comprising In Vitro Generated Cortical Interneurons, Hypothalamic Neurons, and Pre-Optic Cholinergic Neurons Within further embodiments, the present disclosure provides compositions comprising one or more in vitro differentiated neuronal cells that produce one or more markers of a cortical interneuronal cell and/or of a cortical interneuron precursor cell, wherein the in vitro differentiated neuronal cells are produced by: (a) contacting a multipotent cell or a pluripotent cell with two or more inhibitors of SMAD signaling, (b) contacting the multipotent cell or a pluripotent cell with one or more inhibitors of Wnt signaling, and (c) contacting the multipotent cell or a pluripotent cell with one or more activators of SHH signaling.

Composition disclosed herein can comprise a mixture of two or more cells wherein cortical interneurons comprise at least about 30% of the total number of cells, or at least about 40% of the total number of cells, or at least about 50% of the total number of cells, or at least about 60% of the total number of cells, or at least about 70% of the total number of cells, or at least about 80% of the total number of cells, or at least about 90% of the total number of cells, or at least about 95% of the total number of cells.

Compositions ca comprise a mixture of two or more cells wherein NKX2.1+/PV+ cortical interneurons comprise at least about 5%, or at least about 10%, or at least about 20%, or at least about 30%, or at least about 40%, or at least about 50% of the total number of cells in the composition.

Compositions can comprise a mixture of two or more cells wherein γ-aminobutyric acid (GABA)-ergic inhibitory interneurons comprise at least about 5%, or at least about 10%, or at least about 20%, or at least about 30%, or at least about 40%, or at least about 50% of the total number of cortical interneurons in the composition.

Within related embodiments, the present disclosure provides compositions comprising one or more in vitro differentiated neuronal cells that produce one or more markers of a hypothalamic neuron or a hypothalamic neuron precursor cell, wherein the in vitro differentiated neuronal cells are produced by: (a) contacting a multipotent cell or a pluripotent cell with two or more inhibitors of SMAD signaling, (b) contacting the multipotent cell or a pluripotent cell with one or more inhibitors of Wnt signaling, and (c) contacting the multipotent cell or a pluripotent cell with one or more activators of SHH signaling.

Composition can comprise a mixture of two or more cells wherein hypothalamic neurons comprise at least about 30% of the total number of cells, or at least about 40% of the total number of cells, or at least about 50% of the total number of cells, or at least about 60% of the total number of cells, or at least about 70% of the total number of cells, or at least about 80% of the total number of cells, or at least about 90% of the total number of cells, or at least about 95% of the total number of cells.

Compositions can comprise comprising one or more in vitro differentiated neuronal cells that produce one or more markers of a pre-optic cholinergic neuron or a pre-optic cholinergic neuron precursor cell, wherein the in vitro differentiated neuronal cells are produced by: (a) contacting a multipotent cell or a pluripotent cell with two or more inhibitors of SMAD signaling, (b) contacting the multipotent cell or a pluripotent cell with one or more inhibitors of Wnt signaling, and (c) contacting the multipotent cell or a pluripotent cell with one or more activators of SHH signaling.

Compositions can comprise a mixture of two or more cells wherein pre-optic cholinergic neurons comprise at least about 30% of the total number of cells, or at least about 40% of the total number of cells, or at least about 50% of the total number of cells, or at least about 60% of the total number of cells, or at least about 70% of the total number of cells, or at least about 80% of the total number of cells, or at least about 90% of the total number of cells, or at least about 95% of the total number of cells.

Cortical interneuron or interneuron precursor cells can be modified with a transgene expressing a detectable marker such as, for example, CT-2 or green fluorescent protein (GFP). It will be understood that these detectable markers can be interchanged with other detectable markers without deviating from this aspect of the present disclosure.

The cortical interneuron precursor cells of the present invention give rise to functional interneurons, exhibiting the morphological, neurochemical, and electrophysiological properties of mature interneurons. The immature interneuron precursor preparation can mature in vitro under controlled culture conditions mimicking their in vivo neuronal environment (e.g., cultured in the presence of feeder cells as described in the Examples herein). Alternatively, the immature interneuron precursor cells mature following transplantation and migration within the cerebral cortex of a mammalian subject (e.g., a human subject). As demonstrated herein, the immature interneuron precursor cells of the present invention migrate extensively, in a non-radial (i.e., tangential) fashion upon transplantation into the cerebral cortex. Upon migration, the cortical interneuron precursor cells mature into parvalbumin and Kv3.1 expressing interneurons that exhibit fast spiking action potential discharge patterns. Alternatively, the cortical interneuron precursor cells of the present invention mature into somatostatin expressing interneurons, exhibiting the characteristic rebound, adapting, non-fast spiking firing patterns of this sub-group of interneurons. These somatostatin expressing interneurons may further express neuropeptide Y.

The cortical interneuron precursor cells mature into interneurons having an average resting membrane potential of about −40 mV to about −70 mV. Overtime, the average resting membrane potential becomes more hyperpolarized, ranging from about −55 mV to about −70 mV.

Methods for the Treatment of Disorders and Disease

In vitro derivation of neuronal cells from stem cells or progenitor cells have significant clinical implications and are also important for disease modeling and drug screening. Conditions suitable for treatment in accordance with this method of the present invention include, without limitation seizure disorders, such as epilepsy or infantile spasms; neuropsychiatric disorders, such as autism, schizophrenia, an anxiety disorder, and an eating disorder; neurodevelopmental disorders, such as holoprosencephaly or microcephaly; and Parkinson's disease. Early studies using hPSCs have been primarily geared towards neurodegenerative disorders, which are known to affect specific neuron types such as midbrain dopamine neurons in Parkinson's disease (PD; (Kriks et al., *Nature* 480:547-551 (2011); Soldner et al., *Cell* 136:964-977 (2009); and Soldner et al., *Cell* 146:318-331 (2011)) or motor neurons in amyotrophic lateral sclerosis (ALS; Dimos et al., *Science* 321:1218-1221 (2008)) and spinal muscular atrophy (SMA; Ebert et al., *Nature* 457: 277-280 (2009)). More recent studies suggest the possibility of tackling complex neuronal disorders such as Schizophrenia (Brennand et al., *Nature* 473:221-225 (2011)) or autism-related syndromes (Marchetto et al., *Cell* 143:527-539 (2010) and Pasca et al., *Nat Med* 17:1657-1662 (2011)).

The cells of the present disclosure can be delivered via intraparenchymal or intraventricular transplantation as described in U.S. Pat. Nos. 5,082,670 and 5,650,148 to Gage et al., and U.S. Patent Publication No. 20060141622 to Johe et al., which are hereby incorporated by reference in their entirety. Intraparenchymal transplantation can be achieved by injecting the immature interneuron precursor cells within the host brain parenchyma or by preparing a cavity by surgical means to expose the host brain parenchyma and then depositing the cell graft into the cavity. Both methods provide parenchymal apposition between the grafted cells and host brain tissue at the time of grafting, and both facilitate anatomical integration between the graft and host brain tissue. Alternatively, the graft may be placed in a ventricle, e.g., a cerebral ventricle or subdurally, e.g., on the surface of the host brain where it is separated from the host brain parenchyma by the intervening pia mater or arachnoid and pia mater. Grafting to the ventricle may be accomplished by injection of the donor cells or by growing the cells in a substrate such as 30% collagen to form a plug of solid tissue which may then be implanted into the ventricle to prevent dislocation of the graft. For subdural grafting, the cells may be injected around the surface of the brain after making a slit in the dura. This is of importance if it is required that the graft become an integral part of the host brain and to survive for the life of the host.

Regardless of the survival issue, transplantations of neuronal cells and precursors described by the present disclosure result in the successful grafting of large numbers of cells that can be studied after their maturation in vivo.

Methods for the Treatment of Neurodegenerative Disorders and Disease

In certain embodiments, the present disclosure provides methods for the treatment of disorders and diseases that are associated with neurodegeneration including, for example, Parkinson's disease (PD) and Alzheimer's disease (AD), which methods comprise the in vivo administration of cortical interneurons to a patient afflicted with PD or AD, which cortical interneurons are generated by the methods disclosed herein.

The predominant differentiation of cholinergic neurons in NKX2.1::GFP+ progenitor cells of the differentiation day 6-18 SHH treatment group data described herein provides a basis for the modeling and treatment of disorders that are associated with loss of cognitive function. For example, in Alzheimer's disease basal forebrain cholinergic neurons are amongst the neurons most vulnerable during early stages of the disease. Whitehouse et al., *Science* 215:1237-1239 (1982).

The use of the NKX2.1::GFP reporter hESCs allowed optimization of differentiation protocols and the efficient conversion of nearly all hESC progeny to a FOXG 1+1NKX2.1+ ventral forebrain fate when SHH treatment was initiated at day 6 or later. Goulburn et al., *Stem Cells* 29:462-473 (2011). Because of the migratory ability of precursors of cortical interneurons, the present disclosure contemplates therapeutic advantages to the administration of cortical interneuron precursor cells either alone or in combination with the administration of mature cortical interneurons.

The data presented herein revealed several differences between human and mouse forebrain development including the human-specific expression of FOXA2 in hESC derived ventral forebrain progenitors and in CS15 human forebrain tissue. Without withing to be bound by theory, it is believed that transient FOXA2 expression may be related to a prolonged requirement for SHH signaling during human development. Thus, the protracted forebrain development in humans and differences in brain size between humans and mice may depend on the long-term proliferation of SHH dependent progenitors.

Species-specific differences in cortical interneuron development have been reported, which are based, in part, on the presence of ASCL1+ cells within the second trimester human fetal cortex. Letinic et al., *Nature* 417:645-649 (2002). Thus, it is believed that many, or even most, human cortical interneurons are generated within the cortex itself. Letinic et al., *Nature* 417:645-649 (2002). In contrast, studies in the mouse have demonstrated that most, if not all, murine cortical interneurons originate in the subcortical region. Fogarty et al., *J Neurosci* 27:10935-10946 (2007); Miyoshi et al., *J Neurosci* 30:1582-1594 (2010); and Xu et al., *J Neurosci* 24:2612-2622 (2004).

It was demonstrated as part of the present disclosure that expression of NKX2.1 is restricted within the ventral and dorsal forebrain in a CS15 human embryo. Moreover, the data presented herein demonstrate that hESC derived cortical interneurons precursors exhibit the capacity for tangential migration.

In contrast to murine cortical interneuron precursors, it was disclovered as part of the present disclosure that hESC-derived cortical interneurons persistently express NKX2.1. Marin et al., *J Soc Neurosci* 20:6063-6076 (2000). These data are consistent with in vivo findings in the human neocortex, which revealed the presence of post-mitotic NKX2.1+ neurons. Fertuzinhos et al., *Cereb Cortex* 19(9): 2196-2207 (2009). The data presented herein do not, however, rule out the possibility that a subset of our human ESC derived cells correspond to striatal interneurons, as those share markers of cortical interneurons in the mouse while retaining NKX2.1 expression. Marin et al., *J Soc Neurosci* 20:6063-6076 (2000).

Methods for the Treatment of Psychiatric Disorders and Disease

In other embodiments, the present disclosure provides methods for the treatment of psychiatric disorders and diseases including, for example, schizophrenia and the autism-related disorders.

Unlike in PD, ALS, or SMA, the neuron types critical for modeling schizophrenia or autism are less well defined, and no attempts have been made to direct neuron subtype identity in those studies. Great strides have been made recently in establishing protocols for the derivation of human ESC-derived cortical projection neurons. Espuny-Camacho et al., *Neuron* 77:440-456 (2013) and Shi et al., *Nat Neurosci* 15:477-486, S471 (2012).

However, inhibitory neurons, such as cortical interneurons may have a particularly important role in schizophrenia or autism. Insel, *Nature* 468:187-193 (2010) and Lewis et al., *Nat Rev Neurosci* 6:312-324 (2005). We have previously demonstrated the derivation of cortical interneurons using a Lhx6::GFP reporter mouse ESC line. Maroof et al., *J Neurosci* 30:4667-4675 (2010). However, the efficiency of cortical interneuron generation was low, and it was uncertain whether those conditions would apply for generating human cortical interneurons from PSCs. Modeling human cortical interneuron development in vitro is a particularly interesting challenge as the developmental origin of human cortical interneurons is controversial with studies suggesting that interneuron specification may differ considerably across mammalian species. Letinic et al., *Nature* 417:645-649 (2002) and Yu and Zecevic, *J Neurosci* 31:2413-2420 (2011). Furthermore, the protracted in vivo development of several cortical interneuron types (Anderson et al., *Neuroscience* 67:7-22 (1995)), represents another challenge for modeling their differentiation using human cells in vitro.

Current paradigms for the modeling and treatment of human psychiatric disease employ patient-specific iPSC-derived neurons. Brennand et al., *Nature* 473:221-225 (2011); Cheung et al., *Hum Mol Genet* 20:2103-2115 (2011); Chiang et al., *Mol Psychiatry* 16:358-360 (2011); Marchetto et al., *Cell* 143:527-539 (2010); and Pasca et al., *Nat Med* 17:1657-1662 (2011). Those published studies were, however, performed in mixed neural cultures of unclear neuronal subtype identity and with limited characterization of subtype specific synaptic and functional properties. A convergence of post-mortem findings have been exploited in an attempt to link genetic defects to psychiatric disorders, such as the interneuron-associated Erbb4 receptor in schizophrenia. Fazzari et al., *Nature* 464:1376-1380 (2010).

As disclosed herein, the present disclosure provides purified populations of mature cortical interneurons that may be used as models for human psychiatric disorders and diseases and in therapeutic regimen for the treatment of such psychiatric disorders and diseases. Moreover, the data presented herein demonstrate that highly efficient derivation of cortical interneurons is possible following timed exposure to developmental cues.

While not wishing to be bound by theory, it is believed that putative hESC-derived GABAergic interneurons receive synaptic inputs from other human interneurons and from excitatory mouse projection neurons. Cells exhibiting the neurochemical properties of cortical interneurons adopt fairly mature physiological properties within 30 days of plating on mouse cortex cultures. While the mechanisms of accelerated in vitro maturation of the NKX2.1::GFP+ neurons on mouse cortical cultures are currently unknown, the involvement of species-specific timing factors derive from the data presented herein. The presently disclosed data further demonstrate that synaptically active cortical interneurons can be derived in vitro, and can be useful for modeling and treatment of cortical interneuron pathologies in psychiatric disorders including, but not limited to, schizophrenia and autism.

The generation of hESC-derived PV expressing neurons and the presence of relatively rapid spiking, non-accommodating neurons in these cultures is of particular interest given the implications of PV interneuron dysfunction in schizophrenia. Beasley and Reynolds *Schizophr Res* 24:349-355 (1997) and Woo et al., *Am J Psychiatry* 154:1013-1015 (1997). Fast-spiking PV+ cortical interneurons are observed late during primate prenatal development and continue their maturation into early adulthood. Anderson et al., *Neuroscience* 67:7-22 (1995) and Insel, *Nature* 468:187-193 (2010). Given the role of PV+ neurons under various pathological conditions, the data presented herein support the modeling of such dysfunctional neuronal states and the treatment of those dysfunctional neuronal states by the administration of cortical interneurons and/or precursors thereof.

Thus, within certain aspects of these embodiments, the present disclosure provides the generation of enriched cortical interneuron subgroups, such as somatostatin+ and PV+ cells. MGE progenitors may be under control of SHH signaling, with high SHH signaling levels promoting the generation of somatostatin+ cells and lower SHH signaling levels promoting the generation of PV+ neurons. Xu et al., *Neuron* 65:328-340 (2010).

Methods for the Regeneration of Neuronal Tissues

In some embodiments, the present disclosure provides methods for generating a purified human in vitro derived cortical interneuron model for applications in regenerative medicine. The data presented herein illustrates a migratory potential of the hESC-derived cortical interneurons subsequent to transplantation into a neonatal mouse cortex. Thus, the cortical interneurons and their precursor cells produced by the present disclosure can be used in regenerative medicine.

Transplantation studies into several adult CNS models of disease identify problems that may be solved by using purified cortical interneuron grafts in: i) modulating pathological seizure activity (Baraban et al., *Proc Natl Acad Sci USA* 106:15472-15477 (2009)); ii) treating aspects of Parkinson's disease (Martinez-Cerdeno et al., *Cell Stem Cell* 6:238-250 (2010)); and iii) inducing learning and plasticity within the postnatal brain. Southwell et al., *Science* 327: 1145-1148 (2010). One specific challenge of previously reported transplantation studies is the protracted maturation of grafted hPSC-derived cortical interneuron precursors in vivo. Longer-term transplantation studies into the adult mouse cortex confirm slow maturation rates with NKX2.1+ putative interneuron precursors retaining immature growth cones and showing limited integration at 3 months post grafting (data not shown).

Consequently, previously reported data are in contrast with the presently disclosed in vitro co-culture work where rapid functional integration and phenotypic maturation was readily achieved. In some embodiment, the present disclosure provides a framework for the generation of distinct ventral prosencephalic neuron types that can be used to study various aspects of development. In one embodiment, the framework comprises an in vitro platform to study dysfunction of specific neuron types implicated in a myriad of neuropsychiatric diseases.

In Vivo Administration of Neuronal Cells and Compositions Thereof

Neuronal cells of the present disclosure, including cortical interneurons, hypothalamic neurons, and pre-optic chorionic neurons, may be administered in vivo to a patient by conventional means for achieving cellular transplantation. For example, neuronal cells may be transplanted by means of injection, such as intrathecal injection. Suitable methods of transplantation can be determined by monitoring the homing and engraftment of the implanted neuronal cells to the desired region of the central nervous system.

Since non-autologous cells may induce an immune reaction when administered in vivo, several approaches may be taken to reduce the likelihood of rejection of non-autologous neuronal cells. These include either administration of cells to privileged sites, or alternatively, suppressing the recipient's immune system, providing anti-inflammatory treatment which may be indicated to control autoimmune disorders to start with and/or encapsulating the non-autologous/semi-autologous cells in immune-isolating, semipermeable membranes before transplantation. Encapsulation techniques include microencapsulation, which involves small spherical vehicles, and macroencapsulation, which involves larger flat-sheet or hollow-fiber membranes. Uludag et al., *Adv Drug Deliv Rev* 42:29-64 (2000).

Methodology for preparing microcapsules are well known in the art and include, for example, those disclosed by Lu et al., *Biotechnol Bioeng* 70:479-83 (2000); Chang and Prakash, *Mol Biotechnol* 17:249-60 (2001); and Lu et al. *J Microencapsul* 17:245-51 (2000). For example, microcapsules can be prepared by complexing modified collagen with a ter-polymer shell of 2-hydroxyethyl methylacrylate (HEMA), methacrylic acid (MAA), and methyl methacrylate (MMA), resulting in a capsule thickness of 2-5 μm, which microcapsules can be further encapsulated with additional 2-5 μm ter-polymer shells in order to impart a negatively charged smooth surface and to minimize plasma protein absorption. Chia et al., *Biomaterials* 23:849-56 (2002).

Other microcapsules are based on alginate, a marine polysaccharide or a derivative thereof. Sambanis, *Diabetes Technol Ther* 5; 665-8 (2003). For example, microcapsules can be prepared by the polyelectrolyte complexation between the polyanions sodium alginate and sodium cellulose sulphate with the polycation poly (methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm. Canaple et al., *J Biomater Sci Polym Ed* 13:783-96 (2002). Moreover, nanoporous biocapsules with well-controlled pore sizes as small as 7 nm, tailored surface chemistries, and precise microarchitectures can be employed to immune-isolate cells during transplantation. Williams, *Med Device Technol* 10:6-9 (1999); Desai, *Expert Opin Biol Ther* 2:633-46 (2000).

Examples of immunosuppressive agents that may be used in conjunction with the in vivo administration of the presently disclosed neuronal cells include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Neuronal cell populations of the present disclosure can be isolated from the culture medium, and combined with a pharmaceutically acceptable carrier and/or with one or more additional agents that promote cell engraftment and/or functionality (e.g., immunosuppressing agents and antibiotics). Such neuronal cell populations can be administered in vivo in a pharmaceutically acceptable carrier or diluent, such as sterile saline and aqueous buffer solutions. The use of such carriers and diluents is well known in the art.

Neuronal cell compositions of the present disclosure may, if desired, be presented in a pack or dispenser device, such as an FDA-approved kit, which may contain one or more unit dosage forms containing the neuronal cells. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert.

Compositions comprising a preparation of neuronal cells formulated in a pharmaceutically acceptable carrier may also be prepared, placed in an appropriate container, and labeled for treatment of an indicated condition, as further detailed above. The cells prepared according to the methods of the present disclosure can be directly administered to the patient, may be seeded on a scaffold, and/or may be formulated in a pharmaceutical composition where the cells are mixed with suitable carriers or excipients.

As used herein, a "pharmaceutical composition" refers to a preparation of one or more of the neuronal cells described herein with other chemical components such as physiologically suitable carriers and excipients. The purpose of a pharmaceutical composition is to facilitate the in vivo administration of neuronal cells to a patient.

As used herein, the phrases "physiologically acceptable carrier" and "pharmaceutically acceptable carrier" are used interchangeably and refer to a carrier or a diluent that does not cause significant irritation to a patient and does not abrogate the biological activity and properties of the administered cells. The term "adjuvant" is encompassed by the phrases "physiologically acceptable carrier" and "pharmaceutically acceptable carrier."

As used herein, the term "excipient" refers to an inert substance added to a pharmaceutical composition to further facilitate administration of a neuronal cell. Examples of suitable excipients include calcium carbonate, calcium phosphate, various sugars and types of starch, cellulose derivatives, gelatin, vegetable oils, and polyethylene glycols.

Techniques for formulation and administration of neuronal cells may be found in "Remington's Pharmaceutical Sciences," (Mack Publishing Co., Easton, Pa.), which is incorporated by reference herein.

Suitable routes for in vivo administration will depend upon the disease or disorder being treated and may, for example, intrathecal, intravenous, or intraperitoneal injections. Alternately, pharmaceutical compositions may be administered systemically by, for example, injection of the pharmaceutical composition directly into a desired tissue region, such as a tissue region of the central nervous system, including the spinal column and/or brain of a patient.

Pharmaceutical compositions for use in accordance with the present disclosure may be formulated in a conventional manner using one or more physiologically acceptable carriers comprising excipients and auxiliaries, which facilitate processing of the neuronal cells into preparations that can be used pharmaceutically. Proper formulation is dependent upon the desired route of administration.

For injection, the neuronal cells of the pharmaceutical composition may be formulated in aqueous solutions, preferably in physiologically compatible buffers such as Hank's solution, Ringer's solution, and/or a physiological salt buffer. Penetrants that are appropriate for the barrier to be permeated, such as the blood brain barrier, can be used in the formulation. Such penetrants are well known and readily available in the art.

Pharmaceutical compositions suitable for use in the context of the present disclosure include compositions wherein the neuronal cells are contained in an amount effective to achieve the intended purpose. More specifically, a "therapeutically effective amount" means an amount of neuronal cells that are effective to prevent, alleviate, or ameliorate symptoms of a neurological disorder or disease, such as a neurodegenerative disease, a neuropsychiatric disease, or other neurological disease as discussed herein and/or to prolong the survival of the patient being treated. Determination of a therapeutically effective amount is well within the capability of those skilled in the art, especially in light of the detailed disclosure provided herein.

For any preparation used in the methods of the present disclosure, the dosage or the therapeutically effective amount can be estimated initially from in vitro cell culture assays. For example, a dose can be formulated in animal models to achieve a desired concentration. Such information can be used to more accurately determine useful doses in humans.

Toxicity and therapeutic efficacy of the neuronal cells described herein can be determined by standard pharmaceutical procedures in vitro or in experimental animals. The data obtained from these in vitro cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. Fingl et al., "The Pharmacological Basis of Therapeutics," Ch. 1, P. 1. (1975).

Depending on the severity and responsiveness of the neurological disease or disorder to be treated, dosing can be of a single or a plurality of administrations, with course of treatment lasting from several days to several weeks, or until cure is effected or diminution of the disorder or disease state is achieved. The amount of a composition to be administered will, of course, be dependent on the patient being treated, the severity of the affliction, the manner of administration, and the judgment of the prescribing physician. As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

EXAMPLES

Example 1

Induction of Forebrain Neural Progenitor Cells by the Combined Inhibition of SMAD and Wnt Signaling This Example demonstrates neural progenitor cell generation can be achieved by the combined of inhibition of SMAD and Wnt signaling and the activation of SHH signaling.

The first step in modeling development of cortical interneuron and other neuronal cells is the robust induction of forebrain type neural progenitors. Specification of anterior/forebrain fate is considered a default program during neural differentiation of hPSCs (Chambers et al., Nat Biotechnol 27:275-280 (2009); Eiraku et al., Cell Stem Cell 3:519-532 (2008); Espuny-Camacho et al., Neuron 77:440-456 (2013); Gaspard et al., Nature 455:351-357 (2008)). However, not all cell lines adopt neural and anterior fates at equal efficiencies. Kim et al., Cell Stem Cell 8:695-706 (2011) and Wu et al., Proc Natl Acad Sci USA 104:13821-13826 (2007). Patterning factors secreted within differentiating cultures such as fibroblast growth factors (FGFs), Wnts or retinoids can suppress forebrain induction and trigger the induction of caudal cell fates. We recently reported that early, high-dose SHH treatment also suppresses forebrain markers such as FOXG1 via inhibition of DKK1 induction, which results in the derivation of hESC derived floor plate like cells. Fasano et al., Cell Stem Cell 6:336-347 (2010). This is a concern for deriving cortical interneurons that are thought to require strong SHH activation at the NKX2.1+ progenitor stage. Xu et al., J Neurosci 24:2612-2622 (2004) and Xu et al., Neuron 65:328-340 (2010). Here we tested whether pharmacological inhibition of WNT signaling can improve FOXG1 induction and subsequently enable the controlled, SHH-mediated ventralization towards NKX2.1+ forebrain progenitor fates. FIG. 1A.

Human ESC (lines WA-09, HES-3 (NKX2.1::GFP) and iPS cells (C72, SeV6) were maintained on mouse embryonic fibroblasts (MEFs) as described previously and dissociated with Accutase (Innovative Cell Technologies) for differentiation or dispase for passaging (Chambers et al., Nat Biotechnol 27:275-280 (2009)). Media used for differentiation included KSR-medium, N2 medium (DMEM/F12 with NaHCO3, N2B supplement (Stem Cell Technologies), and Neurobasal media with B27 (Gibco) and N2 supplements (Invitrogen) as described previously. Kriks et al., Nature 480:547-551 (2011). The small molecules compounds used included: XAV939 (2 µM; Stemgent), LDN193189 (100 nM; Stemgent), SB431542 (10 µM; Tocris), and Purmorphamine (1-2 µM; Calbiochem), ascorbic acid (200 µM) and dibutyryl-cyclic AMP (dbcAMP, 200 µM; both from Sigma). Recombinant growth factors: SHH (C25II; 50-500 ng/ml), Noggin (125 ng/ml), DKK1 (250 ng/ml), and BDNF (10 ng/ml) were purchased from R&D Systems or for FGF2 (10 ng/ml) from Promega and used at the concentrations indicated in the manuscript.

Cortical feeder cell cultures were prepared by dissociating the dorsal cortices from 250 µm coronal slices of E13.5 mouse brain, and cultured as described previously. Xu et al., Neuron 65:328-340 (2010). For human cortical feeder preparation, cells were subjected to XLSB-mediated neural induction, with the addition of the SHH antagonist cylcopamine (5 µM) from days 8-10. At day 18, cells were dissociated with accutase and replated (80,000-100,000 cells/cm2). At day 32 FACS was used to purified cells that were CD44-FITC negative (Abeam), CD24-PE positive (BD Pharmingen), and CD184-APC positive (R&D Systems) (Yuan et al., PLoS One 6:7540 (2011)). The purified cells were then plated at 20,000 cells/cm2 on matrigel coated wells for further studies. NKX2.1::GFP+ cells were plated at 4,000 cells/cm2 on cortical feeder cultures prepared 4-7 days earlier. After 5-7 days of co-culture when cells reached 70-80% confluence, the mitotic inhibitor mitomycin C (1 µM; Sigma) was added to the culture for 2 hours and subsequently replaced with fresh medium.

Cultures were fixed in 4% paraformaldehyde in phospate-buffered saline and processed for immunofluorescent staining and confocal microscopy. Secondary antibodies used for primary antibody detection were species-specific Alexa-dye conjugates (Invitrogen). For primary antibodies, we used antibodies to rabbit FOXG1 (gift from Eseng Lai); mouse PAX6 (DSHB); mouse NKX2.1 (Labvision); goat NKX2.1 (C-20, Santa Cruz); rabbit OLIG2 (Chemicon); goat FOXA2 (Santa Cruz); rabbit LHX6 (Abeam); mouse RAX (Abnova); rabbit GAPDH (Thermo Scientific); goat DCX (Santa Cruz); mouse TUJ1 (Covance); rabbit GABA (Sigma); mouse Nestin (Thermo Scientific); rabbit KI67 (Labvision); mouse KI67 (Dako); rabbit Calbindin (Chemicon); mouse Calretinin (Swant); chick GFP (Abeam); goat Chat (Chemicon); rat somatostatin (Chemicon); mouse TH (Abeam); rabbit NOS (Swant); mouse Parvalbumin (Chemicon); mouse PSD-95 (Zymed); guinea-pig VGLUT1 (Synaptic systems); rabbit VGAT (Synaptic systems); and mouse Gephyrin (Synaptic Systems).

FOXG1 and PAX6 quantification: Using a 20× objective, 25 fields were imaged from 3 wells and from 4 independent differentiation studies. The number of DAPI+ nuclei was used as the denominator and either FOXG1+ nuclei or PAX6+ nuclei were used for the numerator. NKX2.1::GFP co-labeling: Using a 20× objective, 25-30 fields were imaged from 4 wells from 4 independent differentiations. The number of NKX2.1::GFP+ cells was used as the denominator and the numerator chosen for each analyzed marker. As a control for each marker, secondary antibody in the absence of primary antibody was used as a negative control to designate signal specificity.

For all experiments analysis was derived from at least three independent experiments. Statistical analysis was performed using ANOVA followed by a Dunnett test to quantify treatment impact as compared to predefined control condition.

Neural differentiation of hESCs via the dual SMAD-inhibition protocol (Chambers et al., Nat Biotechnol 27:275-280 (2009)) using Noggin+SB431542 (NSB) robustly induced FOXG1+/PAX6+ precursors. The differentiation protocol in the dual SMAD inhibition paradigm to generate anterior neural progenitors is shown in FIG. 1A (NSB: Noggin+ SB431542. LSB: LDN193189+SB31542). Replacement of Noggin with the ALK2/3 inhibitor LDN- 193189 (LSB) induced PAX6 expression equally well but showed a trend towards a reduction in the percentage of cells expressing FOXG1 (FIGS. 1B and 1C;  p<0.01; * p<0.001; using ANOVA followed by Scheffe test). Adding recombinant DKK1 or the tankyrase inhibitor XAV939. Huang et al., *Nature* 461:614-620 (2009). Both potent inhibitors of canonical Wnt signaling, greatly enhanced FOXG1 expression in LSB-treated cultures. FIGS. 1B-1D.

FIG. 1D is a representative immunofluorescent image for FOXG1 and PAX6 expression at day 10 following XLSB treatment. Importantly, the effect of XAV939 on FOXG1 induction was consistent (FIG. 1E) across multiple independent hESC (HES-3 and WA-09) and human iPSC lines (C72 line (Papapetrou et al., *Proc Natl Acad Sci USA* 106:12759-12764 (2009)), SeV6. Kriks et al., *Nature* 480:547-551 (2011). FIG. 1E demonstrates that robust telencephalic specification using XLSB was achieved at comparable efficiencies in human induced pluripotent stem cells (hiPSC lines SeV6, C72; n=4). The use of three small molecules (XAV939, LDN-193189, and SB431542; which are collectively referred to as XLSB) permits the rapid and robust induction of forebrain fates across human ESCs and human iPSCs.

The induction of ventral fates was tested with XLSB in the presence of SHH activators (FIG. 1A). FIGS. 1F-1H show that the addition of SHH signaling to the XLSB protocol significantly enhanced the production of NKX2.1::GFP expressing progenitors. Using a previously established NKX2.1::GFP knock-in reporter hESC line (Goulburn et al., *Stem Cells* 29:462-473 (2011)), GFP induction was observed by day 10 following activation of the SHH pathway by recombinant SHH (R&D Systems, C-25II) and the smoothened activator purmorphamine (FIG. 1F). Maximal induction of NKX2.1::GFP was found at day 18 upon treatment with purmorphamine at 1 µM and with SHH at 5 nM (FIG. 1G), which is referred to as "SHH" herein.

The data presented in FIG. 1F demonstrates that 5 nM SHH (Sonic C24II) and 1 µM Purmorphamine, added from day 4, exhibited synergistic effects in inducing NKX2.1::GFP production at day 10 (* p<0.001; compared to SHH). A range of concentrations of SHH and purmorphamine were compared at day 18 in FIG. 1G. Co-treatment was greatly superior to quite high concentrations of either SHH or purmorphamine alone (* p<0.001; compared to no SHH using ANOVA followed by Scheffe test). FIG. 1H demonstrates that delaying the timing of SHH exposure from about 2 days to about 10 days of differentiation did not dramatically affect the efficiency of NKX2.1::GFP induction measured at day 18 (*** p<0.001 compared to 0-18 using ANOVA followed by Scheffe test. P: purmorphamine, S: Sonic hedgehog). The transcription factor NKX2.1 is a marker of ventral prosencephalic progenitor populations. Sussel et al., *Development* 126:3359-3370 (1999) and Xu et al., *J Neurosci* 24:2612-2622 (2004).

The data presented in this Example confirm that an, inhibitor of WNT activity, such as recombinant DKK1, can be used to induce the generation of telencephalic and optic progenitors during mouse and human ESC differentiation. Lamba et al., *Proc Natl Acad Sci USA* 103:12769-12774 (2006); Meyer et al., *Stem Cells* 29:1206-1218 (2011); and Watanabe et al., *Nat Neurosci* 8:288-296 (2005).

Moreover, as demonstrated herein, the tankyrase-inhibitor XAV939 (Huang et al., *Nature* 461:614-620 (2009)) can replace recombinant DKK1 in a dual-SMAD inhibition protocol. The use of three small molecules (i.e., XLSB) results in robust induction in multiple cell lines. It was demonstrated as part of the present disclosure that XLSB may be advantageously employed for inducing the generation of cortical interneurons as wall as a broad range of other forebrain cell types.

Previous studies on the derivation of hESC derived floor plate cells demonstrated that early treatment with SHH (day 1 of differentiation) is critical for the efficient induction of FOXA2. Fasano et al., *Cell Stem Cell* 6:336-347 (2010). As disclosed herein, cells that were exposed to SHH at late differentiation stages (day 10 of the XLSB protocol) remain competent for inducing NKX2.1::GFP as measured by FACS. FIG. 1H. Therefore, XLSB and SHH can be combined to induce the high efficiency generation of NKX2.1+ progenitor cells.

Example 2

Induction of Distinct Ventral Progenitor Populations by Altering the Timing of SHH Activation This Example demonstrates that distinct ventral progenitor cell populations can be generated by altering the timing of SHH activation of neuronal cells.

Figures 2A, 2B, 2C, 2D, 2E, 2F, 2G, 2H, 2I, 2J, 2K:
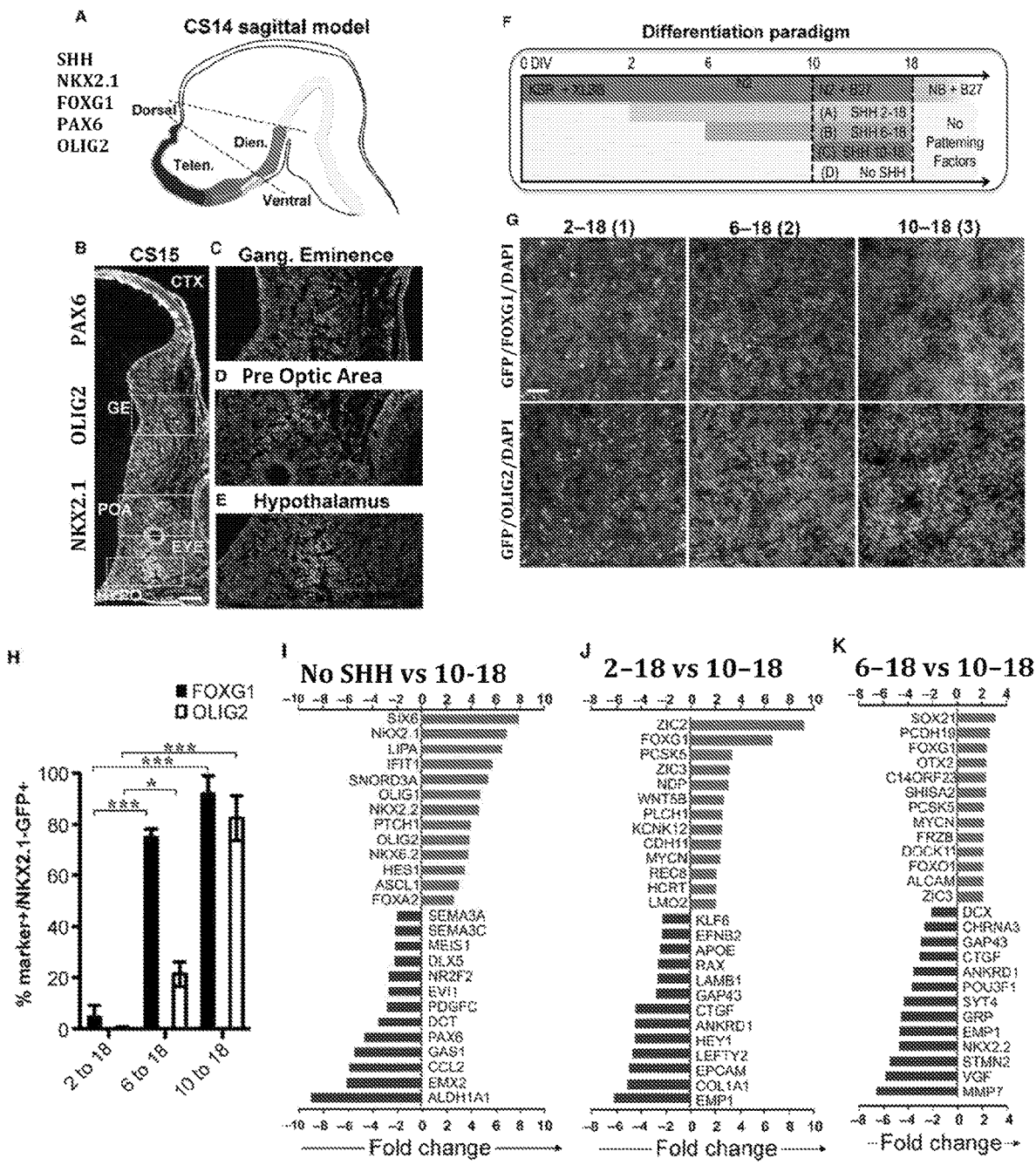
FIG. 2A-2K presents data demonstrating that the timing of SHH exposure determines the regional identity of NKX2.1::GFP expressing progenitors.

The efficient induction of NKX2.1 largely independent of the timing of SHH exposure from Example 1 raised the question of whether timing impacts the subtype of NKX2.1+ neural progenitor generated. Analogous to rodents, NKX2.1 is expressed during early neural human development in both the FOXG1+ telencephalon as well as in the FOXG1-negative ventral diencephalon. FIG. 2A shows a model of human prosencephalon (sagittal view at Carnegie stage 14 (CS14)) with expression of forebrain patterning markers based on published data. Kerwin et al., *J Anat* 217:289-299 (2010) and Rakic and Zecevic, *Cereb Cortex* 13:1072-1083 (2003). During embryonic mouse development NKX2.1 expression in the telencephalon (FOXG1+) is restricted to the ventral (subcortical) domain. In contrast, reports in human fetal tissue suggested that NKX2.1 may not be restricted to the ventral forebrain, instead extending into the dorsal forebrain and cortical anlage. Rakic and Zecevic, *Cereb Cortex* 13:1072-1083 (2003) and Yu and Zecevic, *J Neurosci* 31:2413-2420 (2011). However, those studies were largely based on the analysis of second trimester human fetuses that makes it difficult to distinguish whether NKX2.1+ cells were indeed induced in the dorsal forebrain or migrated dorsally after induction in the ventral domain. Fertuzinhos et al., *Cereb Cortex* 19(9):2196-2207 (2009).

By performing immunocytochemical analyses in early stage human embryos (Carnegie Stage 15, ~38 days post conception), we observed restriction of NKX2.1 expression to the ventral forebrain (FIG. 2B-2E) comparable to the developing mouse CNS. FIG. 2B-2E show that coronal (oblique) hemisection of the human prosencephalon at Carnegie stage 15 (CS15) demonstrates the expression of NKX2.1, OLIG2, and PAX6. NKX2.1 and OLIG2 are expressed in various regions throughout the ventral prosencephalon, whereas PAX6 is restricted to the dorsal prosencephalon and the eye. The expression of these proteins is non-overlapping, except in the ganglionic eminence (FIG. 2C) where OLIG2 and NKX2.1 are co-expressed. The scale bar in (FIG. 2B) represents 200 µm. The NKX2.1 domain in the human embryonic ventral forebrain was further subdivided into an OLIG2+ ganglionic eminence and an OLIG2-negative preoptic area anlage (FIG. 2C, 2D). The differentiation paradigm for this Example is shown in FIG. 2F.

Tissue derived from aborted human fetuses was obtained from the Department of Gynecology, University Bern, Switzerland. The study was approved by the Ethics Committee of the Medical Faculty of the University of Bern, Switzerland and the Ethics Committee of the State Bern, Switzerland (No. 52/91, 71/94, 188/95). Written consent was given by the women seeking abortion.

All cells were dissociated using accutase (Stem cell technologies) for thirty minutes, then resuspended in Neurobasal/B27 with Y27632 (10 □M; Tocris) and sorted on a BD FACS Aria II (SSC gating/FSC gating/DAPI negative exclusion gating for live cells). For post-sort analysis, data was processed using FlowJo (Treestar) software.

Total RNA was isolated at day 18 of differentiation from FACS sorted NKX2.1::GFP+ cells from three varying differentiation conditions and a "No SHH" condition that did not contain any GFP-expressing cells (Trizol, Sigma). Samples for each group in triplicate were processed for Illumina bead arrays (Illumina HT-12) by the MSKCC genomics core facility according to the specifications of the manufacturer.

To address whether in vitro timing of SHH exposure affects the regional identity of the resulting hPSC-derived NKX2.1::GFP+ cells, the identity of sorted cells was observed at day 18 of differentiation following SHH treatment either from day 2-18, day 6-18, or day 10-18 (FIG. 2F). In agreement with previous results on floor plate induction (Fasano et al., *Cell Stem Cell* 6:336-347 (2010)), early SHH exposure (2-18 days) suppressed FOXG1 induction (FIG. 2G, left panel) despite robust induction of NKX2.1::GFP. See FIG. 1H. Immunofluorescence for OLIG2 and FOXG1 in NKX2.1::GFP line at day 18 of differentiation are presented in FIGS. 2G and 2H.

Treatment with SHH after day 6 (6-18 and 10-18 group) significantly increases the percentage of NKX2.1::GFP+ cells that coexpress FOXG1 as quantified in (FIG. 2H). Treatment with SHH after day 10 (10-18 group) enhanced the derivation of NKX2.1::GFP+ cells co-expressing OLIG2, (* $p<0.05$, *** $p<0.001$, compared to 2-18 using ANOVA followed by Scheffe test). Expression of FOXG1, NKX2.1 and OLIG2 indicates a pattern characteristic of ganglionic eminence. Tekki-Kessaris et al., *Development* 128:2545-2554 (2001). In contrast both 6-18 and 10-18 treatment groups showed expression of FOXG1, but differed in OLIG2 expression (FIG. 2G, middle and right panels). We hypothesize that differential expression of FOXG1 and OLIG2 reflect the distinct NKX2.1+ precursor domains observed during early human development (FIG. 2A-2E) and mimic the Olig2+ domains during mouse forebrain development. Flames et al., *J Neurosci* 27:9682-9695 (2007). More than 90% of the NKX2.1::GFP+ cells in the 6-18 and 10-18 protocol coexpressed FOXG1 and nearly 80% of the GFP+ cells in the 10-18 protocol co-expressed OLIG2. FIG. 2H.

The impact of timing of SHH exposure on the derivation of specific ventral precursor populations was further examined by global transcriptome analysis (FIG. 2I-2K, all raw data are available on GEO: http://www.ncbi.nlm.nih.gov/geo/: Accession # pending). FIG. 2I-2K show microarray data from cells sorted for NKX2.1::GFP expression at day 18 of differentiation, comparing gene expression levels between the SHH day 10-18 protocol versus no SHH (FIG. 2I), day 10-18 versus day 2-18 protocol (FIG. 2J), and day 10-18 versus 6-18 protocol (FIG. 2K). Red bars indicate genes expressed at higher levels in the SHH 10-18 protocol, blue bars indicate genes expressed at lower levels in day 10-18 protocol. All changes are significant at $p<0.001$ (see for additional details).

A direct comparison of day 10-18 versus untreated cultures (No SHH) confirmed the robust induction of ventral specification markers such as NKX2.1, NKX2.2, ASCL1, SIX6, OLIG2, and NKX6.2, which were induced at the expense of dorsal forebrain markers such as EMX2 and PAX6 (FIG. 2I). There were no significant differences in the expression of general anterior markers such as FOXG1 and OTX2 (FIG. 2I), supporting the notion that both populations are of forebrain identity. Comparison of day 10-18 to day 2-18 treated cultures (FIG. 2J) illustrated differences in the expression of anterior markers such as FOXG1 versus diencephalic markers such as RAX In contrast, day 10-18 versus day 6-18 treated cultures showed less pronounced differences in forebrain marker expression (FIG. 2K). Overall, our data demonstrate that the window of SHH treatment significantly impacts the regional identity of hPSC-derived NKX2.1 precursors.

Figures 3A, 3B, 3C, 3D, 3E, 3F:
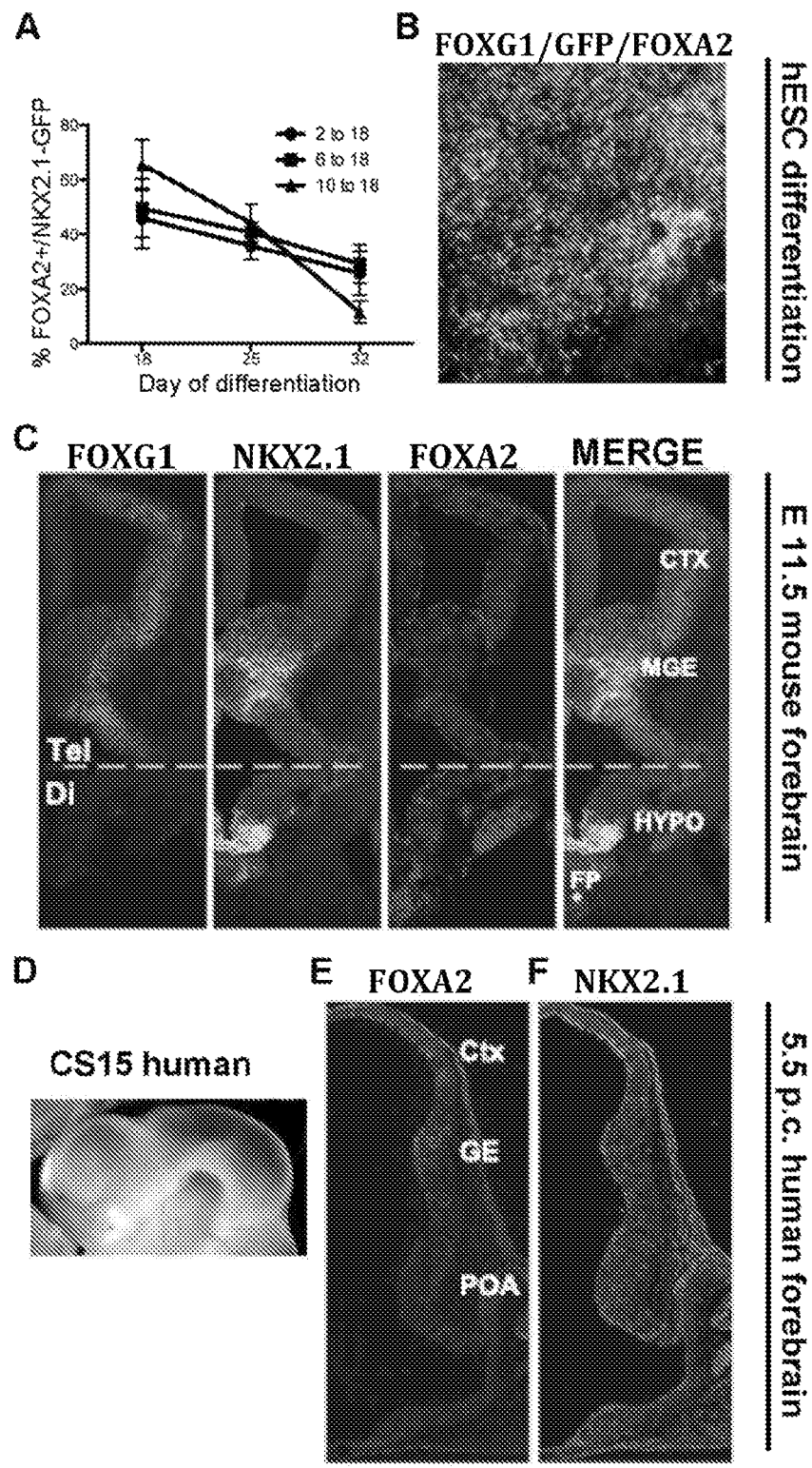
FIG. 3A-3F presents exemplary data showing that FOXA2 is transiently expressed in the hPSC derived NKX2.1+ lineages and in the human ganglionic eminence.

One surprising finding from the gene expression data was the induction of FOXA2 in all SHH treated cultures including the day 10-18 group (FIG. 2I). Supplementary FIG. 1A-1H (FIG. 3A-3F) shows that FOXA2 is transiently expressed in the hPSC derived NKX2.1+ lineages and in the human ganglionic eminence. FIG. 3A shows time course of FOXA2 expression after sorting differentiated NKX2.1:: GFP expressing cells at day 18, then culturing the cells in the absence of SHH signaling for two additional weeks. The percentage of FOXA2 co-labeling decreases over the course of two weeks. FIG. 3B shows representative immunocytochemistry image of day 10-18 treated cultures. Expression of FOXG1 and co-expression of FOXA2 and GFP at day 18 of differentiation. FIG. 3C shows embryonic day 11.5 coronal section of a developing mouse brain showing the expression of FOXG1 (red), NKX2.1 (green), and FOXA2 (D'Amato et al., *Proc Natl Acad Sci USA* 84:4322-4326 (1987)). There is no expression of FOXG1 in the diencephalon (Di) and there is no FOXA2 expression in the telencephalon (Tel).

NKX2.1 is expressed in the medial ganglionic eminence (MGE) and the hypothalamus (HYPO), but is not expressed in the floor plate (FP) and does not co-label with FOXA2. FIG. 3D shows Carnegie stage 15 (CS15; approximately 5.5 gestational weeks) human embryo sectioned for immunohistochemical analysis. E,F) Adjacent coronal (oblique) hemisections of the human CS15 prosencephalon demonstrating the expression of FOXA2 and NKX2.1. While FOXA2 appears to be specifically expressed in the ganglionic eminence (FIG. 3E) NKX2.1 is expressed in various regions of the ventral prosencephalon (FIG. 3F). FIG. 3A-3F demonstrates differences in FOXA2 expression between human and mouse, suggestive of an alternative mechanism to generate NKX2.1 progenitors in the ventral forebrain. However, FOXA2 expression in these NKX2.1 cells may be transient as shown in vitro (FIG. 3A) and as suggested by in situ hybridization analyses of later stage human embryos (Allen Brain Atlas, http://human.brain-map.org/).

Thus, expression of FOXA2, a marker thought to be largely restricted to the floor plate within the developing CNS, was confirmed at day 18 of differentiation in NKX2.1:: GFP+ cells of all three SHH treatment paradigms (FIGS. 3A and 3B). To address whether FOXA2 expression may represent an in vitro artifact following strong extrinsic activation of SHH signaling, or whether FOXA2 expression occurs in the telencephalon during in vivo development, we performed histological analyses in the developing mouse and human forebrain. In mouse embryos (E11.5) FOXA2 expression within the mouse prosencephalon was segregated from the FOXG1 and NKX2.1 domains (FIG. 3C). However, immunohistochemical analysis for FOXA2 in primary human forebrain tissue (CS15 embryo) confirmed expression in the anlage of the telencephalic NKX2.1+ ganglionic eminence (FIGS. 3D-3F). These data suggest at least transient FOXA2 expression occurs during human ventral forebrain development in agreement with the in vitro hPSC differentiation data.

TABLE S1

Fold Changes and Significance of Differentially Expressed Transcripts

| day 10-18 versus no SHH | | | day 10-18 versus day 2-18 | | | day 10-18 versus day 6-18 | | |
|---|---|---|---|---|---|---|---|---|
| Probeset | F-Change | p-value | Probeset | F-Change | p-value | Probeset | F-Change | p-value |
| SIX6 | 7.88 | 6.35E−09 | ZIC2 | 9.25 | 1.56E−09 | SOX21 | 3.14 | 3.37E−07 |
| NKX2-1 | 6.92 | 3.40E−10 | FOXG1 | 6.70 | 6.70E−05 | SP8 | 2.81 | 1.40E−08 |
| LIPA | 6.47 | 8.53E−09 | PCSK5 | 3.39 | 3.35E−05 | PCDH19 | 2.65 | 2.29E−06 |
| IFIT1 | 5.73 | 5.21E−09 | ZIC3 | 3.19 | 2.25E−04 | FOXG1 | 2.39 | 6.69E−05 |
| SNORD3A | 5.37 | 4.69E−07 | NDP | 3.12 | 2.76E−04 | OTX2 | 2.38 | 5.20E−08 |
| OLIG1 | 4.70 | 2.51E−07 | WNT5B | 2.66 | 2.90E−04 | C14ORF23 | 2.37 | 5.84E−06 |
| NKX2-2 | 4.62 | 8.69E−09 | PLCH1 | 2.56 | 1.52E−05 | SHISA2 | 2.36 | 6.38E−05 |
| PTCH1 | 3.96 | 2.07E−06 | KCNK12 | 2.54 | 2.74E−04 | PCSK5 | 2.19 | 1.67E−05 |
| OLIG2 | 3.90 | 1.15E−05 | CDH11 | 2.44 | 4.13E−05 | MYCN | 2.19 | 1.14E−05 |
| NKX6-2 | 3.74 | 2.12E−07 | MYCN | 2.41 | 2.18E−06 | FRZB | 2.12 | 6.43E−05 |
| HES1 | 3.46 | 2.42E−09 | REC8 | 2.08 | 1.04E−04 | DOCK11 | 2.11 | 2.29E−04 |
| ASCL1 | 3.00 | 1.42E−06 | HCRT | 2.08 | 3.20E−04 | FOXO1 | 2.08 | 1.74E−04 |
| FOXA2 | 2.63 | 6.86E−07 | LMO2 | 2.06 | 2.05E−05 | ALCAM | 2.08 | 3.61E−04 |
| SEMA3A | −2.00 | 4.75E−04 | KLF6 | −2.21 | 4.29E−06 | DCX | −2.11 | 2.73E−04 |
| SEMA3C | −2.14 | 4.49E−06 | EFNB2 | −2.24 | 2.35E−04 | CHRNA3 | −2.69 | 2.69E−06 |
| MEIS1 | −2.14 | 1.05E−04 | APOE | −2.41 | 8.27E−05 | GAP43 | −2.96 | 5.08E−06 |
| DLX5 | −2.22 | 2.04E−05 | RAX | −2.57 | 2.70E−05 | CTGF | −3.06 | 1.94E−05 |
| NR2F2 | −2.64 | 2.63E−06 | LAMB1 | −2.64 | 1.10E−05 | ANKRD1 | −3.60 | 1.35E−06 |
| EVI1 | −2.68 | 3.30E−06 | GAP43 | −2.76 | 2.45E−04 | POU3F1 | −3.70 | 3.79E−07 |
| PDGFC | −2.80 | 4.38E−06 | CTGF | −4.43 | 9.83E−07 | SYT4 | −4.35 | 4.97E−08 |
| DCT | −3.52 | 9.43E−11 | ANKRD1 | −4.46 | 1.28E−07 | GRP | −4.59 | 4.02E−08 |
| PAX6 | −4.64 | 2.32E−08 | HEY1 | −4.48 | 2.55E−04 | EMP1 | −4.68 | 5.10E−06 |
| GAS1 | −5.43 | 9.25E−08 | LEFTY2 | −4.67 | 2.27E−06 | NKX2-2 | −4.74 | 7.66E−09 |
| CCL2 | −5.85 | 7.78E−08 | EPCAM | −4.93 | 6.11E−05 | STMN2 | −5.50 | 2.16E−09 |
| EMX2 | −6.08 | 1.00E−10 | COL1A1 | −4.98 | 4.33E−08 | VGF | −5.86 | 1.97E−09 |
| ALDH1A1 | −8.99 | 9.36E−11 | EMP1 | −6.14 | 8.08E−06 | MMP7 | −6.62 | 4.37E−09 |

The importance of SHH dosage during in vitro ventral forebrain specification has been demonstrated by using intermediate SHH levels for directing hESC-derived neuroepithelial progenitors towards GSX2 positive, NKX2.1 negative progenitors, which can be induced to generate medium spiny striatal projection neurons. Ma et al., *Cell Stem Cell* 10:455-464 (2012). Cortical projection neuron markers include, without limitation, PAX6, TBR2, TBR1, SATB2, CTIP2, VGLUT1, FEZF2, SF6C, and Glutamate.

In addition to SHH-dose, timing of SHH treatment can also affect the efficiency of ventral cell fate specification as previously demonstrated for hESC-based floor plate induction. Fasano et al., *Cell Stem Cell* 6:336-347 (2010). Remarkably, the difference in timing of SHH activation alone is sufficient to trigger the generation of distinct ventral progenitors of divergent anterior-posterior identity. The derivation of hESC-derived progenitors expressing markers of the hypothalamic anlage has been reported following early activation of SHH signaling in the presence of FGF8. Kriks et al., *Nature* 480:547-551 (2011).

The presently disclosed day 2-18 protocol data extend these findings and suggest that the addition of FGF8 is not critical for directing hypothalamic progenitor fate. The predominant cholinergic neuron fate observed in NKX2.1::GFP+ progenitors that derived from the day 6-18 group can be employed for the modeling and treatment of disorders that are associated with the loss of cognitive function. For example, in Alzheimer's disease basal forebrain cholinergic neurons are amongst the neurons most vulnerable during early stages of the disease. Whitehouse et al., *Science* 215:1237-1239 (1982).

As disclosed herein, the use of the NKX2.1::GFP reporter hESC line (Goulburn et al., *Stem Cells* 29:462-473 (2011)) allowed optimization of protocols and efficient conversion of nearly all hESC progeny to a FOXG1+/NKX2.1+ ventral forebrain fate when SHH treatment was initiated at day 6 or later.

The data presented herein demonstrates the timing of SHH activation can be exploited to control the subtype of NKX2.1+ neural progenitor cell that are generated from neuronal cells. It has been suggested that NKX2.1 may be produced during early neural development in human FOXG1 positive telencephalons as well as in FOXG1 negative ventral diencephalon cells. See, e.g., FIG. 2A and Kerwin et al., *J Anat* 217:289-299 (2010) and Rakic and Zecevic, *Cereb Cortex* 13:1072-1083 (2003). During embryonic mouse development NKX2.1 expression in the telencephalon (FOXG 1+) is restricted to the 25 ventral (subcortical) domain. In contrast, in human fetal tissue, it has been reported that NKX2.1 expression is not be restricted to the ventral forebrain but, instead, extends into the dorsal forebrain and cortical anlage. Rakic and Zecevic, *Cereb Cortex* 13:1072-1083 (2003) and Yu and Zecevic, *J Neurosci* 31:2413-2420 (2011). These human studies were, however, largely based on the analysis of second trimester fetuses making it difficult to confirm whether NKX2.1+ cells were induced directly in the dorsal forebrain or migrated dorsally following induction in the ventral domain. Fertuzinhos et al., *Cereb Cortex* 19(9):2196-2207 (2009).

As disclosed herein, immunocytochemical analyses were performed in early stage human embryos (Carnegie Stage 15, ~38 days post conception) where restriction of NKX2.1 expression was observed to be limited to the ventral forebrain. See, e.g., FIGS. 2B-2E. The presently disclosed human data are, therefore, comparable to data derived from mouse studies. The present data further demonstrated that the NKX2.1 domain in the human embryonic ventral forebrain was further subdivided into an OLIG2+ ganglionic eminence and an OLIG2-negative pre-optic area anlage. See, e.g., FIGS. 2C and 2D.

The regional identity of hPSC-derived NKX2.1::GFP+ cells was evaluated by comparing differentiation day 2-18, differentiation day 6-18, and differentiation day 10-18 SHH treatment groups. FIG. 2F. These data confirm results derived from previous studies on floor plate induction by SMAD inhibitors. Fasano et al., Cell Stem Cell 6:336-347 (2010). Early SHH exposure (i.e., differentiation day 2-18 SHH treatment group) exhibited suppressed FOXG1 induction despite robust induction of NKX2.1::GFP. See, FIG. 2G, left panel, and FIG. 1H, respectively.

In contrast, both the differentiation day 6-18 and the differentiation day 10-18 SHH treatment groups exhibited expression of FOXG1, but differed in OLIG2 expression. See, FIG. 2G, middle and right panels. While not wishing to be bound by theory, it is believed that differential expression of FOXG1 and OLIG2 reflects the distinct NKX2.1+ precursor domains that are observed during early human development (FIGS. 2A-E) and mimic the Olig2+ domains during mouse forebrain development. Flames et al., J Neurosci 27:9682-9695 (2007). More than 90% of the NKX2.1:: GFP+ cells in the differentiation day 6-18 SHH treatment group and the differentiation day 10-18 SHH treatment group co-expressed FOXG1 and nearly 80% of the GFP+ cells in the differentiation day 10-18 SHH treatment group co-expressed OLIG2. See, FIG. 2H.

The impact of timing of SHH exposure on the derivation of specific ventral precursor populations was further examined by global transcriptome analyses. See, FIGS. 2I-2K and Table 1).

dorsal forebrain markers such as EMX2 and PAX6. See, FIG. 2I. No significant differences were observed in the expression of general anterior markers such as FOXG1 and OTX2. See, FIG. 2I. These data support the forebrain identity of both cell populations.

Comparison of the differentiation day 10-18 SHH treatment group to the differentiation day 2-18 SHH treatment group illustrated differences in the expression of anterior markers such as FOXG1 versus diencephalic markers such as RAX. FIG. 2J. In contrast, comparison of the differentiation day 10-18 SHH treatment group to the differentiation day 6-18 SHH treatment group revealed less pronounced differences in forebrain marker expression. See, FIG. 2K. These data demonstrate that the timing of SHH treatment significantly impacts the regional identity of hPSC-derived NKX2.1 precursors.

Gene expression data demonstrated that induction of FOXA2 in all SHH treated cultures, including the differentiation day 10-18 SHH treatment group. See, FIG. 2I. Expression of FOXA2, a floor plate marker within the developing CNS, was confirmed at day 18 of differentiation in NKX2.1::GFP+ cells from all of the three SHH treatment groups. See, FIGS. 3A and 3B.

Histological analyses in the developing mouse and human forebrain was performed in mouse embryos at embryonic day 11.5 to address whether FOXA2 expression may represent an in vitro artifact following strong extrinsic activation of SHH signaling or whether FOXA2 expression occurs in the telencephalon during in vivo development. The data presented herein demonstrated that FOXA2 expression within the mouse prosencephalon segregated from the

TABLE 1

Global Transcriptome Analysis of SHH Treatment Timing

| day 10-18 versus no SHH | | | day 10-18 versus day 2-18 | | | day 10-18 versus day 6-18 | | |
| --- | --- | --- | --- | --- | --- | --- | --- | --- |
| Probeset | F-Change | p-value | Probeset | F-Change | p-value | Probeset | F-Change | p-value |
| SIX6 | 7.87988 | 6.35E−09 | ZIC2 | 9.25125 | 1.56E−09 | SOX21 | 3.13594 | 3.37E−07 |
| NKX2-1 | 6.92226 | 3.40E−10 | FOXG1 | 6.69631 | 6.70E−05 | SP8 | 2.80875 | 1.40E−08 |
| LIPA | 6.46827 | 8.53E−09 | PCSK5 | 3.38548 | 3.35E−05 | PCDH19 | 2.65059 | 2.29E−06 |
| IFIT1 | 5.72857 | 521E−09 | ZIC3 | 3.18514 | 0.000225 | FOXG1 | 2.38942 | 6.69E−05 |
| SNORD3A | 5.3669 | 4.69E−07 | NDP | 3.12398 | 0.000276 | OTX2 | 2.38205 | 5.20E−08 |
| OLIG1 | 4.70296 | 2.51E−07 | WNT5B | 2.66089 | 0.00029 | C14ORF23 | 2.37433 | 5.84E−06 |
| NKX2-2 | 4.62431 | 8.69E−09 | PLCH1 | 2.56463 | 1.52E−05 | SHISA2 | 2.36185 | 6.38E−05 |
| PTCH1 | 3.96485 | 2.07E−06 | KCNK12 | 2.53973 | 0.000274 | PCSK5 | 2.19359 | 1.67E−05 |
| OLIG2 | 3.89558 | 1.15E−05 | CDH11 | 2.43608 | 4.13E−05 | MYCN | 2.19199 | 1.14E−05 |
| NKX6-2 | 3.74118 | 2.12E−07 | MYCN | 2.40706 | 2.18E−06 | FRZB | 2.11983 | 6.43E−05 |
| HES1 | 3.46284 | 2.42E−09 | REC8 | 2.07819 | 0.000104 | DOCK11 | 2.10759 | 0.000229 |
| ASCL1 | 2.99662 | 1.42E−06 | HCRT | 2.07746 | 0.00032 | FOXO1 | 2.08114 | 0.000174 |
| FOXA2 | 2.6262 | 6.86E−07 | LMO2 | 2.05958 | 2.05E−05 | ALCAM | 2.08046 | 0.000361 |
| SEMA3A | −2.0005 | 0.000475 | KLF6 | −2.21322 | 4.29E−06 | DCX | −2.11114 | 0.000273 |
| SEMA3C | −2.13947 | 4.49E−06 | EFNB2 | −2.23576 | 0.000235 | CHRNA3 | −2.69142 | 2.69E−06 |
| MEIS1 | −2.14363 | 0.000105 | APOE | −2.40952 | 8.27E−05 | GAP43 | −2.95957 | 5.08E−06 |
| DLX5 | −2.21799 | 2.04E−05 | RAX | −2.57197 | 2.70E−05 | CTGF | −3.05732 | 1.94E−05 |
| NR2F2 | −2.6352 | 2.63E−08 | LAMB1 | −2.64019 | 1.10E−05 | ANKRD1 | −3.6028 | 1.35E−06 |
| EVI1 | −2.67648 | 3.30E−06 | GAP43 | −2.76483 | 0.000245 | POU3F1 | −3.69694 | 3.79E−07 |
| PDGFC | −2.80264 | 4.38E−06 | CTGF | −4.4333 | 9.83E−07 | SYT4 | −4.3542 | 4.97E−08 |
| DCT | −3.51574 | 9.43E−11 | ANKRD1 | −4.45958 | 1.28E−07 | GRP | −4.5884 | 4.02E−08 |
| PAX6 | −4.63536 | 2.32E−08 | HEY1 | −4.47756 | 0.000255 | EMP1 | −4.68053 | 5.10E−06 |
| GAS1 | −5.42817 | 9.25E−08 | LEFTY2 | −4.66604 | 2.27E−06 | NKX2-2 | −4.73957 | 7.66E−09 |
| CCL2 | −5.84815 | 7.78E−08 | EPCAM | −4.93135 | 6.11E−05 | STMN2 | −5.50274 | 2.16E−09 |
| EMX2 | −6.08337 | 1.00E−10 | COL1A1 | −4.9844 | 4.33E−08 | VGF | −5.85728 | 1.97E−09 |
| ALDH1A1 | −8.98763 | 9.36E−11 | EMP1 | −6.14497 | 8.08E−06 | MMP7 | −6.61675 | 4.37E−09 |

A direct comparison of the differentiation day 10-18 SHH treatment group versus untreated cultures (e.g., no SHH treatment) confirmed the robust induction of ventral specification markers such as NKX2.1, NKX2.2, ASCL1, SIX6, OLIG2, and NKX6.2, which were induced at the expense of FOXG1 and NKX2.1 domains. See, FIG. 3C. Immunohistochemical analysis for FOXA2 in primary human forebrain tissue (CS15 embryo) confirmed expression in the anlage of the telencephalic NKX2.1+ ganglionic eminence. See, FIGS. 3D-3F. These data demonstrate that transient FOXA2 expression occurs during human ventral forebrain development, which data are consistent with in vitro hPSC differentiation data.

Example 3

Directed Differentiation of Forebrain Neural Progenitor Cells into Neuronal Cells and the Migratory Properties of Those Neuronal Cells This Example demonstrates the generation of neuronal cells by the directed differentiation of forebrain neural progenitor cells.

Cortical interneurons derived from the ganglionic eminence are particularly important in balancing excitation and inhibition within cortical circuitry. Moreover, cortical interneurons play key roles in controlling developmental plasticity and are dysfunctional in various pathological conditions including epilepsy, autism, and schizophrenia. Baraban et al., Proc Natl Acad Sci USA 106:15472-15477 (2009); Eagleson et al. Autism Res 4:68-83 (2011); Insel, Nature 468:187-193 (2010); Lewis et al., Nat Rev Neurosci 6:312-324 (2005); and Penagarikano et al., Cell 147:235-246 (2011).

Day 10-18 treated precursor cells express many of the transcription factors, including OLIG2, MASH1, and NKX6.2, which are markers of cortical interneuron progenitor domains during mouse development. While most NKX2.1::GFP cells at day 18 of differentiation exhibit progenitor cell properties, which is evidenced by Nestin and Ki67 expression.

As demonstrated herein, prolonged culture in the absence of extrinsic SHH activation led to a gradual decrease in cycling NKX2.1::GFP cells. FIGS. 4A-4C, upper panels. At day 18, cells from the three indicated protocols were subjected to FACS for NKX2.1::GFP production and were then replated and evaluated for co-labeling with cortical interneuron markers. FIGS. 4A-4C. All three protocols exhibited a reduction in progenitor marker production and an increase in the production of markers of neuronal differentiation (i.e., GABA, TUJ1, doublecortin (DCX), and calbindin).

Decreased Ki67 rates were paralleled by increases in the percentage of cells expressing the neuronal precursor markers DCX and TUJ1. FIGS. 4A-4C, lower panels. Moreover, many of the GFP+ cells in the 10-18 day and 2-18 day conditions expressed GABA and showed a time-dependent increase in the expression of calbindin, which is a marker of tangentially-migrating cortical interneuron precursors as well as other populations. FIGS. 4A-4C, lower panels; Anderson et al., Science 278:474-476 (1997).

Western blot analysis at day 32 of differentiation showed that the medial ganglionic eminence (MGE)-enriched LHX6 protein, a marker of post-mitotic, migratory cortical interneuron precursors in the mouse, was selectively enriched in the 10-18 day condition while the hypothalamic marker RAX was selectively enriched in the 2-18 day condition. FIG. 4D. Additional immunocytochemical data revealed expression of DLX2 and ASCL1 in most neuronal progeny derived from the day 10-18 NKX2.1::GFP+ progenitors. FIGS. 4E-4G. At day 32, many of the NKX2.1:: GFP+ cells from the 10 to 18 condition also expressed DLX2 and ASCL1 suggesting that following withdrawal of extrinsic SHH signaling activators, NKX2.1::GFP+ progenitors gave rise to region-specific postmitotic neurons, including the precursors of cortical interneurons. FIGS. 4E-4G.

Human ESC-derived putative cortical interneuron precursors (day 10-18 group) were assessed for the characteristic migratory potential observed for primary cortical interneurons in the mouse (Anderson et al., Science 278:474-476 (1997)) and human (Letinic et al., Nature 417:645-649 (2002)) brain.

Cells were lysed with Ripa Buffer (50 mM Tris-HCl pH 8.0, 120 mM NaCl, 5 mM EDTA, 0.5% NP-40, and a tablet of protease inhibitor). Protein concentration was measured by the Bradford Assay (Bio-Rad). For immunoblot, whole cell extract (4×106 cells per sample) were boiled for 5 minutes in Laemmli sample buffer before separation by electrophoresis on 4-12% Bis-Tris gel in MOPS SDS running buffer at 100V for 2 hours using a iBlot electroblotter (Invitrogen).

Protein was transferred to nitrocellulose membrane using the iBlot gel transfer device (Invitrogen). Non-specific protein binding was prevented by blocking the membrane with 3% BSA and PBS-T (0.1% Tween-20). Membrane was incubated at 4 degrees overnight in 3% BSA and PBS-T with primary antibodies (LHX6 (1:500; Abeam), RAX (1:250; Abnova), GAPDH (1:10,000; Thermo Scientific). After five washes with PBS-T (0.1% Tween-20), the blot was incubated with respective secondary antibodies (Rabbit (1:10, 000), Mouse (1:20,000) at room temperature. ECL kit, Western Lightning Plus-ECL, was used for detection according to manufacturer's instruction (PerkinElmer). Secondary antibodies were all purchased from Jackson Immunoresearch. ECL kit, Western Lightning Plus-ECL, was used for detection according to manufacturer's instruction (PerkinElmer).

Coronal telencephalic slices, 250 µm thick, were prepared and cultured as described (Anderson et al., Development 128:353-363 (2001)). Slices were maintained in Neurobasal/B27 with 5 ng/ml recombinant human FGF2 (Promega). Early stage (day 32-39 of differentiation) hESC-derived NKX2.1::GFP+ cells were isolated by FACS then carefully injected into periventricular region of the MGE using an oocyte microinjector (Nanoinject II; Drummond). Roughly 5000 cells were injected per slice hemisphere. Cultures were maintained for 2 or 6 days before fixing and processing for immunostaining. For cell counting, Zone 1 was defined as the region from the ventricular zone of the lateral ganglionic eminence extending to the pallial-subpallial border. Zone 2 was defined as the region from the lateral cortex through the neocortex to the cortical hem.

Transplantation targeting the somatosensory neocortex of neonatal pups of NOD-SCID IL2RG-/- mice was conducted as described previously. Wonders et al., Dev Biol 314:127-136 (2008). 50-80×10$^3$ cells were injected into the cortical plate at following coordinates from bregma (2.0 mm A, 2.5 mm L, 1.0 mm D), targeting cortical layers 3-6. Care of animals was in accordance with institutional guidelines at the WCMC and the National Institutes of Health.

In both mice and humans, major subclasses of cortical interneurons undergo tangential migration on their way from the ventral telencephalon into the cortex. Anderson et al., Science 278:474-476 (1997); Fertuzinhos et al., Cereb Cortex 19(9):2196-2207 (2009); and Letinic et al., Nature 417:645-649 (2002). NKX2.1::GFP+ cells at day 32 of differentiation were collected by FACS and injected into forebrain slices isolated from embryonic day 13.5 mouse embryos. Cell injection was carefully targeted to the medial ganglionic eminence under microscopic visual guidance.

FIG. 4H presents a schematic of coronal hemisection demonstrating the site of transplantation and the zones for quantification of migration. The migratory potential of NKX2.1::GFP+ cells and their ability to reach the cortex (see Zone 2 in FIG. 4H) was compared among the three treatment groups (2-18 day, 6-18 day, and 10-18 day of SHH treatment; FIGS. 4I-4L). In both the 2 to 18 and the 6 to 18 conditions, very few cells migrated into zone 1 and fewer into zone 2 (FIG. 4K). Only the 10 to 18 day condition demonstrated significant and robust migration into the cortical and striatal regions, with many GFP+ cells exhibiting bipolar morphologies consistent with a migratory cell (FIG. 4L).

At day 2 (FIG. 4M) and, more pronounced at day 6 (FIG. 4N) after injection, GFP+ cells were observed migrating from the injection site towards the cortex (zone 2) (* p<0.05; ** p<0.01 using ANOVA followed by Scheffe test). Remarkably, human cells from the 10-18 treatment, but not the two other treatment groups, showed a robust propensity for migration into the neocortical portions of the murine slice (FIG. 4I-4N). These data suggest that day 10-18 treated cells exhibit migratory properties previously described for primary mouse MGE-derived interneuron precursors. Lavdas et al., *J Neurosci* 19:7881-7888 (1999); Sussel et al., *Development* 126:3359-3370 (1999); and Wichterle et al., *Nat Neurosci* 2:461-466 (1999). To further probe the migratory capacity of the day 2-18 versus 10-18 treated cells, we transplanted FACS-isolated NKX2.1::GFP-1- cells into the neocortex of neonatal, genetically immuno-compromised mice. FIGS. 4O-4P show the transplantation of day 32 sorted NKX2.1::GFP+ cells (day 10 to 18 protocol) into the neocortex of neonatal mice followed by their evaluation in fixed sections at postnatal day 30. In marked contrast to the MGE-like cells from the SHH 10-18 protocol (FIG. 4P), neither the SHH 2-18 protocol (FIG. 4O) nor the SHH 6-18 protocol (not shown) resulted in extensive migration from the graft site. Four weeks after transplantation we observed extensive migration, in both the radial and tangential planes within the mouse cortex but only for the day 10-18 group (FIGS. 4O and 4P).

Similar results were obtained upon transplantation into the adult cortex (FIG. 5A-5D) though overall migration of NKX2.1::GFP+ cells by day 30 in vivo was less extensive compared to the neonatal grafts. FIG. 5A-5D shows the distribution of NKX2.1::GFP+ neuronal precursors within the adult mouse cortex. NKX2.1::GFP expressing cells were sorted at day 32 of differentiation and grafted into adult IL2RG immunocompromised mice. While the 2 to 18 (FIG. 5A) and the 6 to 18 (FIG. 5B) condition produced regions of GFP expression in the cortex after 30 days, the GFP cell bodies did not leave the graft core. Only in the 10 to 18 condition (FIG. 5C) did GFP expressing cells leave the graft core and distribute throughout the cortical parenchyma. In addition the GFP expressing cells from the 10 to 18 condition distribute throughout the cortical layers and display neuronal morphologies (FIG. 5D)

To determine the extent of interneuron precursor maturation in vivo, we assessed morphological appearance and the expression of interneuron-related markers in the grafted cells from the day 10-18 group FIG. 6A-6D2, which demonstrates the slow pace of differentiation by Nkx2.1-GFP+ cells following transplantation into neonatal mouse neocortex. Shown are examples of transplants of the Nkx2.1-GFP line, differentiated to day 32 with the "MGE-like protocol (SHH 10-18), then subjected to FACS for GFP, transplanted into the neonatal neocortex of genetically immunecompromised mice, and evaluated in fixed sections after 6 weeks (see methods). FIG. 6A shows low magnification view of GFP immunofluorescence labeling. Scale bar=100 μm. The boxed area shows three cells at higher magnification in panel (FIG. 6A1). Note that even after 6 weeks of differentiation in vivo most of these cells continue to have relatively undifferentiated appearance with bipolar or unipolar processes, often tipped by growth cones (arrow). Scale bar=20 μm. FIG. 6B shows immunofluorescence for the human specific cell marker SC121 (FIGS. 6B, 6B1, and 6B3) and GFP (FIGS. 6B, 6B1, and 6B2). All GFP+ cells express SC121, and most but not quite all SC121 cells at this age express GFP (arrows). As we see similarly low percentages of SC121+/GFP- cells two weeks after transplantation (not shown), it is not clear whether these cells represent downregulation of Nkx2.1 and GFP or represent GFP- cells that came through the FACS (FIG. 6B; Scale bar=35 μm, FIGS. 6B1-6B3 scale bar=40 μm). FIG. 6C shows the same view of a section with immunofluorescence for GABA and GFP. Two strongly co-labeled cells are indicated by the arrows. As GABA immunodetection penetrates poorly into sections, co-labeling was quantified by selectively counting only those GFP+ cells with cell bodies located within 5 microns of the cut edges of the section. By this approach, 46 of 51 cells (90.2%) from two 6-week transplants were strongly colabeled. Scale bar=40 μm. FIG. 6D shows immunofluorescence for GFP, Nkx2.1 and the marker of neuronal precursors DCX (blue; pseudocolored Cy5 signal). All the GFP+ cells have Nkx2.1-expressing nuclei (arrows), and also co-label for DCX. Scale bar=40 μm.

At both 1 and 2 months after transplantation (neonatal mouse cortex) most human cells exhibited an undifferentiated appearance with bipolar or unipolar morphologies and continued to express NKX2.1. Furthermore, essentially all grafted cells expressed the neuronal precursor marker DCX, including those with multipolar morphologies (FIG. 6A-6D2). As occurs in rodents, the large majority of human interneuron precursors expressed GABA (46/51 GFP+ cells located at the section surface; FIG. 6A-6D2). In contrast, co-labeling for parvalbumin (PV) or somatostatin (SST), two proteins detected in the major subclasses of Nkx2.1-lineage interneurons, was not present. This result indicates that even by six weeks post-transplant, the Nkx2.1-GFP+ cells had not yet differentiated into mature interneurons (FIG. 6A-6D2)

One explanation for the apparent lack of differentiation of the grafted GFP+ cells in the mouse host cortex could be that NKX2.1 is downregulated following maturation, as occurs in mouse cortical interneurons (Marin et al., *J Soc Neurosci* 20:6063-6076 (2000)), resulting in the loss of GFP expression by the more differentiated cells. To test this possibility sections were examined for expression of SC121, a human-specific pan-neuronal marker. Kelly et al., *Proc Natl Acad Sci USA* 101:11839-11844 (2004). As expected, all GFP+ cells also expressed SC121 (FIG. 6A-6D2). However, even at 6 weeks after transplantation, less than 10% of human cells expressed SC121 but not GFP (25 out of 372 GFP+ cells, counted from two 6 week transplants). In sum, perhaps due to the human interneuron precursor's tendency to follow a protracted pace of maturation in vivo, transplantation studies did not result in mature interneuron differentiation within the first two months of transplant.

The present disclosure points to several surprising differences in human versus mouse forebrain development. One difference was the human specific expression of FOXA2 in hESC derived ventral forebrain progenitors and in CS15 human forebrain tissue. We speculate that transient FOXA2 expression may be related to a prolonged requirement for SHH signaling during human development given the protracted forebrain development and obvious differences in brain size that may depend on the long-term proliferation of SHH dependent progenitors. To further address this hypothesis in the future, it will be important to establish a time course of FOXA2 expression during human ventral forebrain development and to determine whether FOXA2 can be linked to SHH expression as commonly observed in other FOXA2+ CNS domains such as the floor plate. Placzek and Briscoe, *Nat Rev Neurosci* 6:230-240 (2005). Past studies have reported species differences in cortical interneuron development, based in part on the presence of ASCL1+ cells within the second trimester human fetal cortex. Letinic et al., *Nature* 417:645-649 (2002). Those data led to the hypothesis that many, and perhaps most human cortical interneurons are born within the cortex itself. Letinic et al., *Nature* 417:645-649 (2002). In contrast, studies in the mouse have demonstrated a subcortical origin of most if not all cortical interneurons. Fogarty et al., *J Neurosci* 27:10935-10946 (2007); Miyoshi et al., *J Neurosci* 30:1582-1594 (2010); and Xu et al., *J Neurosci* 24:2612-2622 (2004). While our study was not specifically geared towards addressing this issue, we found restricted NKX2.1 expression within the ventral forebrain in CS15 human embryo and a complete lack of expression in the dorsal forebrain (see also Allen Brain Atlas, http://human.brain-map.org/). Furthermore, the ability of hESCderived cortical interneurons to migrate in our slice culture assay and the developing murine cortex in vivo suggests that human cortical interneuron precursors have a similar capacity for tangential migration as their mouse counterparts. Another interesting feature in hESC-derived cortical interneurons was the persistent expression of NKX2.1. In contrast, NKX2.1 is extinguished in mouse cortical interneuron precursors by the time they leave the MGE prior to entering the cortex. Marin et at, *J Soc Neurosci* 20:6063-6076 (2000). Our in vitro data are consistent with findings in the human neocortex in vivo showing the presence of postmitotic NKX2.1+ neurons. Fertuzinhos et al., *Cereb Cortex* 19(9):2196-2207 (2009). However, our data do not rule out the possibility that a subset of our human ESCderived cells correspond to striatal interneurons, as those share markers of cortical interneurons in the mouse while retaining NKX2.1 expression (Marin et al., 2000).

Current paradigms of modeling human psychiatric disease such as schizophrenia are featuring the use of patient-specific iFSC-derived neurons. Brennand et al., *Nature* 473:221-225 (2011); Cheung et al., *Hum Mol Genet* 20:2103-2115 (2011); Chiang et al., *Mol Psychiatry* 16:358-360 (2011); Marchetto et al., *Cell* 143:527-539 (2010); and Pasca et al., *Nat Med* 17:1657-1662 (2011). However, those published studies were performed in mixed neural cultures of unclear neuronal subtype identity and with limited characterization of subtype specific synaptic and functional properties. There is a convergence of post-mortem findings that attempt to link genetic defects to psychiatric disorders, such as the interneuron-associated Erbb4 receptor in schizophrenia. Fazzari et al., *Nature* 464:1376-1380 (2010). Therefore it will be essential to have access to purified populations of mature cortical interneurons for modeling human disease. Our results demonstrate that the highly efficient derivation of cortical interneurons is possible following timed exposure to developmental cues. We find that putative hESC-derived GABAergic interneurons receive synaptic inputs from both other human interneurons and from excitatory mouse projection neurons. In addition, cells with neurochemical properties of cortical interneurons adopt fairly mature physiological properties within 30 days of being plated on mouse cortex cultures.

Example 4

Phenotypic and Synaptic Maturation of Forebrain Neuronal Precursor Cells

This Example demonstrates the phenotypic and synaptic maturation of forebrain neuronal precursor cells.

Cortical interneuron development has been studied using a co-culture system in which mouse embryonic MGE-derived progenitors are plated over a "feeder culture" composed mainly of mouse cortical pyramidal neurons and glia. Xu et al., *J Neurosci* 24:2612-2622 (2004).

To determine whether aspects of human interneuron maturation would be accelerated in this system relative to the xenografts, NKX2.1::GFP+ cells were collected by FACS at day 32 and replated onto cultures of dissociated embryonic mouse cortex (FIG. 4A). This FIG. shows the preparation of cortical excitatory neuron cultures from embryonic day 13.5 (E13.5) mice, onto which human NKX2.1::GFP+ cells (after FACS at day 32) are plated.

Whole-cell voltage and current clamp recordings were performed as described previously (Ying et al., *Eur J Neurosci* 23:465-480 (2006); Ying and Goldstein, *J Neurophysiol* 93:1935-1948 (2005); and Ying et al., *J Neurosci* 27:8719-8732 (2007)), and the methods were slightly modified for this study. Briefly, neurons were visualized using a Nikon microscope (ECLIPSE FN1) equipped with a 4× objective and a 40× water immersion objective and GFP-positive neurons were identified using epifluorescence optics. Neurons were recorded at 23-24° C. Input resistance was measured from voltage response elicited by intracellular injection of a small current pulse (−2 or 5 pA, 500 ms). Electrical signals were obtained using a Multiclamp 700B amplifier connected to an interface using Clampex 10.2 software (Molecular Devices, Foster City. Calif.). Liquid junction potentials were calculated and corrected off-line. Ying and Goldstein, *J Neurophysiol* 93:1935-1948 (2005).

During recordings, neurons were continuously perfused with freshly prepared ACSF which contained (in mM): 126 NaCl, 26 NaHCO3, 3.6 KCl, 1.2 NaH2PO4, 1.2 MgCl2, 2 CaCl2, and 17 glucose, and the solution was saturated with 95% O2-5% CO2. Pipette solution for all current clamp recordings as well as voltage clamp recordings of EPSCs contained (in mM): 135 K-gluconate, 5 NaCl, 10 HEPES, 0.5 EGTA, 3 K2-ATP, 0.2 Na-GTP, and 10 Na2-phosphocreatine, pH adjusted to 7.3 with KOH. For voltage-clamp recordings of IPSCs, the pipette solution contained (in mM): 130 CH3SO3Cs, 8.3 CH3SO3Na, 1.7 NaCl, 1 CaCl2, 10 EGTA, 2 Mg2-ATP, 0.3 Na-GTP, 10 HEPES; pH was adjusted to 7.2 with CsOH. Ying and Goldstein, *J Neurophysiol* 93:1935-1948 (2005). The bath solution for voltage clamp experiments was the same as that for current clamp recordings. A brief current pulse was applied to test firing properties at intensities from threshold (1×) to suprathreshold (4× or 5×). Drugs were applied by superfusion for at least 2 min. (−)-Bicuculline methochloride was from Tocris, and tetrodotoxin (TTX) was from Alomone Labs (Jerusalem, Israel); All other compounds were obtained from Sigma (St. Louis, Mo.). Data processing and analysis were performed using MiniAnalysis (Synaptosoft, Decatur, Ga.) and Clampfit 10 (Molecular Devices) as previously described. Ying et al., *Eur J Neurosci* 23:465-480 (2006) and Ying et al., 2007).

Cortical cells were isolated from E13.5 mouse embryos, a stage prior to the immigration into dorsal neocortex of the ventrally-derived interneurons (Anderson et al., *Science* 278:474-476 (1997)). Thus, this co-culture system mimics aspects of normal development with human NKX2.1+ cells developing in the presence of the glutamatergic cortical pyramidal neurons. Studies were performed in parallel using GFP+ cells derived from each of the three SHH treatment regimens (FIG. 7A-7K).

FIGS. 7B-7E show that after 30 days in vitro (DIV), cultures from the SHH 10-18 conditions are enriched for NKX2.1::GFP+ cells that co-express GABA (FIG. 7B, quantified in FIG. 7C; * p<0.05; ** p<0.01 using ANOVA followed by Scheffe test). In contrast only the SHH 6-18 condition was enriched for NKX2.1::GFP co-labeling with choline acetyl transferase (ChAT) (FIG. 7D, quantified in FIG. 7E; * p<0.05 using ANOVA followed by Scheffe test). FIGS. 7F and 7G show the spiking patterns of SHH day 10-18 (FIG. 7F) and SHH day 6-18 (FIG. 7G) neurons recorded at 28 DIV. Action potentials were initiated by protocols shown at bottom. FIGS. 7H-7K show that spontaneous spiking was recorded from cultures enriched for GABAergic (SHH day 10 to 18) and cholinergic (6 to 18) neurons in the absence (FIGS. 7H and 7I) and the presence (FIGS. 7J and 7K) of the GABAA receptor antagonist bicuculline. Bicuculline had little effect on the spontaneous firing activity in the 6 to 18 condition, consistent with the lack of GABAergic cells from either the mouse feeder or the human NKX2.1::GFP+ cells generated by this protocol.

Remarkably, in contrast to the in vivo studies, roughly 80% of the GFP+ cells from the 10-18 treated "MGE-like" cultures, versus 40% from the 2-18 "hypothalamic-like" and 15% from the 6-18 culture, expressed GABA. Likewise, the 6-18 culture that is enriched for telencephalic (FOXG1+) cells but not for those that express the interneuron precursor LHX6 (see FIG. 3D), was significantly enriched for cells that express the other major neurotransmitter-defined subclass of NKX2.1-lineage neurons, choline acetyltransferase (ChAT). We next determined whether GFP+ cells from day 10-18 treated cultures (enriched for GABA neurons, relative to the GABA-poor 6-18 cultures), give rise to neurons that undergo GABAergic synaptic transmission. Whole-cell patch-clamp electrophysiological studies (FIGS. 7F-7K) of identified GFP+ cells showed spontaneous firing in both day 10-18 and day 6-18 treated cultures (FIGS. 7H and 7I). However, only the day 10-18 group showed modulation of the firing rate of NKX2.1::GFP+ cells in response to the GABA-A receptor antagonist bicuculline (FIG. 7J). Since the cortical feeders contained only very few murine interneurons (in both day 10-18 and day 6-18 co-culture conditions), these results indicate that hPSC-derived GABAergic neurons mediate the inhibitory synaptic output (see also FIG. 8). Accordingly, in the day 6-18 cultures in which GABAergic neurons are more rare (FIG. 7C), the firing rates following bicuculline exposure remained unchanged (FIG. 7K).

To further analyze synaptic inputs onto the NKX2.1::GFP+ cells generated using the day 10-18 protocol, we examined spontaneous postsynaptic currents and localization of inhibitory or excitatory synaptic markers. GFP+ cells cultured on the mouse cortical feeder for 30 days expressed high levels of vesicular GABA transporter (VGAT), present within the presynaptic terminal of GABAergic synapses.

FIG. 8A-8L shows that NKX2.1::GFP+ GABAergic interneurons receive both excitatory and inhibitory synaptic inputs. FIGS. 8A-8E show collapsed z-stack confocal image showing NKX2.1::GFP+, vesicular GABA transporter (VGAT), and the post-synaptic GABAergic marker gephyrin. FIG. 8A. The dendrites of this GFP+ cell that co-label with gephyrin are receiving VGATexpressing pre-synaptic terminals (arrows). In addition, a GFP+ axonal process formed a VGAT+ pre-synaptic terminal adjacent to a GFP negative, gephyrin-expressing post-synaptic process (asterisk).

FIG. 8F shows that whole-cell patch clamp reveals spontaneous inhibitory postsynaptic currents (sIPSCs) recorded from an NKX2.1::GFP+ neuron (SHH 10 to 18 protocol), which are reversibly blocked by the addition of the GABA-A receptor antagonist bicuculline. FIGS. 8G-8K are collapsed z-stack confocal images showing NKX2.1::GFP, vesicular glutamate transporter 1 (VGLUT1; in FIG. 8G), and the post-synaptic marker PSD-95 (FIG. 8C). This GFP+ cell has dendrites that co-label with PSD-95 that are adjacent to VGLUT1-expressing pre-synaptic terminals. Note the presence of a GFP negative cell expressing VGLUT1 (FIG. 8G arrowheads), confirming the presence of excitatory glutamatergic neurons in the culture. FIG. 8L shows that consistent with the apparent presence of glutamatergic synaptic inputs, spontaneous excitatory postsynaptic currents (sEPSCs) were detected in the NKX2.1::GFP+ neurons (10 to 18).

All cells were plated on mouse cortical feeder following FACS for NKX2.1::GFP at day 32. The subcellular localization of VGAT within GFP+ cells closely matched expression of the GABAergic postsynaptic marker gephyrin (FIGS. 8A-8E). Whole-cell patch clamp analyses demonstrated that NKX2.1::GFP+ cells receive spontaneous inhibitory postsynaptic currents (sIPSCs; FIG. SF) which are reversibly blocked by the addition of the GABA-A receptor antagonist bicuculline. In addition to inhibitory inputs NKX2.1::GFP+ cells also receive excitatory inputs, as demonstrated by the presence of vesicular glutamate transporter 1 (VGLUT1) expression adjacent to GFP+ putative dendrites, and colabeling with the post-synaptic excitatory synapse marker PSD-95 (FIGS. 8G-8K). Consistent with the presence of glutamatergic synaptic inputs, spontaneous excitatory postsynaptic currents (sEPSCs; FIG. 8L) were also readily detected in the NKX2.1::GFP+ neurons. More detailed analyses on the spontaneous synaptic activities in NKX2.1::GFP+ cells are provided in FIG. 9A-9D and Table 2B.

Figures 9A, 9B, 9C, 9D:
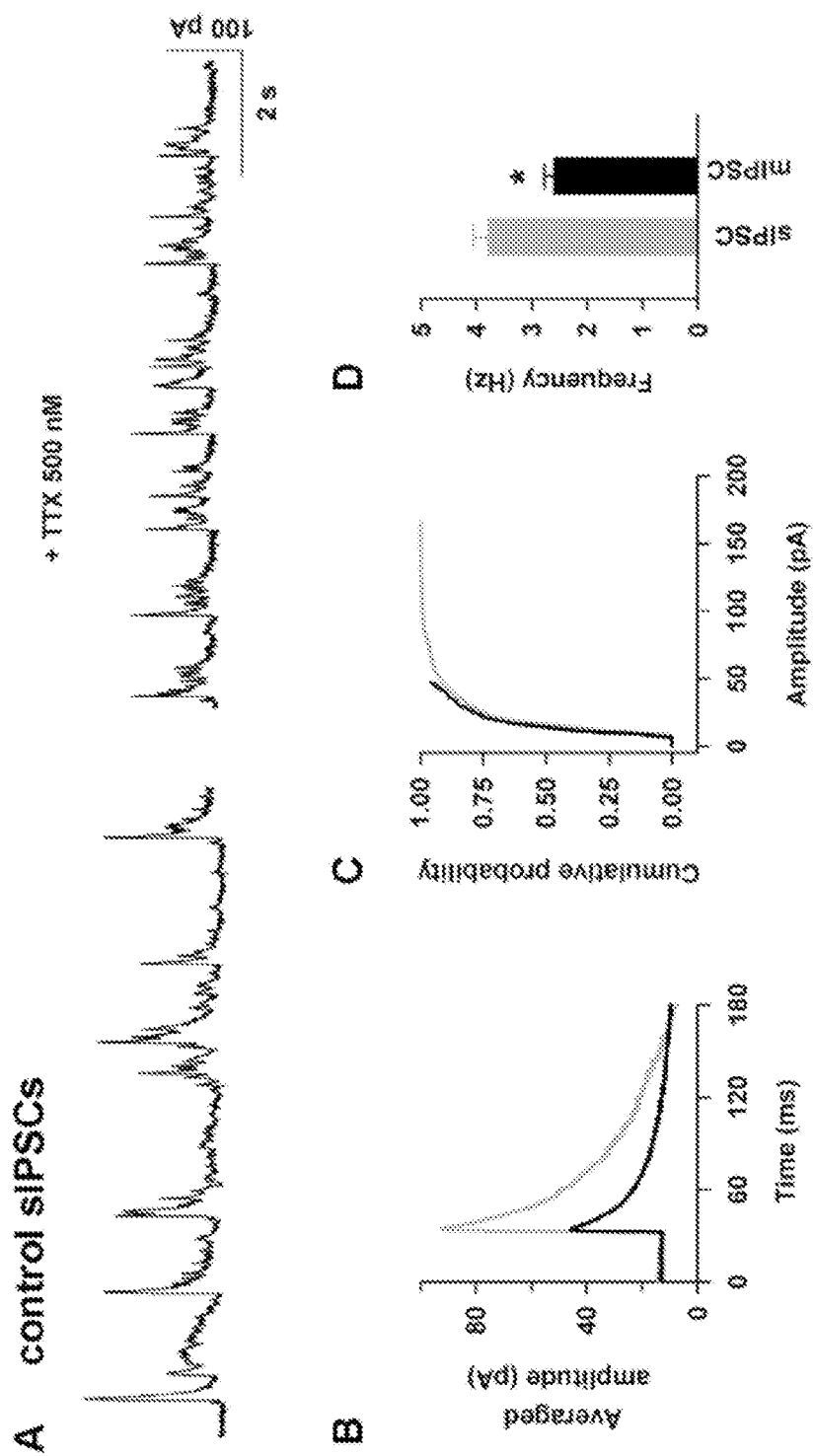
FIG. 9A-9D presents examples of spontaneous and miniature IPSCs recorded from a differentiation day 10-18 SHH treated group neuron.

FIG. 9A shows examples of spontaneous and miniature IPSCs recorded from a day 10-18 group neuron. FIG. 9B shows the overlay of the averaged sIPSCs (gray; n=150) and mIPSCs (black; n=56). Neurons were recorded on day 26-30 on mouse cortical feeders. FIG. 9C show cumulative probability histogram of IPSCs (gray) and mIPSCs (black). FIG. 9D shows grouped data comparing the frequency of sIPSPs (gray; n=\ markers (MAP2), astrocytic markers (GFAP), GABA, and cortical markers (SATB2, TBR1) in human ESC derived cortical precursors at day 30 of differentiation. All cells were plated on mouse or human ESC-derived cortical feeder following FACS for NKX2.1::GFP at day 32.

TABLE 2A

Electrophysiological properties of hESC-derived NKX2.1::GFP + neurons (day 10-18 and day 6-18 group) on mouse versus human cortical feeders

| | 10 to 18 on mouse feeder | | 6 to 18 on mouse feeder | | 10 to 18 on human feeder |
| --- | --- | --- | --- | --- | --- |
| DIV | 14-16 | 20-30 | 14-16 | 20-30 | 20-30 |
| RMP (mV) | −38.6 ± 2.4 | −65.6 ± 1.6** | −36.1 ± 2.4 | −62.6 ± 3.6** | −44.8 ± 6.6† |
| AP Amp (mV) | 57.4 ± 8.3 | 66.2 ± 4.1 | 56.2 ± 7.3 | 64.2 ± 5.1 | 62.5 ± 5.1 |
| AP Rise time (ms) | 1.472 ± 0.07 | 1.08 ± 0.03** | 1.52 ± 0.08 | 1.11 ± 0.09* | 1.9 ± 0.38† |

TABLE 2A-continued

Electrophysiological properties of hESC-derived NKX2.1::GFP + neurons
(day 10-18 and day 6-18 group) on mouse versus human cortical feeders

|  | 10 to 18 on mouse feeder | | 6 to 18 on mouse feeder | | 10 to 18 on human feeder |
|---|---|---|---|---|---|
| DIV | 14-16 | 20-30 | 14-16 | 20-30 | 20-30 |
| AP ½ Width (ms) | 3.05 ± 0.06 | 2.42 ± 0.12* | 3.02 ± 0.05 | 2.5 ± 0.11* | 4.8 ± 0.32†† |
| AHP peak (mV) | 10.1 ± 3.5 | 15.6 ± 2.4 | 11.2 ± 3.5 | 16.3 ± 2.6 | 8.8 ± 3.72 |
| $R_I$ (GΩ) | 1.5 ± 0.1 | 0.72 ± 0.05** | 0.94 ± 0.05 | 0.68 ± 0.12 | 1.66 ± 0.2†† |
| No. of cells | 8 | 15 | 8 | 12 | 5 |

DIV: days in vitro; $R_I$: Input resistance; AP: action potential; AHP: after-hyperpolarization.
*$P < 0.01$, unpaired t-test, compared to corresponding 14-16 DIV group
**$P < 0.001$, unpaired t-test, compared to corresponding 14-16 DIV group
†$P < 0.001$, unpaired t-test, compared to 10 to 18 mouse (20-30 DIV)
††$P < 0.0001$, unpaired t-test, compared to 10 to 18 mouse (20-30 DIV)
Action potential properties were measured at threshold as elicited by current injection

TABLE 2B

Averaged properties of GABAergic synoptic currents
in GFP-positive GABAergic interneurons

|  | sIPSC | mIPSC |
|---|---|---|
| Amplitude (pA) | 62.6 ± 5.2 | 35.1 ± 2.3* |
| Rise time (ms) | 2.4 ± 0.3 | 2.3 ± 0.4 |
| Decay time (ms) | 66.2 ± 5.4 | 51.2 ± 3.6* |
| ½ width (ms) | 54.5 ± 5.3 | 41.3 ± 3.2* |
| No. of cells | 8 | 4 |

Recordings were made at 26-30 DIV.
*$P < 0.05$, unpaired t-test

Cortical interneurons include a diverse set of neuron types with distinct roles in cortical development and function. Batista-Brito et al., *Curr Top Dev Biol* 87:81-118 (2009). The relatively rapid pace of maturation in our mouse cortical feeder system allowed us to assess co-expression of other more mature interneuron markers and to define neurotransmitter phenotypes beyond GABA and ChAT in NKX2.1::GFP+ cells.

FIG. 6 shows the neurochemical profiling of NKX2.1::GFP+ cells grown on mouse cortical feeders for 30 DIV. Cells were labeled by immunofluorescence for the markers indicated, and results quantified in graphs (A-E; * $p<0.05$,  $p<0.01$, * $p<0.001$ using ANOVA followed by Scheffe test: (*) $p<0.05$ when compared directly to 6-18 group. p-value did not reach significance in standard Scheffe test: p=0.08). Panels (FIG. 6F-6J) show representative images of cellular labeling. In the SHH 2 to 18 condition, most of the cells co-labeled with tyrosine hydroxylase (TH; FIG. 6A, 6F) and nNOS (FIG. 6B, 6G). In the 10 to 18 condition, many of the GFP+ cells colabeled with calbindin (Calb; FIG. 6C, 6H), somatostatin (SST; FIG. 6D, 6I), and parvalbumin (FIG. 6E, 6J) each of which is present in subpopulations of mature cortical interneurons in humans. All cells were plated on mouse cortical feeder following FACS for NKX2.1::GFP at day 32.

In the day 2-18 group a large percentage of GFP+ cells were observed that expressed TH (FIG. 6A), which is consistent with the dopaminergic nature of many NKX2.1-lineage hypothalamic neurons. Yee et al. *J Comp Neurol* 517:37-50 (2009). Immunohistochemistry for nNOS and calbindin showed high percentages of nNOS cells in GFP+ cells from the day 2-18 group while high percentages of calbindin+ neurons were present in the day 10-18 group (FIG. 6B, 6C).

Expression of other markers that are characteristic of differentiated cortical interneurons were also observed, including SST and PV (FIGS. 6D, 6E) in the day 10-18 group. Representative images for each subgroup marker, co-expressed together with NKX2.1::GFP, are presented in FIG. 6F-6J. No VIP expressing or calretinin expressing neurons were observed in suggesting the absence of cells exhibiting features of the caudal ganglionic eminence during mouse development. Xu et al., *J Neurosci* 24:2612-2622 (2004).

The derivation of NKX2.1+/PV+ was particularly remarkable given the late developmental expression of this marker in cortical interneurons in vivo. Zecevic et al., *Dev Neurobiol* 71:18-33 (2011). Only a subset of the cells counted as GFP+/PV+ by the automated image analyses (Operetta high content scanner) showed high levels of PV expression and exhibited interneuron-like morphologies (about 5% of total GFP+ cells (FIG. 6J)).

These results emphasize the need for further optimization in the derivation of selective cortical interneuron subtypes. The fact that PV+ hPSC-derived neurons were generated, however, suggests that the co-culture strategy using embryonic mouse cortical neurons represents a valuable platform to facilitate expression of subtype-specific neurochemical markers in hPSC-derived interneurons.

Given the protracted maturation of Nkx2.1-GFP+, putative interneuron precursors in vivo, we were surprised to obtain morphological, marker-based and physiological evidence of interneuron-like differentiation in the co-culture system. To determine whether the same GFP+ cells grown on cultures enriched for human cortical projection neurons would also show accelerated maturation, we performed studies where FACS-purified NKX2.1::GFP+ cells were co-cultured in parallel either on mouse versus human cortical neurons. FIG. 10 shows phenotypic characterization of human ESC-derived versus primary mouse cortical feeder cells. FIGS. 10A-10D show FACS-mediated isolation of cortical neuron precursors based on expression of CD24 and lack of expression of CD44 and CXCR4 (CD184). FIGS. 10E-10L show immunocytochemical analysis for expression of neuronal markers (MAP2), astrocytic markers (GFAP), GABA, and cortical markers (SATB2, TBR1) in hESC-derived cortical precursors at day 30 of differentiation. FIGS. 10M-10T show immunocytochemical analysis for expression of neuronal markers (MAP2), astrocytic markers (GFAP), GABA, and cortical markers (SATB2, TBR1) in mouse E13.5 cortical cultures. Overall, we observed comparable marker expression between primary mouse and hPSC derived cortical feeders.

The human cortical feeders were obtained upon differentiation of hESCs (modified XLSB conditions, see methods) followed by FACS for CD44−/CD184+/CD24+ neurons (Yuan et al., *PLoS One* 6:7540 (2011)) (FIGS. 10A-10D). The cortical identity of the hESC-derived neurons was confirmed by the expression of VGLUT1, MAP2, CTIP2, and SATB2, with only very few GFAP+ or Nestin+ cells present (FIGS. 10E and 10T). Interestingly, we observed a consistent difference in electrophysiological maturation of NKX2.1+ cells plated on mouse versus human cortical feeders as shown in Table 2A.

Recordings were obtained at either 14-16 DIV or 20-30 DIV for the mouse feeder condition, and 20-30 DIV for the human cortical feeder condition. Analysis of the basic electrophysiological properties of both the 10 to 18 and 6 to 18 groups plated on mouse feeders showed more mature characteristics at later time-points of differentiation. There was significant hyperpolarization of the resting membrane potential (RMP) with time, as well as a decrease in the input resistance (Ri). In addition, the action potentials became faster and narrower as evidenced by the decrease in the rise time and half width. In contrast, GFP+ neurons from the day 10-18 condition that were recorded 20-30 days after plating on the human feeder layer retained relatively immature characteristics, comparable to the measurements seen in the younger 14-16 DIV neurons plated onto a mouse feeder layer. The RMP, action potential rise time, action potential half width, and input resistance were significantly different in the cortical feeder condition when compared to the 10-18 neurons on mouse feeders recorded at the same DIV range. Sample traces depicting qualitative firing properties under the various conditions are shown in FIG. 11A-11C, which presents representative current clamp recordings from NKX2.1+ cortical interneurons. FIGS. 11A-11C show representative tracings from GFP-positive neurons from the day 10-18 treated group recorded on mouse feeders (FIGS. 11A and 11B) or human ES-derived neurons enriched for putative cerebral cortical projection neurons (FIG. 11C). Depolarized voltage responses were initiated using protocols shown below each set of traces. The holding potential was −60 mV for all recordings. All cells were plated on mouse or human ESC-derived cortical feeder following FACS for NKX2.1::GFP at day 32.

The present disclosure demonstrates that the proposed culture system can yield synaptically active cortical interneurons in vitro, a key prerequisite for modeling cortical interneuron pathologies in psychiatric disorders such as schizophrenia or autism. The generation of hESC-derived PV expressing neurons and the presence of relatively rapid spiking, non-accommodating neurons in these cultures is of particular interest given the implications of PV interneuron dysfunction in schizophrenia. Beasley and Reynolds *Schizophr Res* 24:349-355 (1997) and Woo et al., *Am J Psychiatry* 154:1013-1015 (1997). Fast-spiking PV+ cortical interneurons are observed late during primate prenatal development and continue their maturation into early adulthood. Anderson et al., *Neuroscience* 67:7-22 (1995) and Insel, *Nature* 468:187-193 (2010). Given the important role of PV+ neurons under various pathological conditions our data suggest that disease modeling of such states may be feasible using our differentiation strategies. Another key for the future will be the development of protocols that allow the enriched generation of specific cortical interneuron subgroups such as somatostatin+ versus PV+ cells. Our previous results in MGE progenitors indicate that this decision may be yet again under control of SHH signaling, with higher levels promoting somatostatin+ and lower levels promoting PV+ neurons. Xu et al., *Neuron* 65:328-340 (2010). Finally, future studies will be required to address the full in vivo potential of human in vitro derived cortical interneurons for applications in regenerative medicine. The present disclosure illustrates the remarkable migratory potential of the hESC-derived cortical interneurons upon transplantation into the neonatal mouse cortex. Transplantation studies into several adult CNS models of disease will be of particular interest given the potential use of cortical interneuron grafts in modulating pathological seizure activity (Baraban et al., *Proc Natl Acad Sci USA* 106:15472-15477 (2009)), treating aspects of Parkinson's disease (Martinez-Cerdeno et al., *Cell Stem Cell* 6:238-250 (2010)) and inducing learning and plasticity within the postnatal brain. Southwell et al., *Science* 327:1145-1148 (2010). One specific challenge for such transplantation studies is the protracted maturation of grafted hPSC-derived cortical interneuron precursors in vivo. Preliminary longer-term transplantation studies into the adult mouse cortex confirm their continued slow maturation rate with NKX2.1+ putative interneuron precursors retaining immature growth cones and showing limited integration at 3 months post grafting (data not shown). Those data are in contrast to our in vitro co-culture work where rapid functional integration and phenotypic maturation was readily achieved. In sum, this study provides a framework for the generation of distinct ventral prosencephalic neuron types that can be used to study various aspects of development and serves as a powerful in vitro platform to study dysfunction of specific neuron types implicated in a myriad of neuropsychiatric diseases.

Taken together, the present disclosure suggests that the pace of functional maturation is influenced by the local environment. Clearly, the mechanisms of the more rapid maturation rates in the presence of mouse versus human feeder cells remains to be determined. While it is possible that species-specific maturation rates of the cortical neurons triggers the timing of cortical interneuron maturation (e.g. by regulating activity), it is possible that there are simply more astrocytes in mouse versus human feeders that promote maturation. Johnson et al., *J Neurosci* 27:3069-3077 (2007). Future studies should include co-culture with primary cortical neurons of human embryonic origin to further corroborate our findings. Independent of mechanism, our data demonstrate that the mouse co-culture conditions allow for efficient maturation of hESC-derived cortical interneurons suitable for performing functional in vitro studies.

Example 5

Prophetic

Method for Screening Drugs Using In Vitro Differentiated Cortical Interneurons

This Example demonstrates that

Cell-based drug screening for neurodegenerative and neuropsychiatric diseases has been limited by the paucity of primary neurons and the difficulty of replacing neurons with cell lines. Most neurons are postmiotic and thus difficult to be produced in a quantity that suits HTS. However, human stem cells, such as ESC and iPSC, can be differentiated into neurons, as the present disclosure demonstrates and thus make drug screening using neurons more accessible.

iPSC can be obtained, for example, from human fibroblasts by methodology that is disclosed herein and as otherwise known in the art. Differentiation protocols yielding a variety of somatic cells are known, including cardiomyocytes (See, e.g., Van Oorschot A A et al., Panminerva Med. 2010 June; 52(2):97-110), hepatocytes (See, e.g., Alaimo G. et al., *J Cell Physiol.* 2013 June; 228(6):1249-54), kidney cells (See, e.g., De Chiara L. et al., *J Am Soc Nephrol.* 2014 February; 25(2):316-28), pancreatic beta cells (See, e.g., Roche E. et al., J Stem Cells. 2012; 7(4): 211-28), white blood cells (See, e.g., de Pooter R F et al., Methods Mol Biol. 2007; 380:73-81).

In addition, the present disclosure demonstrate that using a combination of SMAD/Wnt inhibition and SHH activation, stem cells can be differentiated into cortical interneurons, hypothalamic neurons and pre-optic cholinergic neurons. These neurons can be purified and used for screening candidate drugs, using known screening methods, such as high throughput screening.

Once cells are ready for screening, they can be plated to test various plating densities and cell culture vessels. For example, these cells can be plated on 6-well, 24-well, 96-well, 384-well plates or any other platforms that facilitate drug screening. Times for initiation and duration of trophic factor withdrawal will also be optimized once a suitable HTS format is selected.

Drug screens based on stem-cell derived somatic cells, including neurons, have been described. See, e.g., Yang et al., *Cell Stem Cell* 12:713-726 (2013). Briefly, small molecule survival screen was carried out using motor neurons (MNs) from both wild-type and mutant SOD1 mouse embryonic stem cells to search for drugs against amyotrophic lateral sclerosis (ALS). Mouse ESCs were differentiated into MNs and plated in 96-well or 384-well plates. Additionally, human MNs were derived from human ESCs and iPSCs after 30 days of differentiation, were also used. For the small molecule screen, freshly dissociated cells were plated at a density of 8,000 GFP+ cells (384-well plate) or 30,000 GFP+ cells (96-well plate) per well. Four days later, trophic factors were removed, and individual compounds were added to the wells. For the primary screen each compound was tested at three concentrations (0.1 mM, 1 mM, and 10 mM) in duplicate. After an additional 72 hr (day 7), cells were fixed and stained, and the number of MNs surviving was analyzed by counting the remaining GFP+ cells in the whole well. Survival is measured as fold increase compared to cultures maintained without trophic factors. Using this method, Yang and colleagues discovered that the compound kenpaullone had an impressive ability to prolong the healthy survival of MNs.

By combining the in vitro differentiation methods described in the present disclosure and an HTS platform, drug screening can be performed on cortical interneurons, hypothalamic neurons and pre-optic cholinergic neurons that play prominent roles in neurodegenerative and neuropsychiatric diseases. For example, human cortical interneurons can be produced according to the present disclosure, and these cells can be tested in a drug screen can be plated to test various plating densities and cell culture vessels. For example, cells can be plated on 6-well, 24-well, 96-well, 384-well plates or any other platforms that facilitate the drug screening. Times for initiation and duration of trophic factor withdrawal will also be optimized once a suitable HTS format is selected.

Molecules for use in a drug screen can come from a variety of sources, including small molecule compound libraries that can be designed in-house or obtained commercially. In the case of cortical interneurons, known drug molecules for neurodegenerative diseases, such as Alzheimer's disease, Parkinson's disease, which include biological and small molecules, can be tested. Such molecules can be screened at different concentrations, in combination with different cell densities, to optimize drug screen efficacy. For example, Yang et al. screened a collected of approximately 5000 small molecules to search for an ALS drug. For the primary screen, each compound was tested at three concentrations (0.1 mM, 1 mM, and 10 mM) in duplicate. After an additional 72 hr (day 7), MN cells were fixed, stained and accessed for survival. Yang et al., Id.

The phenotypic changes of the cortical interneurons after exposure to candidate compounds (whether small molecules or biologics) can be selected according to the disease intended to be treated as well as according to the intended effects of these compounds/molecules on these cells. These phenotypic changes include, but not limited to, cell survival, morphological changes of the cells, secretion of certain factors by the cells, expression of certain cell surface molecules, interaction of cells with other cells and/or with a solid support, changes in optical, electrical, and chemical properties of the cell, fluorescence signals of the cell (e.g., when the cells are transfected with a fluorescent protein, such as GFP-progerin, etc.) and attenuation or elimination of disease markers, among others. One application of the methods described by the present disclosure is to screen for drugs that can prolong the healthy survival of neuronal cells that are key to neurodegenerative diseases such as Parkinson's and Alzheimer's diseases. Thus, a drug screen can be designed to select compounds that will promote survival of cortical interneurons. In the case of PD, cortical interneurons derived from ESC or iPSC can be cultured, plated and exposed to compounds and their survival rate accessed. Furthermore, additional markers can be utilized as a basis for the drug screen in addition to cell survival. For example, known cell surface or intracellular markers of cortical interneurons can be used as criteria for drug screens. Compounds that can slow, halt or reverse the expression of one or more these functional markers could be candidates for drugs that may help treat these neurodegenerative diseases.

Hits can be defined as compounds/molecules that will effectively reverse one or more cortical interneurons-related marker signatures described above. For example, if cell survival is used and an endpoint, molecules can be selected that substantially increase the number of surviving cells (e.g., cortical interneurons) while preserving cell-appropriate morphological characteristics.

Candidate compounds that are selected from a primary screen can, optionally, be retested and subjected to additional testing including, but not limited to, dose-response and toxicity assays. Lead compounds can be selected and can be structurally modified to improve desired characteristics and/or to reduce side effects. Other improvements to the lead compounds can include increased absorption, longer half-life, higher affinity to cells, and enhancement of local and/or systemic delivery. Lead compounds and modified variants thereof can be further studied in preclinical studies including in suitable cell culture and animal model systems and, those exhibiting favorable therapeutic and toxicity profiles can be subjected to further in vivo testing in human clinical trials.

TABLE 3

List of primary antibodies, their sources and concentrations used in the current study

| Antibody | Species | Dilution | Source | Cat. No. |
|---|---|---|---|---|
| ASCL1 | Mouse | 1/250 | BD Pharmingen | 556604 |
| Calbindin | Rabbit | 1/3000 | Swant | CB38a |
| Calretinin | Mouse | 1/2000 | Swant | 6B3 |
| ChAT | Goat | 1/100 | Millipore | AB144P |
| DLX2 | Rabbit | 1/200 | gift from J. Rubenstein | n/a |
| Doublecortin | Goat | 1/100 | SCBT | sc-8067 |
| FOXA2 | Goat | 1/200 | SCBT | sc-6554 |
| FOXG1 | Rabbit | 1/500 | Neuracell | NC-FAB |
| FOXG1 | Rabbit | 1/1000 | gift from Eseng Lai | n/a |
| GABA | Rabbit | 1/4000 | Sigma Aldrich | A2052 |
| GAPDH | Rabbit | 1/10000 | Thermo Scientific | PA1-16780 |
| Gephyrin | Mouse | 1/2000 | Synaptic Systems | 147011 |
| GFAP | Goat | 1/300 | SCBT | sc-6170 |
| GFP | Chicken | 1/1000 | Abcam | ab13970 |
| KI67 | Rabbit | 1/1000 | Thermo Scientific | RM-9106 |
| KI67 | Mouse | 1/200 | DAKO | MIB-1 |
| LHX6 | rabbit | 1/500 | Abcam | ab22885 |
| MAP2 | Chicken | 1/10000 | Abcam | AB5392 |
| Nestin | Mouse | 1/500 | Neuromics | MO15012 |
| Nkx2.1 (TTF1) | Rabbit | 1/1000 | Epitomics | 2044-1 |
| Nkx2.1 (TTF1) | Goat | 1/100 | SCBT | sc-8762 |
| NOS | Rabbit | 1/1000 | Immunostar | 24287 |
| OLIG2 | Rabbit | 1/1000 | Millipore | AB9610 |
| Parvalbumin | Mouse | 1/2000 | Millipore | MAB1572 |
| Parvalbumin | Rabbit | 1/2000 | Swant | PV25 |
| PAX6 | Mouse | 1/250 | DSHB | PAX6 |
| PAX6 | Rabbit | 1/1000 | Covance | PRB-278P |
| PSD-95 | Rabbit | 1/2000 | Zymed | 51-6900 |
| RAX | Mouse | 1/250 | Abnova | H00008575-B01 |
| SATB2 | Mouse | 1/100 | Abcam | ab51502 |
| SC121 | Mouse | 1/1000 | Stemcells | AB-121-U-050 |
| Somatostatin | Rat | 1/250 | Millipore | MAB354 |
| TBR1 | Rabbit | 1/1000 | Abcam | ab31940 |
| TH | Mouse | 1/1000 | Immunostar | 22941 |
| TuJ1 | Mouse | 1/500 | Covance | MMS-435P |
| VGAT | Rabbit | 1/2000 | Synaptic Systems | 131003 |
| VGLUT1 | guinea pig | 1/5000 | Millipore | AB5905 |
| VIP | Rabbit | 1/1000 | Immunostar | 20077 |

What is claimed is:

1. An in vitro method for differentiating human stem cells comprising:
   contacting human stem cells selected from the group consisting of human pluripotent stem cells, human multipotent stem cells, and combinations thereof with at least one inhibitor of Small Mothers Against Decapentaplegic (SMAD) signaling and with at least one Wingless (Wnt) antagonist; and
   contacting the cells with at least one activator of Sonic Hedgehog (SHH) signaling to obtain differentiated cells expressing FOXG1, wherein the initial contact of the cells with the at least one activator of SHH signaling is at least 6 days from the initial contact of the cells with the at least one inhibitor of SMAD signaling.

2. The method of claim 1, wherein said stem cells are selected from the group consisting of human embryonic stem cells, human adult stem cells, human neural stem cells, human induced pluripotent cells, human primary progenitor cells, and human induced progenitor cells.

3. The method of claim 1, wherein said contacting with the at least one inhibitor of SMAD signaling and said contacting with the at least one Wnt antagonist are carried out simultaneously or sequentially, and each has a duration between about 5 days and about 30 days.

4. The method of claim 3, wherein the contact of the cells with the at least one Wnt antagonist is initiated within 5 days from the initial contact of the cells with the at least one inhibitor of SMAD signaling.

5. The method of claim 1, wherein said at least one inhibitor of SMAD signaling is selected from the group consisting of SB431542, LDN-193189, Noggin PD169316, SB203580, LY364947, A77-01, A-83-01, BMP4, GW788388, GW6604, SB-505124, lerdelimumab, metelimumab, GC-I008, AP-12009, AP-11014, LY550410, LY580276, LY364947, LY2109761, SB-505124, E-616452 (RepSox ALK inhibitor), SD-208, SMI6, NPC-30345, Kİ26894, SB-203580, SD-093, activin-M108A, P144, soluble TBR2-Fc, DMH-1, Dorsomorphin dihydrochloride, derivatives thereof, and combinations thereof.

6. The method of claim 5, wherein the at least one inhibitor of SMAD signaling comprises SB431542 and LDN-193189.

7. The method of claim 6, wherein
   (i) SB431542 is provided at a concentration within the range between about 0.1 µM and about 1 mM in a culture medium comprising said cells;
   (ii) SB431542 is provided at a concentration within the range between about 0.1 µM and about 100 µM in a culture medium comprising said cells;
   (iii) LDN-193189 is provided at a concentration within the range between about 1 nM and about 10 µM in a culture medium comprising said cells;
   (iv) LDN-193189 is provided at a concentration within the range between about 1 nM and about 1 µM in a culture medium comprising said cells;
   or a combination thereof.

8. The method of claim 1, wherein the at least one Wnt antagonist is selected from the group consisting of XAV939, DKK1, DKK-2, DKK-3, Dkk-4, SFRP-1, SFRP-2, SFRP-5, SFRP-3, SFRP-4, WIF-1, Soggy, IWP-2, IWR1, ICG-001, KY0211, Wnt-059, LGK974, IWP-L6, derivatives thereof, and combinations thereof.

9. The method of claim 8, wherein said at least one Wnt antagonist comprises XAV939.

10. The method of claim 8, wherein
   (i) XAV939 is provided at a concentration within the range between about 10 nM and about 500 µM in a culture medium comprising said cells; or
   (ii) XAV939 is provided at a concentration within the range between about 0.2 µM and about 200 µM in a culture medium comprising said cells.

11. The method of claim 1, wherein said at least one activator of SHH signaling is selected from the group consisting of Smoothened agonist (SAG), SAG analog, SHH, C25-SHH, C24-SHH, purmorphamine, Hg—Ag, derivatives thereof, and combinations thereof.

12. The method of claim 11, wherein said at least one activator of SHH signaling comprises recombinant SHH and purmorphamine.

13. The method of claim 12, wherein said recombinant SHH is provided at a concentration within the range between about 5 ng/mL and about 5 µg/mL in a culture medium comprising said cells, purmorphamine is provided at a concentration within the range between about 0.1 µM and about 20 µM in a culture medium comprising said cells.

14. The method of claim 1, wherein
   (i) the contact of the cells with the at least one activator of SHH signaling is concluded from about 5 days to about 30 days from its initiation;
   (ii) the initial contact of the cells with the at least one activator of SHH signaling is between about 8 days and about 18 days from the initial contact of the cells with the at least one inhibitor of SMAD signaling, and the contact of the cells with the at least one activator of SHH signaling is concluded between about 8 days and about 16 days from its initiation;

(iii) the initial contact of the cells with the at least one activator of SHH signaling is no later than about 20 days from the initial contact of the cells with the at least one inhibitor of SMAD signaling;

(iv) the initial contact of the cells with the at least one activator of SHH signaling is no later than about 10 days from the initial contact of the cells with the at least one inhibitor of SMAD signaling;

(v) the initial contact of the cells with the at least one activator of SHH signaling is at least about 8 days and up to about 18 days from the initial contact of the cells with the at least one inhibitor of SMAD signaling; and/or (vi) the initial contact of the cells with the at least one activator of SHH signaling is between 6 days and 8 days from the initial contact of the cells with the at least one inhibitor of SMAD signaling, and the contact of the cells with the at least one activator of SHH signaling is concluded between about 8 days and about 24 days from its initiation.

15. The method of claim 1, wherein said differentiated cells further express at least one marker selected from the group consisting of SST, PV, GABA, calbindin, LHX6, OLIG2, NKX6.2, VGLUT1, MAP2, CTIP2, SATB2, TBR1, DLX2, ASCL1, and combinations thereof.

16. The method of claim 1, wherein said differentiated cells further express at least one marker selected from the group consisting of ChAT, NGF, Ach, VAChT, LHX8, 1, p75 and combinations thereof.

17. The method of claim 1, wherein said contact of the cells with said at least one inhibitor of SMAD signaling, with said at least one Wnt antagonist, and with said at least one activator of SHE signaling are carried out in a culture medium.

18. The method of claim 17, wherein the culture medium is selected from the group consisting of essential 6 media, KSR-based media, N2 media, and combinations thereof.

19. The method of claim 1, wherein the differentiated cells expressing FOXG1 are cortical interneuron precursors.

20. The method of claim 1, comprising
contacting said cells with said at least one inhibitor of SMAD signaling and with at least one Wnt antagonist in a serum-supplemented culturing medium.

21. The method of claim 1, further comprising maturing the differentiated cells.

* * * * *